(12) United States Patent
Massa et al.

(10) Patent No.: US 10,375,959 B2
(45) Date of Patent: Aug. 13, 2019

(54) TERNARY HERBICIDAL COMBINATION COMPRISING SAFLUFENACIL

(71) Applicant: BASF Agro B.V., Arnhem (NL)

(72) Inventors: Dario Massa, Mannheim (DE); Richard Evans, Raleigh, NC (US); Tobias Seiser, Mannheim (DE); Matthias Witschel, Bad Duerkheim (DE); Rex Liebl, Raleigh, NC (US); Alexandre Frateschi, Miguel Hidalgo (MX)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 15/544,574

(22) PCT Filed: Jan. 21, 2016

(86) PCT No.: PCT/EP2016/051177
§ 371 (c)(1),
(2) Date: Jul. 19, 2017

(87) PCT Pub. No.: WO2016/116531
PCT Pub. Date: Jul. 28, 2016

(65) Prior Publication Data
US 2018/0064111 A1 Mar. 8, 2018

(30) Foreign Application Priority Data
Jan. 22, 2015 (EP) ..................... 15152163

(51) Int. Cl.
| | | |
|---|---|---|
| *A01N 33/18* | (2006.01) | |
| *A01N 33/22* | (2006.01) | |
| *A01N 35/10* | (2006.01) | |
| *A01N 37/26* | (2006.01) | |
| *A01N 37/40* | (2006.01) | |
| *A01N 37/48* | (2006.01) | |
| *A01N 39/04* | (2006.01) | |
| *A01N 41/06* | (2006.01) | |
| *A01N 41/10* | (2006.01) | |
| *A01N 43/10* | (2006.01) | |
| *A01N 43/50* | (2006.01) | |
| *A01N 43/54* | (2006.01) | |
| *A01N 43/70* | (2006.01) | |
| *A01N 43/80* | (2006.01) | |
| *A01N 43/84* | (2006.01) | |
| *A01N 43/90* | (2006.01) | |
| *A01N 43/653* | (2006.01) | |

(52) U.S. Cl.
CPC ............ *A01N 43/54* (2013.01); *A01N 33/18* (2013.01); *A01N 33/22* (2013.01); *A01N 37/40* (2013.01); *A01N 37/48* (2013.01); *A01N 39/04* (2013.01); *A01N 41/06* (2013.01); *A01N 43/653* (2013.01); *A01N 43/80* (2013.01); *A01N 43/84* (2013.01); *A01N 2300/00* (2013.01)

(58) Field of Classification Search
CPC combination set(s) only.
See application file for complete search history.

(56) References Cited

U.S. PATENT DOCUMENTS

| 4,487,945 A | 12/1984 | Payne |
|---|---|---|
| 4,670,041 A | 6/1987 | Payne |

(Continued)

FOREIGN PATENT DOCUMENTS

| CN | 1368846 A | 9/2002 |
|---|---|---|
| CN | 1390451 A | 1/2003 |

(Continued)

OTHER PUBLICATIONS

Grossmann et al., "The herbicide saflufenacil (KixorTM) is a new inhibitor of protoporphyrinogen IX oxidase activity," Weed Science, vol. 58, pp. 1-9 (2010).*

(Continued)

*Primary Examiner* — John Pak
(74) *Attorney, Agent, or Firm* — Brinks Gilson & Lione

(57) ABSTRACT

The present invention relates to a herbicidal combination which comprises:
  a) a herbicide A which is 2-chloro-5-[3,6-dihydro-3-methyl-2,6-dioxo-4-(trifluoromethyl)-1-(2H)-pyrimidinyl]-4-fluoro-N-[[methyl-(1-methylethyl)-amino]sulfonyl]benzamide,
  b) a single herbicide B selected from sulfentrazone, flumioxazin, dicamba and their salts and esters, and
  c) at least one herbicide C different from herbicides A and B which is selected from
    C.1) herbicides of the group of acetolactate synthase inhibitors,
    C.2) herbicides of the group of protoporphyrinogen oxidase inhibitors,
    C.3) herbicides of the group of synthetic auxins,
    C.4) herbicides of the group of microtubule inhibitors,
    C.5) herbicides of the group of acetyl-CoA carboxylase inhibitors,
    C.6) herbicides of the group of photosystem II inhibitors,
    C.7) herbicides of the group of pigment synthesis inhibitors, and
    C.8) herbicides of the group of VLCFA inhibitors selected from chloroacetamide herbicides, oxyacetamide herbicides, acetamide herbicides and tetrazolinone herbicides;
  provided that the herbicidal combination does not include pyroxasulfone; provided that in case the components b) or c) comprise dicamba or one of its salts or esters the herbicidal combination does not include imazapyr or one of its salts; and
  provided that if component b) is flumioxazin and component c) is 2,4-D, 2,4-D is present as its 2-ethylhexyl ester.

17 Claims, No Drawings

(56) References Cited

U.S. PATENT DOCUMENTS

| | | | |
|---|---|---|---|
| 5,334,576 A | 8/1994 | Doehner | |
| 5,750,130 A | 5/1998 | Ferrell | |
| 5,877,115 A * | 3/1999 | Fenderson | A01N 37/22 504/129 |
| 5,928,996 A | 7/1999 | Fenderson | |
| 5,972,154 A | 10/1999 | Konya | |
| 5,981,432 A | 11/1999 | Hudetz | |
| 6,013,605 A | 1/2000 | Rees | |
| 6,090,750 A * | 7/2000 | Chollet | A01N 37/40 504/105 |
| 6,339,158 B1 | 1/2002 | Wepplo | |
| 6,534,444 B1 | 3/2003 | Sievernich | |
| 7,344,730 B1 | 3/2008 | Stadler | |
| 7,375,058 B2 | 5/2008 | Zagar | |
| 7,635,404 B1 | 12/2009 | Devic | |
| 7,737,275 B2 | 6/2010 | Hamprecht | |
| 7,846,872 B2 | 12/2010 | Zagar | |
| 7,847,097 B2 | 12/2010 | Gebhardt | |
| 8,362,026 B2 | 1/2013 | Schmidt | |
| 9,585,393 B2 * | 3/2017 | Kirkpatrick | A01N 43/84 |
| 2004/0266623 A1 | 12/2004 | Armbruster | |
| 2008/0081211 A1 | 4/2008 | Tuffe et al. | |
| 2008/0153704 A1 | 6/2008 | Yamaji | |
| 2008/0305954 A1 | 12/2008 | Zawierucha | |
| 2009/0247408 A1 | 10/2009 | Koschnick | |
| 2009/0306142 A1 | 12/2009 | Carson | |
| 2010/0323893 A1 | 12/2010 | Ikeda | |
| 2011/0059849 A1 | 3/2011 | Refardt | |
| 2011/0065579 A1 | 3/2011 | Sievernich | |
| 2011/0098182 A1 | 4/2011 | Mann | |
| 2011/0245079 A1 | 10/2011 | James | |
| 2012/0108429 A1 | 5/2012 | Anderson | |
| 2012/0117676 A1 | 5/2012 | Carlson | |
| 2012/0263775 A1 | 10/2012 | Blei | |
| 2013/0143742 A1 | 6/2013 | Ikeda | |
| 2013/0237417 A1 | 9/2013 | Ikeda | |
| 2013/0274106 A1 | 10/2013 | Ikeda | |
| 2014/0031220 A1 | 1/2014 | Yerkes | |
| 2014/0243200 A1 | 8/2014 | Mann | |
| 2014/0329681 A1 | 11/2014 | Ikeda | |

FOREIGN PATENT DOCUMENTS

| | | | |
|---|---|---|---|
| CN | 102396466 A | 4/2012 | |
| CN | 102461547 A | 5/2012 | |
| CN | 102907421 A | 2/2013 | |
| CN | 103250698 A | 8/2013 | |
| CN | 103283779 A | 9/2013 | |
| CN | 103314958 A | 9/2013 | |
| CN | 103766372 | 5/2014 | |
| CN | 103766372 A | 5/2014 | |
| CS | 270183 B1 | 6/1990 | |
| DE | 19544393 A1 | 5/1997 | |
| DE | 19900571 A1 | 7/1999 | |
| EP | 0081893 A2 | 6/1983 | |
| EP | 0326305 A2 | 8/1989 | |
| EP | 0398692 A2 | 11/1990 | |
| EP | 0585895 A1 | 3/1994 | |
| EP | 1417885 A1 | 5/2004 | |
| EP | 2081893 A2 | 7/2009 | |
| EP | 2777397 A1 | 9/2014 | |
| EP | 3081893 A1 | 10/2016 | |
| FR | 3002413 A1 | 8/2014 | |
| JP | 58013504 A2 | 1/1983 | |
| JP | H06145006 | 5/1994 | |
| JP | 07304610 | 11/1995 | |
| JP | 2006131602 A2 | 5/2006 | |
| WO | WO8802598 A1 | 4/1988 | |
| WO | WO9636229 A1 | 11/1996 | |
| WO | WO9821174 A1 | 5/1998 | |
| WO | WO9946246 A1 | 9/1999 | |
| WO | WO9965314 A1 | 12/1999 | |
| WO | WO0008936 A1 | 2/2000 | |
| WO | 2001083459 | 11/2001 | |
| WO | WO0183459 A2 | 11/2001 | |
| WO | 2003024221 | 3/2003 | |
| WO | WO03024221 A1 | 3/2003 | |
| WO | 2003097587 | 11/2003 | |
| WO | WO03097587 A2 | 11/2003 | |
| WO | WO03097589 A1 | 11/2003 | |
| WO | 2005054208 | 6/2005 | |
| WO | WO05054208 A1 | 6/2005 | |
| WO | 2006005490 | 1/2006 | |
| WO | WO06005490 A2 | 1/2006 | |
| WO | WO06063834 A2 | 6/2006 | |
| WO | 2006097589 | 9/2006 | |
| WO | WO06097589 A2 | 9/2006 | |
| WO | 2006125746 | 11/2006 | |
| WO | WO06125746 A1 | 11/2006 | |
| WO | WO07023099 A1 | 3/2007 | |
| WO | WO2007030886 A1 | 3/2007 | |
| WO | WO07048735 A2 | 5/2007 | |
| WO | WO07071655 A2 | 6/2007 | |
| WO | WO07133522 A2 | 11/2007 | |
| WO | 2008043835 | 4/2008 | |
| WO | WO08043835 A2 | 4/2008 | |
| WO | WO09010475 A2 | 1/2009 | |
| WO | WO09103760 A2 | 8/2009 | |
| WO | 2009115490 | 9/2009 | |
| WO | WO09115434 A2 | 9/2009 | |
| WO | WO09115490 A2 | 9/2009 | |
| WO | WO09127635 A1 | 10/2009 | |
| WO | 2009141367 | 11/2009 | |
| WO | WO09141367 A2 | 11/2009 | |
| WO | WO09153246 A2 | 12/2009 | |
| WO | WO10046268 A2 | 4/2010 | |
| WO | WO10089208 A1 | 8/2010 | |
| WO | WO10136146 A2 | 12/2010 | |
| WO | 2011023759 | 3/2011 | |
| WO | WO11023759 A2 | 3/2011 | |
| WO | WO12057743 A1 | 5/2012 | |
| WO | WO12102703 A1 | 8/2012 | |
| WO | WO13026811 A1 | 2/2013 | |
| WO | WO13040163 A1 | 3/2013 | |
| WO | WO13089207 A1 | 6/2013 | |
| WO | WO13089208 A1 | 6/2013 | |
| WO | 2013134310 | 9/2013 | |
| WO | WO13134310 A1 | 9/2013 | |
| WO | 2014018395 | 1/2014 | |
| WO | WO14018395 A1 | 1/2014 | |
| WO | 2014077343 | 5/2014 | |
| WO | WO14077343 A1 | 5/2014 | |
| WO | 2014149557 | 9/2014 | |
| WO | WO14131958 A1 | 9/2014 | |
| WO | WO15007564 A1 | 1/2015 | |
| WO | WO15022634 A2 | 2/2015 | |
| WO | WO15022635 A1 | 2/2015 | |
| WO | WO15026923 A2 | 2/2015 | |
| WO | WO15041642 A1 | 3/2015 | |
| WO | WO15044150 A2 | 4/2015 | |
| WO | WO15052152 A1 | 4/2015 | |
| WO | WO15052153 A1 | 4/2015 | |
| WO | WO15052173 A1 | 4/2015 | |
| WO | WO15052178 A1 | 4/2015 | |
| WO | WO15091642 A1 | 6/2015 | |
| WO | WO15104242 A1 | 7/2015 | |
| WO | WO15104243 A1 | 7/2015 | |
| WO | WO15134573 A1 | 9/2015 | |
| WO | WO15151088 A1 | 10/2015 | |
| WO | WO15155236 A1 | 10/2015 | |
| WO | WO15158565 A1 | 10/2015 | |
| WO | WO15197392 A1 | 12/2015 | |
| WO | WO16062814 A1 | 4/2016 | |
| WO | 2016113334 | 7/2016 | |
| WO | WO16113334 A1 | 7/2016 | |
| WO | WO16116531 A1 | 7/2016 | |
| WO | WO16120116 A1 | 8/2016 | |
| WO | WO16120355 A2 | 8/2016 | |
| WO | WO16169795 A1 | 10/2016 | |
| WO | WO16180614 A1 | 11/2016 | |
| WO | WO16180642 A1 | 11/2016 | |
| WO | WO17009054 A1 | 1/2017 | |
| WO | WO17009056 A1 | 1/2017 | |

(56) References Cited

FOREIGN PATENT DOCUMENTS

| WO | WO17009060 A1 | 1/2017 |
|---|---|---|
| WO | WO17009061 A1 | 1/2017 |
| WO | WO17009088 A1 | 1/2017 |
| WO | WO17009089 A1 | 1/2017 |
| WO | WO17009090 A1 | 1/2017 |
| WO | WO17009092 A1 | 1/2017 |
| WO | WO17009095 A1 | 1/2017 |
| WO | WO17009124 A1 | 1/2017 |
| WO | WO17009134 A1 | 1/2017 |
| WO | WO17009137 A1 | 1/2017 |
| WO | WO17009138 A1 | 1/2017 |
| WO | WO17009139 A1 | 1/2017 |
| WO | WO17009140 A1 | 1/2017 |
| WO | WO17009142 A1 | 1/2017 |
| WO | WO17009143 A1 | 1/2017 |
| WO | WO17009144 A1 | 1/2017 |
| WO | WO17009145 A1 | 1/2017 |
| WO | WO17009146 A1 | 1/2017 |
| WO | WO17009147 A1 | 1/2017 |
| WO | WO17009148 A1 | 1/2017 |
| WO | WO17021430 A1 | 2/2017 |

OTHER PUBLICATIONS

Corn and Soybean Herbicide Chart, University of Wisconsin-Extension, College of Agricultural and Life Sciences, Jan. 2013.; obtained from the Internet on Aug. 8, 2018: <https://ag.purdue.edu/btny/weedscience/Documents/Herbicide_MOA_CornSoy_12_2012[1].pdf >.*
International Search Report, issued in PCT/EP2016/051177, dated Mar. 14, 2016.
International Preliminary Report on Patentability, issued in PCT/EP2016/051177, dated Jul. 25, 2017.
"The Pesticide Manual", ed. C.D.S Tomlin, British Crop Production Council, Fourteenth Edition, 2006, Entry 647, p. 815.
The Pesticide Manual, ed. C.D.S Tomlin, British Crop Production Council, Fourteenth Edition, (2006), entry 157, pp. 195-196.
The Pesticide Manual, ed. C.D.S Tomlin, British Crop Production Council, Fourteenth Edition, (2006), entry 388, pp. 492-493.
The Pesticide Manual, ed. C.D.S. Tomlin, British Crop Production Council, Fourteenth Edition, (2006), entry 769, pp. 972-973.
The Pesticide Manual, ed. C.D.S. Tomlin, British Crop Production Council, Fourteenth Edition, (2006), entry 567 pp. 1716-1717.
The Pesticide Manual, ed. C.D.S. Tomlin, British Crop Production Council, Fourteenth Edition, (2006), entry 568 pp. 718-719.
Database WPI, Week 199604, Thomson Scientific, London, GB; AN 1996-035789, XP002752882, "Synergistic Herbicidal Composition—Contains Metolachlor or Cinmethylin, and Flupoxam," (1995).
The e-Pesticide Manual, Fifteenth Edition, ed., C.D.S. Tomlin, British Crop Production Council, 2011, Entry 752, p. 1.
The Pesticide Manual, ed. C.D.S Tomlin, British Crop Production Council, Fourteenth Edition , 2006, entry 162, pp. 202-203.
The Pesticide Manual, ed. C.D.S Tomlin, British Crop Production Council, Fourteenth Edition, 2006, entry 404, p. 514.
The Pesticide Manual, ed. C.D.S Tomlin, British Crop Production Council, Fourteenth Edition , 2006, entry 55, pp. 64-65.
The Pesticide Manual, Fourteenth Edition, ed. C.D.S. Tomlin, British Crop Production Council, 2006, Entry 464, pp. 587-589.
Material Safety Data Sheet Material Name Echelon 0.30% 12-0-4 25%SCU Fl, (2012), pp. 1-5, [on-line] retrieved from http://www.turfcaresupply.com/upload/documents/msds/SKU_901560_-_MSDS_US_â€"_ECHELON_0.30_12-0-4_25SCU_FL.pdf, [retrieved on Mar. 6, 2015].
Sugarcane Weed Control, 2007 Louisiana Suggested Weed Control Guide, (2007), pp. 85-99, [on-line] retrieved from http://www.lsuagcenter.com/NR/rdonlyres/719A2391-DC91-459F-B188-B03A21429994/32856/Sugarcane.pdf, [retrieved on Jan. 16, 2014].
The Pesticide Manual, ed. C.D.S. Tomlin, British Crop Production Council, Fourteenth Edition, (2006), entry 732, pp. 928-929.
The Pesticide Manual, ed. C.D.S. Tomlin, British Crop Production Council, Fourteenth Edition, (2006), entry 733, pp. 929-930.
The Pesticide Manual, ed. C.D.S. Tomlin, British Crop Production Council, Fourteenth Edition, {2006), entry 268 pp. 341-343.
Anonymous, Aerosil and Sipernat Products for Optimized Crop Protection Formulations Industry Information, (2012), pp. 1-16, [on-line] retrieved from http://www.aerosil.com/product/aerosil/Documents/II-02241-AEROSIL-and-SIPERNAT-Products-for-Optimized-Crop-Protection-EN.pdf, [retrieved on Mar. 10, 2015].
Anonymous, DuPont Velpar DF Herbicide, [on-line] retrieved from http://www.cdms.net/ldat/ld0BP011.pdf, [retrieved on Mar. 6, 2015].
Anonymous, Material Safety Data Sheet Balance WDG Herbicide, (2008), pp. 1-9, [on-line] retrieved from http://www.agrian.com/pdfs/Balance_WDG_Herbicide_MSDS.pdf, [retrieved on Mar. 10, 2015].
Carbonari et al., Eficácia da Utilização e Grânulos de Argila Como Veículo para a Aplicação aérea de Sulfentrazone e Isoxaflutole em área de Implantação de Eucalipto, Planta Daninha, Viçosa-MG, vol. 28, No. 1, (2010), pp. 207-212, [on-line] retrieved from http://www.scielo.br/pdf/pd/v28n1/24.pdf, [retrieved on Mar. 6, 2015].
Cespedes et al., Bentonite and Anthracite in Alginate-Based Controlled Release Formulations to Reduce Leaching of Chloridazon and Metribuzin in a Calcareous Soil, Chemosphere, vol. 92, No. 8, (2013), pp. 918-924.
Database Caplus, Chemical Abstracts Service, Columbus, OH, Database Accession No. 2013:382624. XP002737177.
Dickinson and Carpenter, Home-made Granular Formulations for Applying Chemicals to Irrigated Rice, International Journal of Pest Management, vol. 23, No. 2, (1977), pp. 234-235.
Ibrahim, Weed Management: Country Status Paper â€" Egypt,Improved Weed Management in the Near East: Proceedings of the FAO Expert Consultation on Improved Weed Management in the Near East, Nicosia, Cyprus, Oct. 30-Nov. 1, 1985, (1995), pp. 100-103.
Kadant Grantek's Biodac Active Ingredients & Formulations Compatible with Biodac, (2011), [on-line] retrieved from http://biodac.net/images/AI and Formulations w_Cover.pdf, [retrieved on May 7, 2014].
Li et al,. Addition of Modified Bentonites in Polymer Gel Formulation of 2,4-D for Its Controlled Release in Water and Soil, Journal of Agricultural and Food Chemistry, vol. 57, No. 7, (2009), pp. 2868-2874.
Li et al., Controlled Release and Retarded Leaching of Pesticides by Encapsulating in Carboxymethyl Chitosan/Bentonite Composite Gel, Journal of Environmental Science and Health, Part B, vol. 47, No. 8, (2012), pp. 795-803.
Mojave Granular Weed Killer MSDS, (1996), p. 1, [on-line] retrieved from http://www.kellysolutions.com/erenewal s/documentsubmit/KellyData\OK\pesticide\MSDS\73718\34913-16-73718\34913-16-73718_Mojave_Granular_Weed_Killer_10_31_2006_12_11_38_PM.pdf, [retrieved on Mar. 6, 2015].
Orsenigo, Chemical Weed Control for Sugarcane on Organic Soils of the Everglades,Everglades Station Mimeo Report 62-5, (1961), pp. 1-10 [on-line] retrieved from http://ufdc.ufl.edu/UF00067483/00001, [retrieved on Jan. 16, 2014].
Peng, Developments in Crop Science (4),The Biology and Control of Weeds in Sugarcane, Chapter 12: Application Techniques and Equipment, (1984), pp. 277-295.
Purdue Agriculture, Herbicide Formulations, available online Feb. 7, 2007, obtained at https://www.agriculture.purdue.edu/fnr/html/faculty/holt/nrcasupplement.pdf.
Schobert et al., Reactions of Chelated Å<3-pentadienyl Iron Complexes with Nucleophiles, Journal of Organometallic Chemistry, vol. 689, (2004), pp. 575-584.
Steward and Nelson, Evaluations of controlled Release PVC and Attaclay Formulations of 2,4-D on Eurasian Watermilfoil, Hyacinth Control Journal, (1972), pp. 35-38, [on-line] retrieved from http://www.apms.org/japm/vol10/v10p35.pdf, [retrieved on Mar. 6, 2015].
Sugar Cane Product Guide, (2010), pp. 1-4 [on-line] retrieved from http://www.farmoz.com/au/Guide/FARMOZ/Sugar_Cane_Product_Guide.pdf [retrieved on Jan. 16, 2014].
The Pesticide Manual, Fourteenth Edition, Ed. C.D_S. Tomlin, British Crop Production Council, entry 677, 2006, pp. 356-857.
The Pesticide Manual, Fourteenth Edition, Ed., C.D.S. Tomlin, British Crop Production Council, entry 5, 2006, pp. 9-10.

(56) References Cited

OTHER PUBLICATIONS

Visavale et al., Granulation and Drying of Modified Clay Incorporated Pesticide Formulation, Drying Technology, vol. 25, No. 7-8, (2007), pp. 1369-1376.
Yeiser, Weed Control and Seedling Performance Using OUST, Velpar, and Velpar+OUST Impregnated Diammonium Phosphate, Faculty Publications, (2002), pp. 260-265, [on-line] retrieved from http://scholarworks.sfasu.edu/cgi/viewcontent.cgi?article=1204&context=forestry, [retrieved on Mar. 6, 2015].
Webster's New World Dictionary, second college edition, The World Publishing Co., NY, (1972), p. 1127.
Office Action, issued in co-pending U.S. Appl. No. 15/740,405, dated Sep. 26, 2018.
Office Action, issued in co-pending U.S. Appl. No. 15/740,031, dated Sep. 26, 2018.
Office Action, issued in co-pending U.S. Appl. No. 15/740,425, dated Sep. 26, 2018.
Office Action, issued in co-pending U.S. Appl. No. 15/743,163, dated Sep. 26, 2018.
Crop Protection Database, Farm Chemical International, "pethoxamid", (2013), pp. 881-882.
Office Action, issued in co-pending U.S. Appl. No. 15/543,890, dated Jul. 9, 2018.
Final Office Action, issued in co-pending U.S. Appl. No. 15/024,462, dated Jun. 13, 2017.
Office Action, issued in co-pending U.S. Appl. No. 15/024,462, dated Oct. 3, 2017.
Office Action, issued in co-pending U.S. Appl. No. 15/024,462, dated Mar. 29, 2018.
Office Action, issued in co-pending U.S. Appl. No. 15/740,401, dated Sep. 27, 2018.
Office Action, issued in co-pending U.S. Appl. No. 15/741,588, dated Aug. 7, 2018.
Office Action, issued in co-pending U.S. Appl. No. 15/739,847, dated Jun. 26, 2018.
Office Action, issued in co-pending U.S. Appl. No. 15/741,586, dated Oct. 1, 2018.
Final Office Action, issued in co-pending U.S. Appl. No. 15/024,462, dated Nov. 27, 2018.
Final Office Action, issued in co-pending U.S. Appl. No. 15/739,847, dated Dec. 26, 2018.

* cited by examiner

TERNARY HERBICIDAL COMBINATION COMPRISING SAFLUFENACIL

This application is a National Stage application of International Application No. PCT/EP2016/051177, filed Jan. 21, 2016. This application also claims priority under 35 U.S.C. § 119 to European Patent Application No. 15152163.0, filed Jan. 22, 2015.

The present invention relates to a herbicidal combination comprising saflufenacil, a herbicide B selected from sulfentrazone, carfentrazone, butafenacil, fomesafen, oxyfluorfen, acifluorfen, lactofen, flumioxazin, clomazone, topramezone, dicamba, 2,4-D, pendimethalin and their salts and esters and at least one herbicide C different therefrom. The combination is particularly useful for preplant burndown.

Burndown, i.e. the complete removal of weeds from the soil by application of herbicides prior to planting or emergence of a crop, is an important tool of modern weed management. Weeds present at planting will generally grow much quicker than crop plants and thus compete very early in the growing season thereby damaging the crop plants and reducing crop yield. Thus, it is desirable to plant the crop in a weed-free seed bed or to assure that essentially no weeds are present when the crop emerges.

Saflufenacil is the common name of the compound 2-chloro-5-[3,6-dihydro-3-methyl-2,6-dioxo-4-(trifluoromethyl)-1-(2H)pyrimidinyl]-4-fluoro-N-[[methyl(1-methylethyl)-amino]sulfonyl]benzamide which is a herbicidal active substance from the group of PPO inhibitors. Saflufenacil has been described in WO 01/083459. Further processes for its preparation are described in WO 03/097589, WO 05/054208, WO 06/097589, WO 06/125746 and WO 08/043835. Saflufenacil is particularly useful for preplant applications and selective preemergence weed control in multiple crops, including corn and soybean.

Sulfentrazone, carfentrazone, butafenacil, fomesafen, oxyfluorfen, acifluorfen, lactofen, flumioxazin, clomazone, topramezone, dicamba, 2,4-D, pendimethalin and their salts and esters are all well-known herbicides that share common characteristics, such as e.g. a good acticity against dicotyledonous weeds. In addition, all of these herbicides have been used in combined applications with at least one second herbicide. However, the effectiveness of such combinations is often not satisfactory and high application rates are still required to achieve an acceptable control of a broad spectrum of weeds. Moreover, the reliability of such combinations depends strongly on the weathering conditions and certain difficult to control weed species may escape. In addition, the herbicidal activity of these compositions often persists only for a short time, which allows effective burndown only within a small timeframe prior to planting a crop. Moreover, the persistence of the herbicidal activity strongly depends upon the weathering conditions.

So far only a very few specific herbicidal mixtures that besides saflufenacil and an additional herbicide selected from sulfentrazone, carfentrazone, butafenacil, fomesafen, oxyfluorfen, acifluorfen, lactofen, flumioxazin, clomazone, topramezone, dicamba, 2,4-D and pendimethalin also include one or more further herbicides have been disclosed.

WO 2013/134310 relates to herbicidal compositions that besides fomesafen and saflufenacil also comprise a herbicide selected from flufenacet, dimethenamid, acetochlor or metolachlor.

WO 2014/077343 inter alia discloses herbicidal compositions including pyraflufen-ethyl, saflufenacil and a further herbicide selected from carfentrazone-ethyl, sulfentrazone, flumioxazin, fomesafen, acifluorfen and oxyfluorfen.

It is an object of the present invention to provide a herbicidal combination, which allows efficient and reliable control of grass and broadleaf weeds in a burndown program. Moreover, the persistence of the herbicidal activity of the combination should be sufficiently long in order to achieve control of the weeds over a sufficient long time period thus allowing a more flexible application. The combination should also have a low toxicity to humans or other mammals. The combinations should also show an accelerated action on harmful plants, i.e. they should effect damaging of the harmful plants more quickly in comparison with application of the individual herbicides.

These and further objects are achieved by the combinations described hereinafter.

Therefore the present invention relates to a herbicidal combination comprising:
a) a herbicide A which is saflufenacil,
b) a single herbicide B selected from sulfentrazone, flumioxazin, dicamba and their salts and esters, and
c) at least one herbicide C different from herbicides A and B which is selected from
  C.1) herbicides of the group of acetolactate synthase inhibitors,
  C.2) herbicides of the group of protoporphyrinogen oxidase inhibitors,
  C.3) herbicides of the group of synthetic auxins,
  C.4) herbicides of the group of microtubule inhibitors,
  C.5) herbicides of the group of acetyl-CoA carboxylase inhibitors,
  C.6) herbicides of the group of photosystem II inhibitors,
  C.7) herbicides of the group of pigment synthesis inhibitors, and
  C.8) herbicides of the group of VLCFA inhibitors selected from chloroacetamide herbicides, oxyacetamide herbicides, acetamide herbicides and tetrazolinone herbicides, provided that the herbicidal combination does not include pyroxasulfone, provided that in case the components b) or c) comprise dicamba or one of its salts or esters the herbicidal combination does not include imazapyr or one of its salts, and provided that if component b) is flumioxazin and component c) is 2,4-D, 2,4-D is present as its 2-ethylhexyl ester.

The invention furthermore relates to the use of a combination as defined herein for controlling undesirable vegetation. When using the combinations of the invention for this purpose the herbicide A, the herbicide B and the at least one herbicide C can be applied simultaneously or in succession, where undesirable vegetation may occur.

The invention furthermore relates to the use of a combination as defined herein for controlling undesirable vegetation for burndown, i.e. for controlling undesirable vegetation in a locus, e.g. a field, where crops will be planted, before planting or emergence of the crop.

The invention furthermore relates to the use of a combination as defined herein for controlling undesirable vegetation in crops which, by genetic engineering or by breeding, are resistant to one or more herbicides and/or pathogens such as plant-pathogenous fungi, and/or to attack by insects; preferably resistant to saflufenacil and/or resistant to the one or more herbicides C and/or resistant to one or more herbicides D, as defined below.

The invention furthermore relates to a method for controlling undesirable vegetation, which comprises applying an herbicidal combination according to the present invention to the undesirable vegetation. Application can be done before, during and/or after, preferably during and/or after, the emergence of the undesirable vegetation. The herbicide A, the herbicide B and the at least one herbicide C can be applied simultaneously or in succession.

The invention in particular relates to a method for controlling undesirable vegetation in crops, which comprises applying a combination as defined herein to a locus of planted crops where undesirable vegetation occurs or might occur or to a locus where crops will be planted before planting or emergence of the crop.

In the methods of the present invention it is immaterial whether the herbicide A, the herbicide B and the one or more herbicides C are formulated jointly or separately and applied jointly or separately, and, in the case of separate application, in which order the application takes place. It is only necessary, that the herbicide A, the herbicide B and the one or more herbicides C are applied in a time frame, which allows simultaneous action of the active ingredients on the undesirable plants.

The invention also relates to an herbicide formulation, which comprises a herbicidally active combination as defined herein and at least one carrier material, including liquid and/or solid carrier materials.

The combinations of the present invention have several advantages over solo application of either saflufenacil or any one of herbicides B and C, and, likewise, over any binary combination of these herbicides. The combination of the present invention show enhanced herbicide action in comparison with the herbicide action of solo action of saflufenacil or any one of herbicides B and C against undesirable vegetation, in particular against difficult to control species such as *Alopecurus myosuroides, Avena fatua, Bromus* spec., *Echinocloa* spec. *Ipomea* spec., *Lolium* spec., *Phalaris* spec., *Setaria* spec., *Digitaria* spec., *Brachiaria* spec., *Amaranthus* spec., *Chenopodium* spec., *Abutilon theophrasti, Galium aparine, Veronica* spec., or *Solanum* spec. Moreover, the combinations of the invention show a persistant herbicidal activity, even under difficult weathering conditions, which allows a more flexible application in burndown applications and minimizes the risk of weeds escaping. The combinations are generally non-toxic or of low toxicity against mammals. Apart form that, the combinations of the present invention show superior crop compatibility with certain conventional crop plants and with herbicide tolerant crop plants, i.e. their use in these crops leads to a reduced damage of the crop plants and/or does not result in increased damage of the crop plants. Thus, the combinations of the invention can also be applied after the emergence of the crop plants. The combinations of the present invention may also show an accelerated action on harmful plants, i.e. they may effect damage of the harmful plants more quickly in comparison with solo or binary applications of the at least three herbicides involved.

As used herein, the terms "controlling" and "combating" are synonyms.

As used herein, the terms "undesirable vegetation", "undesirable species", "undesirable plants", "harmful plants", "undesirable weeds", or "harmful weeds" are synonyms.

The single herbicide B included in the herbicidal combination of the invention is a compound selected from the group of sulfentrazone, flumioxazin, dicamba, their salts and esters, which are all well established and commercially available herbicides that are described e.g. by C. D. S. Tomlin, "The Pesticide Manual", 13th Edition, BCPC (2003), and also "The Compendium of Pesticide Common Names" http://www.alanwood.net/pesticides.

In the combinations of the invention the weight ratio of the single herbicide B to herbicide A is preferably from 550:1 to 1:50, more preferably from 300:1 to 1:30, in particular from 160:1 to 1:20, specifically from 80:1 to 1:10 and particularly preferred from 35:1 to 1:5.

In addition, the weight ratio of herbicide A to herbicide C in the combinations of the invention is preferably from 1:1000 to 250:1, more preferably from 1:500 to 100:1, in particular from 1:250 to 50:1, specifically from 1:150 to 20:1 and particularly preferred from 1:75 to 10:1.

In addition, the weight ratio of herbicide B to herbicides A+C in the combinations of the invention is preferably from 500:1 to 1:1000, more preferably from 250:1 to 1:500, in particular from 150:1 to 1:400, specifically from 75:1 to 1:150 and particularly preferred from 30:1 to 1:60.

If the compounds of herbicide compounds mentioned herein as herbicides B, herbicides C, herbicides D or safeners (see below) have functional groups, which can be ionized, they can also be used in the form of their agriculturally acceptable salts. In general, those salts are suitable whose cations have no adverse effect on the action of the active compounds ("agriculturally acceptable").

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium, 2-(2-hydroxyethoxy)eth-1-ylammonium (diglycolamine salts), di(2-hydroxyeth-1-yl)ammonium (diolamine salts), tris(2-hydroxyeth-1-yl)ammonium (trolamine salts), tris(3-propanol)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

Further preferred cations are cationic polyamines that are characterized in that at least one amino group of the polyamine is present in the cationic form of an ammonium. The cationic polyamines are preferably derived from polyamines of the formula I:

(I)

wherein
R$^1$, R$^2$ and R$^4$ are independently of each other selected from hydrogen and $C_1$-$C_6$-alkyl, preferably $C_1$-$C_3$-alkyl, which is optionally substituted with a hydroxyl group,
R$^3$ and R$^5$ are independently of each other $C_2$-$C_{10}$-alkylene, preferably $C_2$-$C_4$-alkylene,
X is hydroxyl or NR$^6$R$^7$ with R$^6$ and R$^7$ are independently of each other selected from hydrogen and $C_1$-$C_3$-alkyl, and n is an integer from 1 to 20, preferably 1 to 5.

Examples of preferred polyamines of the formula I are diethylenetriamine (DETA), triethylenetetraamine (TETA), tetraethylenepentaamine (TEPA), N,N,N',N'',N''-pentamethyldiethylenetriamine (PMDETA), N,N,N',N'',N''-pentamethyldipropylenetriamine, N,N-bis(3-dimethylaminopropyl)-N-isopropanolamine, N'-(3-(dimethylamino)propyl)-N,N-dimethyl-1,3-propanediamine and N,N-bis(3-aminopropyl)methylamine (BAPMA). Particularly preferred is BAPMA. Of particular relevance in this context is the BAPMA salt of dicamba (herein also named dicamba-BAPMA), wherein dicamba is present in its anionic form and BAPMA in one of its cationic forms with at least one amino group of BAPMA being transformed into the corresponding ammonium group.

In the combinations according to the invention, herbicides C and D as well as safeners that carry a carboxyl group can also be employed in the form of agriculturally acceptable derivatives, for example as amides such as mono- or di-$C_1$-$C_6$-alkylamides or arylamides, as esters, for example as allyl esters, propargyl esters, tefuryl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester. Preferred derivatives are the esters.

In a first embodiment of the invention (embodiment 1), the herbicidal combinations of the invention comprise at least one herbicide C.1 selected from the group of acetolactate synthase (ALS) inhibitors (also termed as acetohydroxy acid synthase (AHAS) inhibitors). ALS inhibitors are compounds, which have a mode of action comprising the inhibition of a step of the branched chain amino acids biosynthesis in plants and which belong to the group B of the HRAC classification system (see HRAC, Classification of Herbicides According to Mode of Action, http://www.plantprotection.org/hrac/MOA.html).

The term "ALS inhibitor" is meant herein to also include the respective salts, isomers and esters of the above mentioned compounds. Suitable salts are e.g. salts of alkaline or earth alkaline metals or ammonium or organoammonium salts, for instance, sodium, potassium, ammonium, isopropyl ammonium etc. Suitable isomers are e.g. stereo isomers such as the enantiomers. Suitable esters are e.g. $C_1$-$C_8$-(branched or non-branched) alkyl esters, such as methyl esters, ethyl esters and isopropyl esters.

According to the present invention the ALS inhibitors of group C.1 are selected from the group consisting of:
C.1.1 triazolopyrimidine herbicides;
C.1.2 sulfonylamino-carbonyl-triazolinone herbicides;
C.1.3 pyrimidinyl(thio) benzoate herbicides;
C.1.4 sulfonylurea herbicides;
C.1.5 imidazolinone herbicides; and
C.1.6 unclassified herbicides.

Triazolopyrimidine herbicides (C.1.1) include e.g. cloransulam, diclosulam, florasulam, flumetsulam, metosulam, penoxsulam and pyroxsulam, and the salts and esters thereof such as cloransulam-methyl.

Sulfonylamino-carbonyl-triazolinone herbicides (C.1.2) include e.g. flucarbazone, propoxycarbazone, thiencarbazone and triafamone, and the salts and esters thereof such as flucarbazone-sodium, propoxycarbazone-sodium and thiencarbazone-methyl.

Pyrimidinyl(thio) benzoate herbicides (C.1.3) include e.g. bispyribac, pyribenzoxim, pyriftalid, pyrimisulfan, pyrithiobac, pyriminobac, the salts and esters thereof such as bispyribac-sodium, pyrithiobac-sodium and pyriminobac-methyl, as well as 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5) and N-(4-bromophenyl)-2-[(4,6-dimethoxy-2-pyrimidinyl)oxy]benzenemethanamine (CAS 420138-01-8).

Sulfonylurea herbicides (C.1.4) include e.g. amidosulfuron, azimsulfuron, bensulfuron, chlorimuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, thifensulfuron, triasulfuron, tribenuron, trifloxysulfuron, triflusulfuron and tritosulfuron, and the esters and salts thereof such as bensulfuron-methyl, chlorimuron-ethyl, ethametsulfuron-methyl, flupyrsulfuron-methyl-sodium, halosulfuron-methyl, iodosulfuron-methyl-sodium, iofensulfuron-sodium, metsulfuron-methyl, primisulfuron-methyl, pyrazosulfuron-ethyl, sulfometuron-methyl, thifensulfuron-methyl, tribenuron-methyl and triflusulfuron-methyl.

Imidazolinone herbicides (C.1.5) include e.g. imazamethabenz, imazamox, imazapic, imazapyr, imazaquin and imazethapyr, and the esters thereof such as imazamethabenz-methyl.

Unclassified herbicides (C.1.6) include e.g. triafamone.

In the combinations of this embodiment 1 the relative weight ratio of saflufenacil (herbicide A) to herbicide C.1 is preferably in the range from 1:100 to 250:1, more preferably in the range from 1:50 to 100:1, in particular from 1:20 to 50:1, specifically from 1:10 to 20:1 and particularly preferred from 1:5 to 10:1. The relative weight ratio of herbicide B to herbicide A+herbicide C.1 is preferably in the range from 500:1 to 1:75, more preferably from 250:1 to 1:50, in particular from 150:1 to 1:30, specifically from 75:1 to 1:10 and particularly preferred from 30:1 to 1:5.

In a preferred embodiment of the invention, the component c) comprises at least one herbicide selected from triazolopyrimidine herbicides, sulfonylamino-carbonyl-triazolinone herbicides, sulfonylurea herbicides and imidazolinone herbicides (embodiment 1.1). Triazolopyrimidine herbicides (group C.1.1), sulfonylamino-carbonyl-triazolinone herbicides (group C.1.2), sulfonylurea herbicides (group C.1.4) and imidazolinone herbicides (group C.1.5) are known e.g. from The Compendium of Pesticide Common Names http://www.alanwood.net/pesticides/.

Triazolopyrimidine herbicides include cloransulam, florasulam, metosulam, pyroxsulam, diclosulam, flumetsulam and penoxsulam and the salts of cloransulam, in particular the sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, and the esters of cloransulam, in particular the $C_1$-$C_8$-alkyl esters, such as methyl ester, ethyl ester or isopropyl ester. A suitable example of such salts is cloransulam-ammonium. A suitable example of such esters is cloransulam-methyl.

Sulfonylamino-carbonyl-triazolinone herbicides include flucarbazone, propoxycarbazone and thiencarbazone and their salts, in particular the sodium salt, potassium salt, ammonium salt or substituted ammonium salt as defined above, in particular mono-, di- and tri-$C_1$-$C_8$-alkylammonium salts such as methylammonium, dimethylammonium and isopropylammonium, and their esters, in particular the $C_1$-$C_8$-alkyl esters, such as methyl ester, ethyl ester or isopropyl ester. Suitable examples of such salts are flucarbazone-sodium and propoxycarbazone-sodium. A suitable example of such esters is thiencarbazone-methyl.

Sulfonylurea herbicides include amidosulfuron, azimsulfuron, bensulfuron, chlorimuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, thifensulfuron, triasulfuron, tribenuron, trifloxysulfuron, triflusulfuron and tritosulfuron and their esters, in particular the $C_1$-$C_8$-alkyl esters, such as methyl ester, ethyl ester or isopropyl ester, and their salts and the salts of their esters, in particular the sodium salt, potassium salt, ammonium salt or substituted ammonium salt as defined above, in particular mono-, di- and tri-$C_1$-$C_8$-alkylammonium salts such as methylammonium, dimethylammonium and isopropylammonium. Suitable examples of such esters are bensulfuron-methyl, chlorimuron-ethyl, ethametsulfuron-methyl, halosulfuron-methyl, metsulfuron-methyl, primisulfuron-methyl, pyrazosulfuron-ethyl, sulfometuron-methyl, thifensulfuron-methyl, tribenuron-methyl and triflusulfuron-methyl. Suitable examples of such salts are flupyrsulfuron-methyl-sodium, iodosulfuron-methyl-sodium and iofensulfuron-sodium.

Imidazolinone herbicides include imazamethabenz, imazamox, imazapic, imazapyr, imazaquin and imazethapyr and their esters, in particular the $C_1$-$C_8$-alkyl esters, such as methyl ester, ethyl ester or isopropyl ester. A suitable example of such esters is imazamethabenz-methyl.

Preferred triazolopyrimidine herbicides include diclosulam, cloransulam, flumetsulam, cloransulam-methyl and mixtures thereof.

Preferred sulfonylamino-carbonyl-triazolinone herbicides include thiencarbazone, thiencarbazone-methyl and mixtures thereof.

Preferred sulfonylurea herbicides include nicosulfuron, rimsulfuron, chlorimuron, thifensulfuron, chlorimuron-ethyl, thifensulfuron-methyl and mixtures thereof.

Preferred imidazolinone herbicides include imazapyr, imazamox, imazapic, imazethapyr and mixtures thereof.

In particular preferred combinations of the embodiment 1.1 the at least one herbicide C comprises at least one herbicide C.1 selected from the group of diclosulam, cloransulam, flumetsulam, thiencarbazone, nicosulfuron, rimsulfuron, chlorimuron, thifensulfuron, imazapyr, imazamox, imazapic, imazethapyr and their agriculturally acceptable salts and esters, such as in particular cloransulam-methyl, thiencarbazone-methyl chlorimuron-ethyl and thifensulfuron-methyl.

In a second embodiment of the invention (embodiment 2), the herbicidal combinations of the invention comprise at least one herbicide C.2 which is an inhibitor of protoporphyrinogen-IX-oxidase (PPO inhibitor). PPO inhibitors are compounds, which have a mode of action comprising the inhibition of a step of the chlorophyll biosynthesis in plants and which belong to the group E of the HRAC classification system (see HRAC, Classification of Herbicides According to Mode of Action, http://www.plantprotection.org/hrac/MOA.html).

Herbicide compounds belonging to the group of PPO inhibitors C.2 include e.g.
C.2.1 pyrimidinedione herbicides;
C.2.2 triazolinone herbicides;
C.2.3 diphenyl ether herbicides;
C.2.4 N-phenyl phthalimide herbicides;
C.2.5 phenylpyrazole herbicides;
C.2.6 thiadiazole herbicides;
C.2.7 oxadiazole herbicides;
C.2.8 oxazolidinedione herbicides; and
C.2.9 unclassified herbicides.

Pyrimidinedione herbicides (group C.2.1) include e.g. benzfendizone, butafenacil, saflufenacil, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4) and their salts.

Triazolinone herbicides (group C.2.2) include e.g. azafenidin, amicarbazone, bencarbazone, carfentrazone, ipfencarbazone and sulfentrazone and their salts, in particular the sodium salts, potassium salts, ammonium salts or substituted ammonium salts as defined above, in particular mono-, di- and tri-$C_1$-$C_8$-alkylammonium salts such as methylammonium, dimethylammonium and isopropylammonium, and their esters, in particular the $C_1$-$C_8$-alkyl esters, such as methyl ester, ethyl ester or isopropyl ester. A suitable example of such esters is carfentrazone-ethyl.

Diphenyl ether herbicides (group C.2.3) include e.g. ethoxyfen, acifluorfen, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen, nitrofen, nitrofluorfen and oxyfluorfen and their salts, in particular the sodium salts, potassium salts, ammonium salts or substituted ammonium salts as defined above, in particular mono-, di- and tri-$C_1$-$C_8$-alkylammonium salts such as methylammonium, dimethylammonium and isopropylammosodium, and their esters, in particular the $C_1$-$C_8$-alkyl esters, such as methyl ester, ethyl ester or isopropyl ester. Suitable examples of such salts are acifluorfen-sodium and fomesafen-sodium. Suitable examples of such esters are ethoxyfen-ethyl, acifluorfen-methyl and fluoroglycofen-ethyl.

N-Phenyl phthalimide herbicides (group C.2.4) include e.g. cinidon, flumioxazin, flumiclorac, flumipropyn and 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione. Also included are the salts of cinidon and flumiclorac, in particular their sodium salts, potassium salts, ammonium salts or substituted ammonium salts as defined above, in particular mono-, di and tri-$C_1$-$C_8$-alkylammonium salts such as isopropylammonium salts, and the esters of cinidon and flumiclorac, in particular their $C_1$-$C_8$-alkyl esters, such as methylesters, ethylesters, isopropyl esters. Suitable examples of such esters are cinidon-ethyl and flumiclorac-pentyl.

Phenylpyrazole herbicides (group C.2.5) include e.g. fluazolate, pyraflufen and methyl (E)-4-[2-chloro-5-[4-chloro-5-(difluoromethoxy)-1H-methyl-pyrazol-3-yl]-4-fluorophenoxy]-3-methoxy-but-2-enoate [CAS 948893-00-3]. Also included are the esters of pyraflufen, in particular its $C_1$-$C_8$-alkyl esters, such as the methylester, the ethylester, the isopropyl ester. A suitable example of such esters is pyraflufen-ethyl.

Thiadiazole herbicides (group C.2.6) include e.g. fluthiacet and thidiazimin. Also included are the esters of fluthiacet, in particular its $C_1$-$C_8$-alkyl esters, such as the methylester, the ethylester, the isopropyl ester. A suitable example of such esters is fluthiacet-methyl.

Oxadiazole herbicides (group C.2.7) include e.g. oxadiargyl and oxadiazon.

Oxazolidinedione herbicides (group C.2.8) include e.g. pentoxazone.

Unclassified herbicides (group C.2.9) include e.g. flufenpyr, profluazol, pyraclonil, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluorommethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4). Also included are the esters of flufenpyr, in particular its $C_1$-$C_8$-alkyl esters, such as the methylester, the ethylester, the isopropyl ester. A suitable example of such esters is flufenpyr-ethyl.

In the combinations of this embodiment 2 the relative weight ratio of saflufenacil (herbicide A) to herbicide C.2 is preferably in the range from 1:200 to 50:1, more preferably in the range from 1:100 to 20:1, in particular from 1:80 to 10:1, specifically from 1:40 to 10:1 and particularly preferred from 1:20 to 10:1. The relative weight ratio of herbicide B to herbicide A+herbicide C.2 is preferably in the range from 500:1 to 1:250, more preferably from 250:1 to 1:175, in particular from 150:1 to 1:100, specifically from 75:1 to 1:50 and particularly preferred from 30:1 to 1:15.

In a preferred embodiment of the invention, the component c) comprises at least one herbicide selected from pyrimidinedione herbicides C.2.1, triazolinone herbicides C.2.2, diphenyl ether herbicides C.2.3 and N-phenyl phthalimide herbicides C.2.4 (embodiment 2.1). Pyrimidinedione herbicides, triazolinone herbicides, diphenyl ether herbicides and N-phenyl phthalimide herbicides, which are a subgroup of dicarboximide herbicides, are known e.g. from C. D. S. Tomlin, "The Pesticide Manual", 13th Edition, BCPC (2003), and also from "The Compendium of Pesticide Common Names" http://www.alanwood.net/pesticides/.

Preferred pyrimidinedione herbicides include carfentrazone, carfentrazone-ethyl, sulfentrazone and mixtures thereof.

Preferred triazolinone herbicides include butafenacil.

Preferred diphenyl ether herbicides include acifluorfen, acifluorfen-sodium, acifluorfen-methyl, fomesafen, fomesafen-sodium, lactofen, oxyfluorfen and mixtures thereof.

Preferred N-phenyl phthalimide herbicides include flumioxazin.

In particular preferred combinations of the embodiment 2.1 the at least one herbicide C comprises at least one herbicide C.2 selected from the group of flumioxazin, carfentrazone, sulfentrazone, butafenacil, acifluorfen, fomesafen, lactofen, oxyfluorfen and their agriculturally acceptable salts and esters, such as in particular fomesafen-sodium, acifluorfen-sodium, acifluorfen-methyl, carfentrazone-ethyl.

In a third embodiment of the invention (embodiment 3), the herbicidal combinations of the invention comprise at least one herbicide C.3 which is a synthetic auxin. Synthetic auxins are compounds which act like the phytohormones auxins such as indole-3-acetic acid. Synthetic auxins belong to the group O of the HRAC classification system (see HRAC, Classification of Herbicides According to Mode of Action, http://www.plantprotection.org/hrac/MOA.html).

Herbicide compounds belonging to the group of synthetic auxins C.3 include e.g.

C.3.1 benzoic acid herbicides;
C.3.2 quinolinecarboxylic acid herbicides;
C.3.3 pyridine carboxylic acid herbicides;
C.3.4 phenoxycarboxylic acid herbicides; and
C.3.5 unclassified herbicides.

Benzoic acid herbicides (C.3.1) include e.g. dicamba, tricamba, chloramben and 2,3,6-TBA (2,3,6-trichlorobenzoic acid), and the salts and esters thereof.

Quinolinecarboxylic acid herbicides (C.3.2) include e.g. quinclorac and quinmerac, and the salts and esters thereof.

Pyridinecarboxylic acid herbicides (C.3.3) include e.g. aminopyralid, clopyralid, halauxifen, picloram, triclopyr and fluroxypyr, and their salts and their esters, such as aminopyralid-dimethylammonium, aminopyralid-tris(2-hydroxypropyl)ammonium, fluroxypyr-butometyl and fluroxypyr-meptyl.

Phenoxycarboxylic acid herbicides (C.3.4) include, e.g. phenoxyacetic acid herbicides such as 2,4-D, 3,4-DA, MCPA, MCPA-thioethyl, 2,4,5-T, phenoxypropionic acid herbicides such as 2,4-DP (dichlorprop), 2,4-DP-P, 4-CPP, 3,4-DP, fenoprop, CMPP (mecoprop), CMPP-P (mecoprop-P), and phenoxybutyric acid herbicides such as 4-CPB, 2,4-DB, 3,4-DB, 2,4,5-TB, MCPB, and their salts and their esters.

Unclassified herbicides (C.3.5) include, e.g. clacyfos, aminocyclopyrachlor, benazolin and clomeprop, and their salts and their esters, such as benazolin-ethyl.

In the combinations of this embodiment 3 the relative weight ratio of saflufenacil (herbicide A) to herbicide C.3 is preferably in the range from 1:250 to 5:1, more preferably in the range from 1:200 to 1:1, in particular from 1:150 to 1:1, specifically from 1:100 to 1:2 and particularly preferred from 1:70 to 1:2. The relative weight ratio of herbicide B to herbicide A+herbicide C.3 is preferably in the range from 80:1 to 1:800, more preferably from 40:1 to 1:400, in particular from 20:1 to 1:200, specifically from 10:1 to 1:100 and particularly preferred from 5:1 to 1:60.

In a preferred embodiment of the invention, the component c) comprises at least one herbicide selected from benzoic acid herbicides C.3.1 and phenoxycarboxylic acid herbicides C.3.4 (embodiment 3.1). Benzoic acid herbicides and phenoxycarboxylic acid herbicides, as well as herbicides C.3.2 and C.3.3, are known e.g. from C. D. S. Tomlin, "The Pesticide Manual", 13th Edition, BCPC (2003), and also from "The Compendium of Pesticide Common Names" http://www.alanwood.net/pesticides/.

Preferred benzoic acid herbicides C.3.1 include dicamba, tricamba, chloramben and 2,3,6-TBA (2,3,6-trichlorobenzoic acid) and the salts the esters thereof, in particular their sodium salt, potassium salt, ammonium salt, substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyl-ethyl)ammonium, tri(hydroxyethyl)ammonium, hydroxypropylammonium, di(hydroxypropyl)ammonium and tri(hydroxypropyl)ammonium salts, or cationic polyamines as defined above, in particular BAPMA salts, and their esters, in particular its $C_1$-$C_8$-alkyl esters and $C_1$-$C_4$-alkoxy-$C_2$-$C_4$-alkyl esters, such as methyl, ethyl, isopropyl, butyl, hexyl, heptyl, isoheptyl, isooctyl, 2-ethylhexyl and butoxyethyl esters. Suitable examples of such salts are dicamba-sodium, dicamba-potassium, dicamba-methylammonium, dicamba-isopropylammonium, dicamba-dimethylammonium, dicamba-diglycolammonium, dicamba-olamine, dicamba-diolamine, dicamba-trolamine, dicamba-BAPMA, tricamba-sodium, tricamba-potassium, tricamba-methylammonium, tricamba-isopropylammonium, tricamba-olamine, tricamba-diolamine, tricamba-trolamine, chloramben-ammonium, chloramben-methylammonium, chloramben-sodium, chloramben-diolamine, 2,3,6-T-sodium, 2,3,6-dimethylammonium. Suitable examples of such esters are dicamba-methyl and chloramben-methyl.

Particularly preferred benzoic acid herbicides C.3.1 include dicamba at its aforemented salts and esters. Even more preferred benzoic acid herbicides are dicamba and its salts, such as dicamba-sodium.

Preferred phenoxycarboxylic acid herbicides C.3.4 include 2,4-D, 2,4-DP (dichlorprop), 2,4-DP-P (dichlorprop-P), CMPP (mecoprop), CMPP-P, MCPA, MCPA-thioethyl, MCPB, their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters. Suitable examples of such salts and esters are for example 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-diolamine, 2,4-D-dimethylammonium, 2,4-D-dodecylammonium, 2,4-D-ethyl, 2,4-D-2-ethylhexyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris (2-hydroxypropyl)ammonium, 2,4-D-trolamine, MCPA-butotyl, MCPA-butyl, MCPA-dimethylammonium, MCPA-diolamine, MCPA-ethyl, MCPA-2-ethylhexyl, MCPA-isobutyl, MCPA-isoctyl, MCPA-isopropyl, MCPA-methyl, MCPA-olamine, MCPA-potassium, MCPA-sodium, MCPA-trolamine, dichlorprop-butotyl, dichlorprop-dimethylammonium, dichlorprop-ethylammonium, dichlorprop-2-ethylhexyl, dichlorprop-isoctyl, dichlorprop-methyl, dichlorprop-potassium, dichlorprop-sodium, diclopop-P-dimethylammonium, mecoprop-dimethylammonium, mecoprop-diolamine, mecoprop-ethadyl, mecoprop-isoctyl, mecoprop-methyl, mecoprop-potassium, mecoprop-sodium, mecoprop-trolamine, mecoprop-P-dimethylammonium, mecoprop-P-isobutyl, mecoprop-P-potassium, MCPB-methyl, MCPB-ethyl and MCPB-sodium.

Particularly preferred phenoxycarboxylic acid herbicides C.3.4 include 2,4-D and its aforementioned salts and esters.

In particular preferred combinations of the embodiment 3.1 the at least one herbicide C comprises at least one herbicide C.3 selected from dicamba, 2,4-D and their agriculturally acceptable salts and esters.

In a fourth embodiment of the invention (embodiment 4), the herbicidal compositions of the invention comprise at least one herbicide C.4 which is an inhibitor of microtubule assembly (MTA inhibitor). MTA inhibitors are compounds which have a mode of action comprising the inhibition of the microtubule assembly in plants and which belong to the group K1 of the HRAC classification system (see HRAC, Classification of Herbicides According to Mode of Action, http://www.plantprotection.org/hrac/MOA.html).

MTA inhibitors of the group C.4 include e.g. dinitroaniline herbicides (C.4.1), such as benfluralin, butralin, dinitramine, ethalfluralin, fluchloralin, oryzalin, pendimethalin, prodiamine and trifluralin, phosphoroamidate herbicides (C.4.2), such as amiprophos, amiprophos-methyl and butamiphos, pyridine herbicides (C.4.3), such as dithiopyr and thiazopyr, benzamide herbicides (C.4.4), such as propyzamide and tebutam, and benzoic acid herbicides (C.4.5), such as chlorthal and chlorthal-dimethyl. The term "MTA inhibitor" is meant herein to also include the respective salts, isomers and esters of the above mentioned compounds. Suitable salts are e.g. salts of alkaline or earth alkaline metals or ammonium or organoammonium salts, for instance, sodium, pottasium, ammonium, isopropyl ammonium etc. Suitable isomers are e.g. stereo isomers such as the enantiomers. Suitable esters are e.g. $C_1$-$C_8$-(branched or non-branched) alkyl esters, such as methylesters, ethylesters, iso propyl esters.

Preferred MTA inhibitors according to the present invention are selected from the group consisting of dinitroaniline herbicides C.4.1, in particular benfluralin, butralin, dinitramine, ethalfluralin, fluchloralin, isopropalin, methalpropalin, nitralin, oryzalin, pendimethalin, prodiamine, profluralin and trifluralin, more preferably oryzalin, pendimethalin and trifluralin. Dinitroaniline herbicides are known e.g. from U.S. Pat. Nos. 3,257,190: 3,321,292; 3,367,949; C. D. S. Tomlin, "The Pesticide Manual", 13th Edition, BCPC (2003) and also from The Compendium of Pesticide Common Names, http://www.alanwood.net/pesticides/.

In the combinations of this embodiment 4 the relative weight ratio of saflufenacil (herbicide A) to herbicide C.4 is preferably in the range from 1:1000 to 1:1, more preferably in the range from 1:500 to 1:2, in particular from 1:250 to 1:5, specifically from 1:150 to 1:5 and particularly preferred from 1:75 to 1:10. The relative weight ratio of herbicide B to herbicide A+herbicide C.4 is preferably in the range from 20:1 to 1:1000, more preferably from 10:1 to 1:500, in particular from 5:1 to 1:250, specifically from 2:1 to 1:150 and particularly preferred from 2:1 to 1:60.

In a particular preferred combination of this embodiment 4 the at least one herbicide C comprises at least one herbicide C.4 which is pendimethalin.

In a fifth embodiment of the invention (embodiment 5), the herbicidal combinations of the invention comprise at least one herbicide C.5 which is an inhibitor of the acetyl-CoA carboxylase (ACC inhibitor). ACC inhibitors are compounds which have a mode of action comprising the inhibition of the lipid biosynthesis in plants and which belong to the group A of the HRAC classification system (see HRAC, Classification of Herbicides According to Mode of Action, http://www.plantprotection.org/hrac/MOA.html).

Suitable ACC inhibitors of the group C.5 are known from e.g. C. D. S. Tomlin, "The Pesticide Manual", 13th Edition, BCPC (2003) and also from The Compendium of Pesticide Common Names http://www.alanwood.net/pesticides/.

The term "ACC inhibitor" is meant herein to also include the respective salts, isomers and esters of the above mentioned compounds. Suitable salts are e.g. salts of alkaline or earth alkaline metals or ammonium or organoammonium salts, for instance, sodium, pottasium, ammonium, isopropyl ammonium etc. Suitable isomers are e.g. stereo isomers such as the enantiomers. Suitable esters are e.g. propargyl esters, tefuryl (tetrahydrofurfuryl) esters, etotyl (ethoxyethyl) esters, $C_1$-$C_8$-(branched or non-branched) alkyl esters, such as methyl esters, ethyl esters, isopropyl esters, butyl esters and isobutyl esters.

Herbicide compounds belonging to the group of ACC inhibitors include e.g.

C.5.1 aryloxyphenoxy-propionate herbicides;
C.5.2 cyclohexanedione herbicides;
C.5.3 phenylpyrazoline herbicides; and
C.5.4 unclassified herbicides.

Aryloxyphenoxy-propionate herbicides (C.5.1) include e.g. chlorazifop, clodinafop, clofop, cyhalofop, diclofop, fenoxaprop, fenthiaprop, fluazifop, haloxyfop, isoxapyrifop, kuicaoxi, metamifop, propaquizafop, quizalofop, trifop and their enantiomers, salts and esters, such as fenoxaprop-P, fluazifop-P, haloxyfop-P, quizalofop-P, haloxyfop-sodium, chlorazifop-propargyl, clodinafop-propargyl, clofop-isobutyl, cyhalofop-butyl, diclofop-methyl, fenoxaprop-ethyl, fenoxaprop-P-ethyl, fenthiaprop-ethyl, fluazifop-methyl, fluazifop-butyl, fluazifop-P-butyl, haloxyfop-etotyl, haloxyfop-methyl, haloxyfop-P-etotyl, haloxyfop-P-methyl, quizalofop-ethyl, quizalofop-tefuryl, quizalofop-P-ethyl and quizalofop-P-tefuryl.

Cyclohexanedione herbicides (C.5.2) include e.g. alloxydim, butroxydim, clethodim, cloproxydim, cycloxydim, profoxydim, sethoxydim, tepraloxydim, tralkoxydim and their salts, such as alloxydim-sodium.

Phenylpyrazoline herbicides (C.5.3) include in particular pinoxaden.

Unclassified herbicides (C.5.4) include e.g. 4-(4'-chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-cichloro-4-ethyl[1,1'-biphenyl]-3-yl)-2,2,6,6-tetramethyl-2H-pyran-3,5(4H,6H)-dione (CAS 1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(acetyloxy)-4-(2',4'-dichloro-4-cyclopropyl-[1,1'-biphenyl]-3-yl)-3,6-dihydro-2,2,6,6-tetramethyl-2H-pyran-3-one; 5-(acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); and 4-(2',4'-dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5), as described in WO 2010/136431, WO 2011/073615 and WO 2011/073616.

In the combinations of this embodiment 5 the relative weight ratio of saflufenacil (herbicide A) to herbicide C.5 is preferably in the range from 1:100 to 100:1, more preferably in the range from 1:50 to 50:1, in particular from 1:25 to 25:1, specifically from 1:10 to 10:1 and particularly preferred from 1:5 to 5:1. The relative weight ratio of herbicide B to herbicide A+herbicide C.5 is preferably in the range from 500:1 to 1:100, more preferably from 150:1 to 1:50, in particular from 80:1 to 1:40, specifically from 40:1 to 1:15 and particularly preferred from 20:1 to 1:5.

In a preferred embodiment of the invention, the component c) comprises at least one herbicide selected from aryloxyphenoxy-propionate herbicides C.5.1 and cyclohexanedione herbicides C.5.2 (embodiment 5.1).

In another preferred embodiment of the invention, the component c) comprises at least one herbicide selected from aryloxyphenoxy-propionate herbicides C.5.1 (embodiment 5.2).

Preferred aryloxyphenoxy-propionate herbicides include fenoxaprop and haloxyfop, their enantiomers, salts and esters, and mixtures thereof.

Preferred cyclohexanedione herbicides include clethodim, profoxydim and sethoxydim.

In particular preferred combinations of the embodiment 5.1 the at least one herbicide C comprises at least one herbicide C.5 selected from the group of fenoxaprop, haloxyfop, clethodim, profoxydim, sethoxydim and their agriculturally acceptable enantiomers, salts and esters, such as in particular fenoxaprop-P, haloxyfop-P, haloxyfop-sodium, fenoxaprop-ethyl, fenoxaprop-P-ethyl, haloxyfop-etotyl, haloxyfop-methyl, haloxyfop-P-etotyl and haloxyfop-P-methyl.

In particular preferred combinations of the embodiment 5.2 the at least one herbicide C comprises at least one herbicide C.5 selected from the group of fenoxaprop, haloxyfop and their agriculturally acceptable enantiomers, salts and esters, such as in particular fenoxaprop-P, haloxyfop-P, haloxyfop-sodium, fenoxaprop-ethyl, fenoxaprop-P-ethyl, haloxyfop-etotyl, haloxyfop-methyl, haloxyfop-P-etotyl and haloxyfop-P-methyl.

In a sixth embodiment of the invention (embodiment 6), the herbicidal combinations of the invention comprise at least one herbicide C.6 which is an inhibitor of electron transfer in photosynthesis in plants. These compounds have a mode of action comprising the inhibition of the electron transfer in photosystem II of the photosynthesis in plants (PS II inhibitors). They belong to the groups C1 to C3 of the HRAC classification system (see HRAC, Classification of Herbicides According to Mode of Action, http://www.plant-protection.org/hrac/MOA.html).

Suitable PSII inhibitors are selected from the group consisting of:

C.6.1 arylurea herbicides;
C.6.2 triazin(di)one herbicides;
C.6.3 triazine herbicides;
C.6.4 pyridazinone herbicides;
C.6.5 phenylcarbamate herbicides;
C.6.6 nitrile herbicides;
C.6.7 benzothiadiazinone herbicides; and
C.6.8 uracil herbicides.

PS II inhibitors are known e.g. from K.-W. Münks and K.-H. Müller "Photosynthesis Inhibitors" in "Modern Crop Protection Compounds" Vol. 1, Wiley-VHC 2007, pp 359-400; C. D. S. Tomlin, "The Pesticide Manual", 13th Edition, BCPC (2003) and also from The Compendium of Pesticide Common Names, http://www.alanwood.net/pesticides/.

The term "PS II inhibitor" is meant herein to also include the respective salts, isomers and esters of the above mentioned compounds. Suitable salts are e.g. salts of alkaline or earth alkaline metals or ammonium or organoammonium salts, for instance, sodium, potassium, ammonium, isopropyl ammonium etc. Suitable isomers are e.g. stereo isomers such as the enantiomers. Suitable esters are e.g. $C_1$-$C_8$-(branched or non-branched) alkyl esters, such as methyl esters, ethyl esters and isopropyl esters.

Arylurea herbicides herbicides (C.6.1) include e.g. chlorbromuron, chlorotoluron, chloroxuron, dimefuron, diuron, ethidimuron, fenuron, fluometuron, isoproturon, isouron, linuron, methabenzthiazuron, metobenzuron, metobromuron, metoxuron, monolinuron, neburon, siduron, tetrafluron, tebuthiuron, thiadiazuron and their salts and esters. Preferred arylurea herbicides herbicides (C.6.1) include chlortoluron, diuron, linuron, isoproturon and tebuthiuron.

Triazin(di)one herbicides (C.6.2) (i.e. triazinone and triazindione herbicides) include e.g. ametridione, amibuzin, ethiozin, hexazinone, isomethiozin, metamitron, metribuzin, trifludimoxazin and their salts and esters. Preferred triazin (di)one herbicides (C.6.2) include hexazinone, metamitron and metribuzin, in particular metribuzin.

Triazine herbicides (C.6.3) include e.g. ametryn, atrazine, aziprotryne, chlorazine, cyanatryn, cyanazine, cyprazine, desmetryn, dimethametryn, eglinazine, ipazine, mesoprazine, methoprotryne, prometryn, procyazine, proglinazine, prometon, propazine, sebuthylazine, simazine, simetryn, terbumeton, terbuthylazine, terbutryn, trietazine and their salts and esters, such as eglinazine-ethyl and proglinazine-ethyl. Preferred triazine herbicides (C.6.3) include ametryn, atrazine, terbuthylazine and simazine, in particular atrazine.

Pyridazinone herbicides (C.6.4) include e.g. brompyrazon, chloridazon, dimidazon, metflurazon, norflurazon, oxapyrazon, pydanon and their salts and esters. A preferred pyridazinone herbicide is chloridazon.

Phenylcarbamate herbicides (C.6.5) include e.g. desmedipham, karbutilate, phenisopham, phenmedipham and their salts and esters, such as phenmedipham-ethyl.

Nitrile herbicides (C.6.6) include e.g. bromobonil, bromofenoxim, bromoxynil, chloroxynil, dichlobenil, iodobonil and ioxynil and their salts and esters, in particular in case of bromoxynil, chloroxynil and ioxynil. A preferred nitrile herbicide is bromoxynil.

Benzothiadiazinone herbicides (C.6.7) include bentazone and its salts, in particular its alkalimetal salts, such as bentazone-sodium.

Uracil herbicides (C.6.8) include e.g. bromacil, flupropacil, isocil, lenacil, terbacil and the salts of bromacil, in particular its alkalimetal salts, such as bromacil-lithium and bromacil-sodium.

In the combinations of this embodiment 6 the relative weight ratio of saflufenacil (herbicide A) to herbicide C.6 is preferably in the range from 1:1000 to 5:1, more preferably in the range from 1:500 to 2:1, in particular from 1:250 to 1:1, specifically from 1:150 to 1:2 and particularly preferred from 1:75 to 1:2. The relative weight ratio of herbicide B to herbicide A+herbicide C.6 is preferably in the range from 100:1 to 1:1000, more preferably from 50:1 to 1:500, in particular from 20:1 to 1:400, specifically from 10:1 to 1:150 and particularly preferred from 5:1 to 1:60.

In a preferred embodiment of the invention, the component c) comprises at least one herbicide selected from
  triazin(di)one herbicides C.6.2, in particular hexazinone, metamitron and/or metribuzin, especially metribuzin;
  triazine herbicides C.6.3, in particular atrazine and/or terbuthylazine, especially atrazine; and
  benzothiadiazinone herbicides C.6.7, in particular bentazone.

In particular preferred combinations of the embodiment 6 the at least one herbicide C comprises at least one herbicide C.6 selected from metribuzin, atrazine, bentazone and their agriculturally acceptable salts.

In a seventh embodiment of the invention (embodiment 7), the herbicidal combinations of the invention comprise at least one herbicide C.7 which is an inhibitor of pigment synthesis. Pigment synthesis inhibitors are compounds which have a mode of action comprising the inhibition of the carotenoid biosynthesis in plants and which belong to the groups F1 to F4 of the HRAC classification system (see HRAC, Classification of Herbicides According to Mode of Action, http://www.plantprotection.org/hrac/MOA.html).

The term "pigment synthesis inhibitor" is meant herein to also include the respective salts, isomers and esters of the above mentioned compounds.

Suitable pigment synthesis inhibitors are selected from the group consisting of:
  C.7.1 phytoene desaturase (PDS) inhibitors;
  C.7.2 4-hydroxyphenylpyruvate dioxygenase (HPPD) inhibitors;
  C.7.3 inhibitors of unknown target; and
  C.7.4 1-deoxyxylulose-5-phosphate (DOXP) synthase inhibitors.

PDS inhibitors (C.7.1) are known from e.g. G. Hamprecht et al. "Phytoene Desaturase Inhibitors" in "Modern Crop Protection Compounds" Vol. 1, Wiley-VHC 2007, pp 187-211; from EP 723960, from C. D. S. Tomlin, "The Pesticide Manual", 13th Edition, BCPC (2003) and also from The Compendium of Pesticide Common Names http://www.alanwood.net/pesticides/.

Suitable PDS inhibitors C.7.1 include e.g. pyridazinone herbicides, such as norflurazon, pyridinecarboxamide herbicides, such as flufenican, diflufenican and picolinafen, as well as herbicides not belonging to a common group, such as beflubutamid, fluridone, fluorochloridone, flurtamone and 4-(3-trifluoromethylphenoxy)-2-(4-trifluoromethylphenyl) pyrimidine (CAS 180608-33-7). Preferred PDS inhibitors according to the present invention are selected from the group consisting of pyridinecarboxamide herbicides, such as flufenican, diflufenican and picolinafen.

HPPD inhibitors (C.7.2), inhibitors of unknown target (C.7.3) and DOXP synthase inhibitors (C.7.4) are known from e.g. C. D. S. Tomlin, "The Pesticide Manual", 13th Edition, BCPC (2003) and also from The Compendium of Pesticide Common Names http://www.alanwood.net/pesticides/.

Suitable HPPD inhibitors C.7.2 include e.g. cyclopropylisoxazole herbicides C.7.2.1, such as isoxachlortole and isoxaflutole, benzoylcyclohexanedione herbicides C.7.2.2, such as fenquinotrione, ketospiradox, mesotrione, sulcotrione, tefuryltrione and tembotrione, benzoylpyrazole herbicides C.7.2.3, such as benzofenap, pyrasulfotole, pyrazolynate, pyrazoxyfen, tolpyralate and topramezone, as well as unclassified herbicides, such as benzobicyclon and bicyclopyrone.

Isoxaflutole is a well known herbicide and commercially available, e.g. under the trade name BALANCE® and MERLIN®. Mesotrione is a well known herbicide and commercially available, e.g. under the trade name CALLISTO®. Sulcotrione is a well known herbicide and commercially available, e.g. under the trade name MIKADO®.

Tropramzone is a well known herbicide and commercially available, e.g. under the trade names IMPACT® and CLIO®.

Suitable inhibitors of unknown target C.7.3 include e.g. amitrole, fluometuron and aclonifen.

Suitable DOXP synthase inhibitors C.7.4 inhibitors include e.g. clomazone.

In the combinations of this embodiment 7 the relative weight ratio of saflufenacil (herbicide A) to herbicide C.7 is preferably in the range from 1:250 to 100:1, more preferably in the range from 1:100 to 50:1, in particular from 1:50 to 20:1, specifically from 1:20 to 10:1 and particularly preferred from 1:10 to 5:1. The relative weight ratio of herbicide B to herbicide A+herbicide C.7 is preferably in the range from 450:1 to 1:250, more preferably from 150:1 to 1:100, in particular from 75:1 to 1:50, specifically from 40:1 to 1:30 and particularly preferred from 20:1 to 1:10.

In a preferred embodiment of the invention, the component c) comprises at least one herbicide selected from HPPD inhibitors C.7.2 and DOXP synthase inhibitors C.7.4, and specifically selected from
  cyclopropylisoxazole herbicides C.7.2.1, in particular isoxaflutole;
  benzoylcyclohexanedione herbicides C. 7.2.2, in particular mesotrione and/or tembotrione;
  benzoylpyrazole herbicides C.7.2.3, in particular topramezone;
  bicyclopyrone; and
  DOXP synthase inhibitors C.7.4, in particular clomazone.

In particular preferred combinations of the embodiment 7 the at least one herbicide C comprises at least one herbicide C.7 selected from isoxaflutole, mesotrione, tembotrione, topramezone, bicyclopyrone, clomazone and their agriculturally acceptable salts.

In an eighth embodiment of the invention (embodiment 8), the herbicidal combinations of the invention comprise at least one herbicide C.8 which is an inhibitor of the very long chain fatty acid (VLCFA) synthesis inhibitor. VLCFA inhibitors are compounds which have a mode of action comprising the inhibition of the VLCA synthesis and/or the inhibition of cell division in plants and which belong to the group K3 of the HRAC classification system (see HRAC, Classification of Herbicides According to Mode of Action, http://www-.plantprotection.org/hrac/MOA.html).

Herbicides C.8 are selected from:
  C.8.1 chloroacetamide herbicides, such as acetochlor, alachlor, butachlor, dimethachlor, dimethenamid, metazachlor, metolachlor, pethoxamid, pretilachlor, propachlor, propisochlor, thenylchlor and their enantiomers, salts and esters, such as dimethenamid-P and S-metolachlor,
  C.8.2 oxyacetamide herbicides, such as flufenacet and mefenacet,
  C.8.3 acetamide herbicides, such as as diphenamid, napropamide, naproanilide and their enantiomers, such as napropamide-M, and
  C.8.4 tetrazolinone herbicides, such as fentrazamide.

VLCFA inhibitors of the groups C.8.1 to C.8.4 are known from e.g. C. D. S. Tomlin, "The Pesticide Manual", 13th Edition, BCPC (2003) and also from The Compendium of Pesticide Common Names http:www.alanwood.net/pesticides/.

The term "VLCFA inhibitor" is meant herein to also include the respective salts, isomers and esters of the above mentioned compounds. Suitable salts are e.g. salts of alkaline or earth alkaline metals or ammonium or organoammonium salts, for instance, sodium, pottasium, ammonium, isopropyl ammonium etc. Suitable isomers are e.g. stereo isomers such as the enantiomers. Suitable esters are e.g. $C_1$-$C_8$-(branched or non-branched) alkyl esters, such as methyl esters, ethyl esters, isopropyl esters.

In the combinations of this embodiment 8 the relative weight ratio of saflufenacil (herbicide A) to herbicide C.8 is preferably in the range from 1:1000 to 10:1, more preferably in the range from 1:500 to 5:1, in particular from 1:250 to 2:1, specifically from 1:150 to 2:1 and particularly preferred from 1:75 to 1:1. The relative weight ratio of herbicide B to herbicide A+herbicide C.8 is preferably in the range from 100:1 to 1:500, more preferably from 50:1 to 1:250, in particular from 20:1 to 1:200, specifically from 20:1 to 1:100 and particularly preferred from 15:1 to 1:60.

In a preferred embodiment of the invention, the component c) comprises at least one herbicide selected from chloroacetamide herbicides C.8.1 and oxyacetamide herbicides C.8.2 (embodiment 8.1).

Preferred chloroacetamide herbicides include acetochlor, dimethenamid, metazachlor, metolachlor, their enantiomers, such as in particular dimethenamid-P and S-metolachlor, and mixtures thereof.

Preferred oxyacetamide herbicides include in particular flufenacet.

In particular preferred combinations of the embodiment 8.1 the at least one herbicide C comprises at least one herbicide C.8 selected from the group of acetochlor, dimethenamid, metazachlor, metolachlor, flufenacet and their agriculturally acceptable enantiomers, such as in particular dimethenamid-P and S-metolachlor.

The single herbicide B of the herbicidal combination according to the present invention is a compound selected from the group of sulfentrazone, flumioxazin, dicamba and their salts and esters, such as in particular dicamba-sodium, dicamba-potassium, dicamba-methylammonium, dicamba-isopropylammonium, dicamba-dimethylammonium, dicamba-diglycolammonium, dicamba-olamine, dicamba-diolamine, dicamba-trolamine and dicamba-BAPMA.

In a particularly preferred embodiment of the invention the herbicide B is selected from the group of sulfentrazone, flumioxazin, dicamba, dicamba-sodium, dicamba-potassium, dicamba-isopropylammonium, dicamba-dimethylammonium, dicamba-diglycolammonium, dicamba-BAPMA and dicamba-methyl.

In another preferred embodiment of the present invention the at least one herbicide C of the herbicidal combination according to the invention is selected from the group of diclosulam, cloransulam, flumetsulam, thiencarbazone, nicosulfuron, rimsulfuron, chlorimuron, thifensulfuron, imazapyr, imazamox, imazaquin, imazapic, imazethapyr, flumioxazin, butafenacil, carfentrazone, sulfentrazone, acifluorfen, fomesafen, lactofen, oxyfluorfen, dicamba, 2,4-D, pendimethalin, fenoxaprop, haloxyfop, clethodim, sethoxydim, profoxydim, atrazine, metribuzin, bentazone, clomazone, isoxaflutole, mesotrione, tembotrione, bicyclopyrone, topramezone, dimethenamid, acetochlor, metolachlor, metazachlor, flufenacet and their agriculturally acceptable enantiomers, salts and esters. More preferably the at least one herbicide C is selected from the group of sulfentrazone, fomesafen, oxyfluorfen, flumioxazin, dimethenamid, acetochlor, pendimethalin, dicamba, imazamox, imazaquin, imazethapyr, atrazine, diclosulam, cloransulam, mesotrione, isoxaflutole, topramezone, clethodim, 2,4-D, flufenacet, fenoxaprop and their enantiomers, salts and esters, and particularly preferred from the group of fomesafen, flumioxazin, dimethenamid, acetochlor, pendimethalin, dicamba, imazamox, imazaquin, imazethapyr, atrazine, diclosulam, mesotrione, isoxaflutole, topramezone, clethodim, 2,4-D and their enantiomers, salts and esters.

In another preferred embodiment of the present invention the at least one herbicide C of the herbicidal combination according to the invention is selected from the group of diclosulam, cloransulam, cloransulam-ammonium, cloransulam-methyl, flumetsulam, thiencarbazone, thiencarbazone-methyl, nicosulfuron, rimsulfuron, chlorimuron, chlorimuron-ethyl, thifensulfuron, thifensulfuron-methyl, imazapyr, imazamox, imazaquin, imazapic, imazethapyr, flumioxazin, butafenacil, carfentrazone, carfentrazone-ethyl, sulfentrazone, acifluorfen, acifluorfen-sodium, acifluorfen-methyl, fomesafen, fomesafen-sodium, lactofen, oxyfluorfen, dicamba, dicamba-sodium, dicamba-potassium, dicamba-methylammonium, dicamba-isopropylammonium, dicamba-dimethylammonium, dicamba-diglycolammonium, dicamba-olamine, dicamba-diolamine, dicamba-trolamine, dicamba-BAPMA, dicamba-methyl, 2,4-D, 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-D-dodecylammonium, 2,4-D-ethyl, 2,4-D-2-ethylhexyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, pendimethalin, fenoxaprop, fenoxaprop-P, fenoxaprop-ethyl, fenoxaprop-P-ethyl, haloxyfop, haloxyfop-P, haloxyfop-sodium, haloxyfop-etotyl, haloxyfop-methyl, haloxyfop-P-etotyl, haloxyfop-P-methyl, clethodim, sethoxydim, profoxydim, atrazine, metribuzin, bentazone, bentazone-sodium, clomazone, isoxaflutole, mesotrione, tembotrione, bicyclopyrone, topramezone, dimethenamid, dimethenamid-P, acetochlor, metolachlor, S-metolachlor, metazachlor and flufenacet. More preferably the at least one herbicide C is selected from the group of sulfentrazone, fomesafen, fomesafen-sodium, oxyfluorfen, flumioxazin, dimethenamid, dimethenamid-P, acetochlor, pendimethalin, dicamba, dicamba-sodium, dicamba-potassium, dicamba-isopropylammonium, dicamba-dimethylammonium, dicamba-diglycolammonium, dicamba-BAPMA, dicamba-methyl, imazamox, imazaquin, imazethapyr, atrazine, diclosulam, cloransulam, mesotrione, isoxaflutole, topramezone, clethodim, 2,4-D, 2,4-D-sodium, 2,4-D-dimethylammonium, 2,4-D-2-ethylhexyl, flufenacet and fenoxaprop.

In a particular preferred embodiment of the of the present invention the at least one herbicide C of the herbicidal combination according to the invention is selected from the group of fomesafen, flumioxazin, dimethenamid, acetochlor, pendimethalin, dicamba, imazamox, imazaquin, imazethapyr, atrazine, diclosulam, mesotrione, isoxaflutole, topramezone, clethodim, 2,4-D and their enantiomers, salts and esters, such as in particular fomesafen-sodium, dimethenamid-P, dicamba-sodium, dicamba-potassium, dicamba-isopropylammonium, dicamba-dimethylammonium, dicamba-diglycolammonium, dicamba-BAPMA, dicamba-methyl, 2,4-D-sodium, 2,4-D-dimethylammonium and 2,4-D-2-ethylhexyl.

In another particular preferred embodiment of the invention the herbicidal combination comprises sulfentrazone as herbicide B and at least one herbicide C which is preferably selected from diclosulam, cloransulam, flumetsulam, thiencarbazone, nicosulfuron, rimsulfuron, chlorimuron, thifensulfuron, imazapyr, imazamox, imazaquin, imazapic, imazethapyr, flumioxazin, butafenacil, carfentrazone, acifluorfen, fomesafen, lactofen, oxyfluorfen, dicamba, 2,4-D, pendimethalin, fenoxaprop, haloxyfop, clethodim, sethoxydim, profoxydim, atrazine, metribuzin, bentazone, clomazone, isoxaflutole, mesotrione, tembotrione, bicyclopyrone, topramezone, dimethenamid, acetochlor, metolachlor, metazachlor, flufenacet and their agriculturally acceptable enantiomers, salts and esters, in particular the aforementioned specific enantiomers, salts and esters, especially those mentioned herein as preferred.

In another particular preferred embodiment of the invention the herbicidal combination comprises flumioxazin as herbicide B and at least one herbicide C which is preferably selected from diclosulam, cloransulam, flumetsulam, thiencarbazone, nicosulfuron, rimsulfuron, chlorimuron, thifensulfuron, imazapyr, imazamox, imazaquin, imazapic, imazethapyr, butafenacil, carfentrazone, sulfentrazone, acifluorfen, fomesafen, lactofen, oxyfluorfen, dicamba, 2,4-D-2-ethylhexyl, pendimethalin, fenoxaprop, haloxyfop, clethodim, sethoxydim, profoxydim, atrazine, metribuzin, bentazone, clomazone, isoxaflutole, mesotrione, tembotrione, bicyclopyrone, topramezone, dimethenamid, acetochlor, metolachlor, metazachlor, flufenacet and, with the exception of 2,4-D-2-ethylhexyl, their agriculturally acceptable enantiomers, salts and esters, in particular the aforementioned specific enantiomers, salts and esters, especially those mentioned herein as preferred.

In another particular preferred embodiment of the invention the herbicidal combination comprises dicamba or one of its aforementioned salts or esters, such as in particular dicamba-sodium, dicamba-potassium, dicamba-isopropylammonium, dicamba-dimethylammonium, dicamba-diglycolammonium, dicamba-BAPMA or dicamba-methyl, as herbicide B and at least one herbicide C which is preferably selected from diclosulam, cloransulam, flumetsulam, thiencarbazone, nicosulfuron, rimsulfuron, chlorimuron, thifensulfuron, imazamox, imazaquin, imazapic, imazethapyr, flumioxazin, butafenacil, carfentrazone, sulfentrazone, acifluorfen, fomesafen, lactofen, oxyfluorfen, 2,4-D, pendimethalin, fenoxaprop, haloxyfop, clethodim, sethoxydim, profoxydim, atrazine, metribuzin, bentazone, clomazone, isoxaflutole, mesotrione, tembotrione, bicyclopyrone, topramezone, dimethenamid, acetochlor, metolachlor, metazachlor, flufenacet and their agriculturally acceptable enantiomers, salts and esters, in particular the aforementioned specific enantiomers, salts and esters, especially those mentioned herein as preferred.

Examples of suitable herbicidal combinations of the invention that include herbicides A, B and C are listed in the following table 1. Also given in table 1 are the ranges for the weight ratios of herbicide A to herbicide C as well as of herbicide B to herbicides A+C for each listed combination.

TABLE 1

Each of the following herbicidal combinations of Nos. 1 to 60 includes, besides the listed herbicides B and C, saflufenacil as herbicide A.

| No. | Herbicide B* | Herbicide C* | A:C w/w | B:(A + C) w/w |
|---|---|---|---|---|
| 1 | sulfentrazone | flumioxazin | 1:500 to 100:1 | 150:1 to 1:400 |
| 2 | sulfentrazone | fomesafen | 1:500 to 100:1 | 150:1 to 1:400 |
| 3 | sulfentrazone | oxyfluorfen | 1:500 to 100:1 | 150:1 to 1:400 |
| 4 | sulfentrazone | dimethenamid | 1:500 to 100:1 | 150:1 to 1:400 |
| 5 | sulfentrazone | acetochlor | 1:500 to 100:1 | 150:1 to 1:400 |
| 6 | sulfentrazone | pendimethalin | 1:500 to 100:1 | 150:1 to 1:400 |
| 7 | sulfentrazone | dicamba | 1:500 to 100:1 | 150:1 to 1:400 |
| 8 | sulfentrazone | imazamox | 1:500 to 100:1 | 150:1 to 1:400 |
| 9 | sulfentrazone | imazaquin | 1:500 to 100:1 | 150:1 to 1:400 |

TABLE 1-continued

Each of the following herbicidal combinations of Nos. 1 to 60 includes, besides the listed herbicides B and C, saflufenacil as herbicide A.

| No. | Herbicide B* | Herbicide C* | A:C w/w | B:(A + C) w/w |
|---|---|---|---|---|
| 10 | sulfentrazone | imazethapyr | 1:500 to 100:1 | 150:1 to 1:400 |
| 11 | sulfentrazone | atrazine | 1:500 to 100:1 | 150:1 to 1:400 |
| 12 | sulfentrazone | diclosulam | 1:500 to 100:1 | 150:1 to 1:400 |
| 13 | sulfentrazone | cloransulam | 1:500 to 100:1 | 150:1 to 1:400 |
| 14 | sulfentrazone | mesotrione | 1:500 to 100:1 | 150:1 to 1:400 |
| 15 | sulfentrazone | isoxaflutole | 1:500 to 100:1 | 150:1 to 1:400 |
| 16 | sulfentrazone | topramezone | 1:500 to 100:1 | 150:1 to 1:400 |
| 17 | sulfentrazone | clethodim | 1:500 to 100:1 | 150:1 to 1:400 |
| 18 | sulfentrazone | 2,4-D | 1:500 to 100:1 | 150:1 to 1:400 |
| 19 | sulfentrazone | flufenacet | 1:500 to 100:1 | 150:1 to 1:400 |
| 20 | sulfentrazone | fenoxaprop | 1:500 to 100:1 | 150:1 to 1:400 |
| 21 | flumioxazin | sulfentrazone | 1:500 to 100:1 | 150:1 to 1:400 |
| 22 | flumioxazin | fomesafen | 1:500 to 100:1 | 150:1 to 1:400 |
| 23 | flumioxazin | oxyfluorfen | 1:500 to 100:1 | 150:1 to 1:400 |
| 24 | flumioxazin | dimethenamid | 1:500 to 100:1 | 150:1 to 1:400 |
| 25 | flumioxazin | acetochlor | 1:500 to 100:1 | 150:1 to 1:400 |
| 26 | flumioxazin | pendimethalin | 1:500 to 100:1 | 150:1 to 1:400 |
| 27 | flumioxazin | dicamba | 1:500 to 100:1 | 150:1 to 1:400 |
| 28 | flumioxazin | imazamox | 1:500 to 100:1 | 150:1 to 1:400 |
| 29 | flumioxazin | Imazaquin | 1:500 to 100:1 | 150:1 to 1:400 |
| 30 | flumioxazin | imazethapyr | 1:500 to 100:1 | 150:1 to 1:400 |
| 31 | flumioxazin | atrazine | 1:500 to 100:1 | 150:1 to 1:400 |
| 32 | flumioxazin | diclosulam | 1:500 to 100:1 | 150:1 to 1:400 |
| 33 | flumioxazin | cloransulam | 1:500 to 100:1 | 150:1 to 1:400 |
| 34 | flumioxazin | mesotrione | 1:500 to 100:1 | 150:1 to 1:400 |
| 35 | flumioxazin | isoxaflutole | 1:500 to 100:1 | 150:1 to 1:400 |
| 36 | flumioxazin | topramezone | 1:500 to 100:1 | 150:1 to 1:400 |
| 37 | flumioxazin | clethodim | 1:500 to 100:1 | 150:1 to 1:400 |
| 38 | flumioxazin | 2,4-D-2-ethylhexyl | 1:500 to 100:1 | 150:1 to 1:400 |
| 39 | flumioxazin | flufenacet | 1:500 to 100:1 | 150:1 to 1:400 |
| 40 | flumioxazin | fenoxaprop | 1:500 to 100:1 | 150:1 to 1:400 |
| 41 | dicamba | sulfentrazone | 1:500 to 100:1 | 150:1 to 1:400 |
| 42 | dicamba | flumioxazin | 1:500 to 100:1 | 150:1 to 1:400 |
| 43 | dicamba | fomesafen | 1:500 to 100:1 | 150:1 to 1:400 |
| 44 | dicamba | oxyfluorfen | 1:500 to 100:1 | 150:1 to 1:400 |
| 45 | dicamba | dimethenamid | 1:500 to 100:1 | 150:1 to 1:400 |
| 46 | dicamba | acetochlor | 1:500 to 100:1 | 150:1 to 1:400 |
| 47 | dicamba | pendimethalin | 1:500 to 100:1 | 150:1 to 1:400 |
| 48 | dicamba | imazamox | 1:500 to 100:1 | 150:1 to 1:400 |
| 49 | dicamba | imazaquin | 1:500 to 100:1 | 150:1 to 1:400 |
| 50 | dicamba | imazethapyr | 1:500 to 100:1 | 150:1 to 1:400 |
| 51 | dicamba | atrazine | 1:500 to 100:1 | 150:1 to 1:400 |
| 52 | dicamba | diclosulam | 1:500 to 100:1 | 150:1 to 1:400 |
| 53 | dicamba | cloransulam | 1:500 to 100:1 | 150:1 to 1:400 |
| 54 | dicamba | mesotrione | 1:500 to 100:1 | 150:1 to 1:400 |
| 55 | dicamba | isoxaflutole | 1:500 to 100:1 | 150:1 to 1:400 |
| 56 | dicamba | topramezone | 1:500 to 100:1 | 150:1 to 1:400 |
| 57 | dicamba | clethodim | 1:500 to 100:1 | 150:1 to 1:400 |
| 58 | dicamba | 2,4-D | 1:500 to 100:1 | 150:1 to 1:400 |
| 59 | dicamba | flufenacet | 1:500 to 100:1 | 150:1 to 1:400 |
| 60 | dicamba | fenoxaprop | 1:500 to 100:1 | 150:1 to 1:400 |

*may be applied in the form of its enantiomer, salt or ester, unless a specific enantiomer, salt or ester is mentioned.

Particularly preferred combinations of herbicides A, B and C according to the present invention are selected from the following combinations:
herbicide A, sulfentrazone and flumioxazin,
herbicide A, sulfentrazone and fomesafen,
herbicide A, sulfentrazone and dimethenamid,
herbicide A, sulfentrazone and acetochlor,
herbicide A, sulfentrazone and pendimethalin,
herbicide A, sulfentrazone and clethodim,
herbicide A, sulfentrazone and dicamba,
herbicide A, sulfentrazone and imazamox,
herbicide A, sulfentrazone and imazaquin,
herbicide A, sulfentrazone and imazethapyr,
herbicide A, sulfentrazone and atrazine,
herbicide A, sulfentrazone and diclosulam,
herbicide A, sulfentrazone and mesotrione,
herbicide A, sulfentrazone and isoxaflutole,
herbicide A, sulfentrazone and topramezone,
herbicide A, sulfentrazone and 2,4-D,
herbicide A, flumioxazin and fomesafen,
herbicide A, flumioxazin and dimethenamid,
herbicide A, flumioxazin and acetochlor,
herbicide A, flumioxazin and pendimethalin,
herbicide A, flumioxazin and clethodim,
herbicide A, flumioxazin and dicamba,
herbicide A, flumioxazin and imazamox,
herbicide A, flumioxazin and imazaquin,
herbicide A, flumioxazin and imazethapyr,
herbicide A, flumioxazin and atrazine,
herbicide A, flumioxazin and diclosulam,
herbicide A, flumioxazin and mesotrione,
herbicide A, flumioxazin and isoxaflutole,
herbicide A, flumioxazin and topramezone,
herbicide A, flumioxazin and the 2-ethylhexyl ester of 2,4-D,
herbicide A, dicamba and fomesafen,
herbicide A, dicamba and dimethenamid,
herbicide A, dicamba and acetochlor,
herbicide A, dicamba and pendimethalin,
herbicide A, dicamba and clethodim,
herbicide A, dicamba and imazamox,
herbicide A, dicamba and imazaquin,
herbicide A, dicamba and imazethapyr,
herbicide A, dicamba and atrazine,
herbicide A, dicamba and diclosulam,
herbicide A, dicamba and mesotrione,
herbicide A, dicamba and isoxaflutole,
herbicide A, dicamba and topramezone, and
herbicide A, dicamba and 2,4-D,
wherein dimethenamid, dicamba and 2,4-D in each case may optionally be present in the form of their respective enantiomers, salts or esters, in particular their aforementioned preferred enantiomers, salts or esters, unless a specific enantiomer, salt or ester is designated.

Even more preferred combinations of herbicides A, B and C according to the present invention are selected from the following combinations:
herbicide A, sulfentrazone and dimethenamid,
herbicide A, sulfentrazone and imazethapyr,
herbicide A, flumioxazin and dimethenamid,
herbicide A, flumioxazin and dicamba,
herbicide A, flumioxazin and imazamox,
herbicide A, flumioxazin and imazethapyr,
herbicide A, dicamba and dimethenamid, and
herbicide A, dicamba and imazethapyr,
wherein dimethenamid in each case may optionally be present in the form of one of its enantiomers, in particular dimethenamid-P, and dicamba may optionally be present in the form of one of its salts or esters, in particular dicamba-sodium, dicamba-potassium, dicamba-isopropylammonium, dicamba-dimethylammonium, dicamba-diglycolammonium, dicamba-BAPMA or dicamba-methyl.

In a ninth embodiment of the invention (embodiment 9), the herbicidal combinations of the invention comprise, as component d), at least one further herbicide D which is different from herbicides B and C, and which is selected from synthetic auxins, ACC inhibitors, photosystem II inhibitors, pigment synthesis inhibitors, VLCFA inhibitors, imidazolinone herbicides and dinitroaniline herbicides. Synthetic auxins, ACC inhibitors, photosystem II inhibitors, pigment synthesis inhibitors and VLCFA inhibitors that are suitable in this embodiment are those mentioned in this context of herbicides C.3, C.5, C.6, C.7 and C.8.

Preferred synthetic auxins in the context of the embodiment 9 include the aforementioned benzoic acid herbicides (herbicides C.3.1), such as e.g. dicamba, tricamba, chloramben and 2,3,6-TBA (2,3,6-trichlorobenzoic acid) and the salts and esters thereof.

In particular preferred herbicidal combinations of the embodiment 9 the at least one further herbicide D is at least one synthetic auxin selected from dicamba and its salts and esters, such as in particular dicamba-sodium.

Preferred ACC inhibitors in the context of the embodiment 9 include the aforementioned cyclohexanedione herbicides (herbicides C.5.2), such as e.g. alloxydim, butroxydim, clethodim, cloproxydim, cycloxydim, profoxydim, sethoxydim, tepraloxydim, tralkoxydim and their salts, such as alloxydim-sodium.

In particular preferred herbicidal combinations of the embodiment 9 the at least one further herbicide D is at least one ACC inhibitor which is clethodim.

Preferred photosystem II inhibitors in the context of the embodiment 9 include the aforementioned triazine herbicides (herbicides C.6.3), such as e.g. atrazine, chlorazine, cyanazine, cyprazine, eglinazine, ipazine, mesoprazine, procyazine, proglinazine, propazine, sebuthylazine, simazine, terbuthylazine, trietazine and their salts and esters, such as eglinazine-ethyl and proglinazine-ethyl.

In particular preferred herbicidal combinations of the embodiment 9 the at least one further herbicide D is at least one photosystem II inhibitor which is selected from atrazine, terbuthylazine and simazine, and in particular is atrazine.

Preferred pigment synthesis inhibitors in the context of the embodiment 9 include the aforementioned DOXP synthase inhibitors (herbicides C.7.4), such as e.g. clomazone, and the benzoylcyclohexanedione herbicides (herbicides C.7.2.2), such as fenquinotrione, ketospiradox, mesotrione, sulcotrione, tefuryltrione and tembotrione.

In particular preferred herbicidal herbicidal combinations of the embodiment 9 the at least one further herbicide D is at least one pigment synthesis inhibitor selected from clomazone, mesotrione and tembotrione.

Preferred VLCFA inhibitors in the context of the embodiment 9 include the aforementioned chloroacetamide herbicides (herbicides C.8.1), such as e.g. acetochlor, alachlor, butachlor, dimethachlor, dimethenamid, dimethenamid-P, metazachlor, metolachlor, S-metolachlor, pethoxamid, pretilachlor, propachlor, propisochlor and thenylchlor.

In particular preferred herbicidal herbicidal combinations of the embodiment 9 the at least one further herbicide D is at least one VLCFA inhibitor selected from dimethenamid, dimethenamid-P and acetochlor.

In the context of the embodiment 9 imidazolinone herbicides are those that are described above as herbicides C.1.5, e.g. imazamethabenz, imazamox, imazapic, imazapyr, imazaquin and imazethapyr, and the esters thereof such as imazamethabenz-methyl.

In particular preferred herbicidal combinations of the embodiment 9 the at least one further herbicide D is at least one imidazolinone herbicide selected from imazethapyr, imazamox, imazapyr and imazapic.

In the context of the embodiment 9 dinitroaniline herbicides are those that are described above as herbicides C.4.1, e.g. benfluralin, butralin, chlornidine, dinitramine, dipropalin, ethalfluralin, fluchloralin, isopropalin, methalpropalin, nitralin, oryzalin, pendimethalin, prodiamine, profluralin and trifluralin.

In particular preferred herbicidal herbicidal combinations of the embodiment 9 the at least one further herbicide D is at least one dinitroaniline herbicide which is pendimethalin.

In the combinations of the embodiment 9 the relative weight ratio of saflufenacil (herbicide A) to herbicide D is preferably in the range from 1:1000 to 50:1, more preferably in the range from 1:500 to 20:1, in particular from 1:200 to 10:1, specifically from 1:100 to 5:1 and particularly preferred from 1:50 to 3:1. The relative weight ratio of herbicide B to herbicides A+C+D is preferably in the range from 150:1 to 1:1100, more preferably from 100:1 to 1:550, in particular from 75:1 to 1:440, specifically from 50:1 to 1:160 and particularly preferred from 20:1 to 1:50.

Examples of suitable herbicidal combinations of the invention that include herbicides A, B, C and D are listed in the following table 2. Also given in table 2 are the ranges for the weight ratios of herbicide A to herbicide C as well as of herbicide B to herbicides (A+C+D) for each listed combination.

TABLE 2

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 1 | sulfentrazone | flumioxazin | dicamba | 1:500-100:1 | 100:1-1:550 |
| 2 | sulfentrazone | fomesafen | dicamba | 1:500-100:1 | 100:1-1:550 |
| 3 | sulfentrazone | dimethenamid | dicamba | 1:500-100:1 | 100:1-1:550 |
| 4 | sulfentrazone | acetochlor | dicamba | 1:500-100:1 | 100:1-1:550 |
| 5 | sulfentrazone | pendimethalin | dicamba | 1:500-100:1 | 100:1-1:550 |
| 6 | sulfentrazone | clethodim | dicamba | 1:500-100:1 | 100:1-1:550 |
| 7 | sulfentrazone | imazamox | dicamba | 1:500-100:1 | 100:1-1:550 |
| 8 | sulfentrazone | imazaquin | dicamba | 1:500-100:1 | 100:1-1:550 |
| 9 | sulfentrazone | imazethapyr | dicamba | 1:500-100:1 | 100:1-1:550 |
| 10 | sulfentrazone | atrazine | dicamba | 1:500-100:1 | 100:1-1:550 |
| 11 | sulfentrazone | diclosulam | dicamba | 1:500-100:1 | 100:1-1:550 |
| 12 | sulfentrazone | mesotrione | dicamba | 1:500-100:1 | 100:1-1:550 |
| 13 | sulfentrazone | isoxaflutole | dicamba | 1:500-100:1 | 100:1-1:550 |
| 14 | sulfentrazone | topramezone | dicamba | 1:500-100:1 | 100:1-1:550 |
| 15 | sulfentrazone | 2,4-D | dicamba | 1:500-100:1 | 100:1-1:550 |
| 16 | flumioxazin | fomesafen | dicamba | 1:500-100:1 | 100:1-1:550 |
| 17 | flumioxazin | clethodim | dicamba | 1:500-100:1 | 100:1-1:550 |
| 18 | flumioxazin | imazaquin | dicamba | 1:500-100:1 | 100:1-1:550 |
| 19 | flumioxazin | dimethenamid | dicamba | 1:500-100:1 | 100:1-1:550 |
| 20 | flumioxazin | acetochlor | dicamba | 1:500-100:1 | 100:1-1:550 |
| 21 | flumioxazin | pendimethalin | dicamba | 1:500-100:1 | 100:1-1:550 |
| 22 | flumioxazin | imazamox | dicamba | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 23 | flumioxazin | imazethapyr | dicamba | 1:500-100:1 | 100:1-1:550 |
| 24 | flumioxazin | atrazine | dicamba | 1:500-100:1 | 100:1-1:550 |
| 25 | flumioxazin | diclosulam | dicamba | 1:500-100:1 | 100:1-1:550 |
| 26 | flumioxazin | mesotrione | dicamba | 1:500-100:1 | 100:1-1:550 |
| 27 | flumioxazin | isoxaflutole | dicamba | 1:500-100:1 | 100:1-1:550 |
| 28 | flumioxazin | topramezone | dicamba | 1:500-100:1 | 100:1-1:550 |
| 29 | flumioxazin | 2,4-D-2-ethylhexyl | dicamba | 1:500-100:1 | 100:1-1:550 |
| 30 | sulfentrazone | flumioxazin | clethodim | 1:500-100:1 | 100:1-1:550 |
| 31 | sulfentrazone | fomesafen | clethodim | 1:500-100:1 | 100:1-1:550 |
| 32 | sulfentrazone | dimethenamid | clethodim | 1:500-100:1 | 100:1-1:550 |
| 33 | sulfentrazone | acetochlor | clethodim | 1:500-100:1 | 100:1-1:550 |
| 34 | sulfentrazone | pendimethalin | clethodim | 1:500-100:1 | 100:1-1:550 |
| 35 | sulfentrazone | dicamba | clethodim | 1:500-100:1 | 100:1-1:550 |
| 36 | sulfentrazone | imazamox | clethodim | 1:500-100:1 | 100:1-1:550 |
| 37 | sulfentrazone | imazaquin | clethodim | 1:500-100:1 | 100:1-1:550 |
| 38 | sulfentrazone | imazethapyr | clethodim | 1:500-100:1 | 100:1-1:550 |
| 39 | sulfentrazone | atrazine | clethodim | 1:500-100:1 | 100:1-1:550 |
| 40 | sulfentrazone | diclosulam | clethodim | 1:500-100:1 | 100:1-1:550 |
| 41 | sulfentrazone | mesotrione | clethodim | 1:500-100:1 | 100:1-1:550 |
| 42 | sulfentrazone | isoxaflutole | clethodim | 1:500-100:1 | 100:1-1:550 |
| 43 | sulfentrazone | topramezone | clethodim | 1:500-100:1 | 100:1-1:550 |
| 44 | sulfentrazone | 2,4-D | clethodim | 1:500-100:1 | 100:1-1:550 |
| 45 | flumioxazin | fomesafen | clethodim | 1:500-100:1 | 100:1-1:550 |
| 46 | flumioxazin | clethodim | clethodim | 1:500-100:1 | 100:1-1:550 |
| 47 | flumioxazin | imazaquin | clethodim | 1:500-100:1 | 100:1-1:550 |
| 48 | flumioxazin | dimethenamid | clethodim | 1:500-100:1 | 100:1-1:550 |
| 49 | flumioxazin | acetochlor | clethodim | 1:500-100:1 | 100:1-1:550 |
| 50 | flumioxazin | pendimethalin | clethodim | 1:500-100:1 | 100:1-1:550 |
| 51 | flumioxazin | dicamba | clethodim | 1:500-100:1 | 100:1-1:550 |
| 52 | flumioxazin | imazamox | clethodim | 1:500-100:1 | 100:1-1:550 |
| 53 | flumioxazin | imazethapyr | clethodim | 1:500-100:1 | 100:1-1:550 |
| 54 | flumioxazin | atrazine | clethodim | 1:500-100:1 | 100:1-1:550 |
| 55 | flumioxazin | diclosulam | clethodim | 1:500-100:1 | 100:1-1:550 |
| 56 | flumioxazin | mesotrione | clethodim | 1:500-100:1 | 100:1-1:550 |
| 57 | flumioxazin | isoxaflutole | clethodim | 1:500-100:1 | 100:1-1:550 |
| 58 | flumioxazin | topramezone | clethodim | 1:500-100:1 | 100:1-1:550 |
| 59 | flumioxazin | 2,4-D-2-ethylhexyl | clethodim | 1:500-100:1 | 100:1-1:550 |
| 60 | dicamba | fomesafen | clethodim | 1:500-100:1 | 100:1-1:550 |
| 61 | dicamba | clethodim | clethodim | 1:500-100:1 | 100:1-1:550 |
| 62 | dicamba | imazaquin | clethodim | 1:500-100:1 | 100:1-1:550 |
| 63 | dicamba | dimethenamid | clethodim | 1:500-100:1 | 100:1-1:550 |
| 64 | dicamba | acetochlor | clethodim | 1:500-100:1 | 100:1-1:550 |
| 65 | dicamba | pendimethalin | clethodim | 1:500-100:1 | 100:1-1:550 |
| 66 | dicamba | imazamox | clethodim | 1:500-100:1 | 100:1-1:550 |
| 67 | dicamba | imazethapyr | clethodim | 1:500-100:1 | 100:1-1:550 |
| 68 | dicamba | atrazine | clethodim | 1:500-100:1 | 100:1-1:550 |
| 69 | dicamba | diclosulam | clethodim | 1:500-100:1 | 100:1-1:550 |
| 70 | dicamba | mesotrione | clethodim | 1:500-100:1 | 100:1-1:550 |
| 71 | dicamba | isoxaflutole | clethodim | 1:500-100:1 | 100:1-1:550 |
| 72 | dicamba | topramezone | clethodim | 1:500-100:1 | 100:1-1:550 |
| 73 | sulfentrazone | flumioxazin | atrazine | 1:500-100:1 | 100:1-1:550 |
| 74 | sulfentrazone | fomesafen | atrazine | 1:500-100:1 | 100:1-1:550 |
| 75 | sulfentrazone | dimethenamid | atrazine | 1:500-100:1 | 100:1-1:550 |
| 76 | sulfentrazone | acetochlor | atrazine | 1:500-100:1 | 100:1-1:550 |
| 77 | sulfentrazone | pendimethalin | atrazine | 1:500-100:1 | 100:1-1:550 |
| 78 | sulfentrazone | clethodim | atrazine | 1:500-100:1 | 100:1-1:550 |
| 79 | sulfentrazone | dicamba | atrazine | 1:500-100:1 | 100:1-1:550 |
| 80 | sulfentrazone | imazamox | atrazine | 1:500-100:1 | 100:1-1:550 |
| 81 | sulfentrazone | imazaquin | atrazine | 1:500-100:1 | 100:1-1:550 |
| 82 | sulfentrazone | imazethapyr | atrazine | 1:500-100:1 | 100:1-1:550 |
| 83 | sulfentrazone | diclosulam | atrazine | 1:500-100:1 | 100:1-1:550 |
| 84 | sulfentrazone | mesotrione | atrazine | 1:500-100:1 | 100:1-1:550 |
| 85 | sulfentrazone | isoxaflutole | atrazine | 1:500-100:1 | 100:1-1:550 |
| 86 | sulfentrazone | topramezone | atrazine | 1:500-100:1 | 100:1-1:550 |
| 87 | sulfentrazone | 2,4-D | atrazine | 1:500-100:1 | 100:1-1:550 |
| 88 | flumioxazin | fomesafen | atrazine | 1:500-100:1 | 100:1-1:550 |
| 89 | flumioxazin | clethodim | atrazine | 1:500-100:1 | 100:1-1:550 |
| 90 | flumioxazin | imazaquin | atrazine | 1:500-100:1 | 100:1-1:550 |
| 91 | flumioxazin | dimethenamid | atrazine | 1:500-100:1 | 100:1-1:550 |
| 92 | flumioxazin | acetochlor | atrazine | 1:500-100:1 | 100:1-1:550 |
| 93 | flumioxazin | pendimethalin | atrazine | 1:500-100:1 | 100:1-1:550 |
| 94 | flumioxazin | dicamba | atrazine | 1:500-100:1 | 100:1-1:550 |
| 95 | flumioxazin | imazamox | atrazine | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 96 | flumioxazin | imazethapyr | atrazine | 1:500-100:1 | 100:1-1:550 |
| 97 | flumioxazin | diclosulam | atrazine | 1:500-100:1 | 100:1-1:550 |
| 98 | flumioxazin | mesotrione | atrazine | 1:500-100:1 | 100:1-1:550 |
| 99 | flumioxazin | isoxaflutole | atrazine | 1:500-100:1 | 100:1-1:550 |
| 100 | flumioxazin | topramezone | atrazine | 1:500-100:1 | 100:1-1:550 |
| 101 | flumioxazin | 2,4-D-2-ethylhexyl | atrazine | 1:500-100:1 | 100:1-1:550 |
| 102 | dicamba | fomesafen | atrazine | 1:500-100:1 | 100:1-1:550 |
| 103 | dicamba | clethodim | atrazine | 1:500-100:1 | 100:1-1:550 |
| 104 | dicamba | imazaquin | atrazine | 1:500-100:1 | 100:1-1:550 |
| 105 | dicamba | dimethenamid | atrazine | 1:500-100:1 | 100:1-1:550 |
| 106 | dicamba | acetochlor | atrazine | 1:500-100:1 | 100:1-1:550 |
| 107 | dicamba | pendimethalin | atrazine | 1:500-100:1 | 100:1-1:550 |
| 108 | dicamba | imazamox | atrazine | 1:500-100:1 | 100:1-1:550 |
| 109 | dicamba | imazethapyr | atrazine | 1:500-100:1 | 100:1-1:550 |
| 110 | dicamba | diclosulam | atrazine | 1:500-100:1 | 100:1-1:550 |
| 111 | dicamba | mesotrione | atrazine | 1:500-100:1 | 100:1-1:550 |
| 112 | dicamba | isoxaflutole | atrazine | 1:500-100:1 | 100:1-1:550 |
| 113 | dicamba | topramezone | atrazine | 1:500-100:1 | 100:1-1:550 |
| 114 | sulfentrazone | flumioxazin | clomazone | 1:500-100:1 | 100:1-1:550 |
| 115 | sulfentrazone | fomesafen | clomazone | 1:500-100:1 | 100:1-1:550 |
| 116 | sulfentrazone | dimethenamid | clomazone | 1:500-100:1 | 100:1-1:550 |
| 117 | sulfentrazone | acetochlor | clomazone | 1:500-100:1 | 100:1-1:550 |
| 118 | sulfentrazone | pendimethalin | clomazone | 1:500-100:1 | 100:1-1:550 |
| 119 | sulfentrazone | clethodim | clomazone | 1:500-100:1 | 100:1-1:550 |
| 120 | sulfentrazone | dicamba | clomazone | 1:500-100:1 | 100:1-1:550 |
| 121 | sulfentrazone | imazamox | clomazone | 1:500-100:1 | 100:1-1:550 |
| 122 | sulfentrazone | imazaquin | clomazone | 1:500-100:1 | 100:1-1:550 |
| 123 | sulfentrazone | imazethapyr | clomazone | 1:500-100:1 | 100:1-1:550 |
| 124 | sulfentrazone | atrazine | clomazone | 1:500-100:1 | 100:1-1:550 |
| 125 | sulfentrazone | diclosulam | clomazone | 1:500-100:1 | 100:1-1:550 |
| 126 | sulfentrazone | mesotrione | clomazone | 1:500-100:1 | 100:1-1:550 |
| 127 | sulfentrazone | isoxaflutole | clomazone | 1:500-100:1 | 100:1-1:550 |
| 128 | sulfentrazone | topramezone | clomazone | 1:500-100:1 | 100:1-1:550 |
| 129 | sulfentrazone | 2,4-D | clomazone | 1:500-100:1 | 100:1-1:550 |
| 130 | flumioxazin | fomesafen | clomazone | 1:500-100:1 | 100:1-1:550 |
| 131 | flumioxazin | clethodim | clomazone | 1:500-100:1 | 100:1-1:550 |
| 132 | flumioxazin | imazaquin | clomazone | 1:500-100:1 | 100:1-1:550 |
| 133 | flumioxazin | dimethenamid | clomazone | 1:500-100:1 | 100:1-1:550 |
| 134 | flumioxazin | acetochlor | clomazone | 1:500-100:1 | 100:1-1:550 |
| 135 | flumioxazin | pendimethalin | clomazone | 1:500-100:1 | 100:1-1:550 |
| 136 | flumioxazin | dicamba | clomazone | 1:500-100:1 | 100:1-1:550 |
| 137 | flumioxazin | imazamox | clomazone | 1:500-100:1 | 100:1-1:550 |
| 138 | flumioxazin | imazethapyr | clomazone | 1:500-100:1 | 100:1-1:550 |
| 139 | flumioxazin | atrazine | clomazone | 1:500-100:1 | 100:1-1:550 |
| 140 | flumioxazin | diclosulam | clomazone | 1:500-100:1 | 100:1-1:550 |
| 141 | flumioxazin | mesotrione | clomazone | 1:500-100:1 | 100:1-1:550 |
| 142 | flumioxazin | isoxaflutole | clomazone | 1:500-100:1 | 100:1-1:550 |
| 143 | flumioxazin | topramezone | clomazone | 1:500-100:1 | 100:1-1:550 |
| 144 | flumioxazin | 2,4-D-2-ethylhexyl | clomazone | 1:500-100:1 | 100:1-1:550 |
| 145 | dicamba | fomesafen | clomazone | 1:500-100:1 | 100:1-1:550 |
| 146 | dicamba | clethodim | clomazone | 1:500-100:1 | 100:1-1:550 |
| 147 | dicamba | imazaquin | clomazone | 1:500-100:1 | 100:1-1:550 |
| 148 | dicamba | dimethenamid | clomazone | 1:500-100:1 | 100:1-1:550 |
| 149 | dicamba | acetochlor | clomazone | 1:500-100:1 | 100:1-1:550 |
| 150 | dicamba | pendimethalin | clomazone | 1:500-100:1 | 100:1-1:550 |
| 151 | dicamba | imazamox | clomazone | 1:500-100:1 | 100:1-1:550 |
| 152 | dicamba | imazethapyr | clomazone | 1:500-100:1 | 100:1-1:550 |
| 153 | dicamba | atrazine | clomazone | 1:500-100:1 | 100:1-1:550 |
| 154 | dicamba | diclosulam | clomazone | 1:500-100:1 | 100:1-1:550 |
| 155 | dicamba | mesotrione | clomazone | 1:500-100:1 | 100:1-1:550 |
| 156 | dicamba | isoxaflutole | clomazone | 1:500-100:1 | 100:1-1:550 |
| 157 | dicamba | topramezone | clomazone | 1:500-100:1 | 100:1-1:550 |
| 158 | sulfentrazone | flumioxazin | mesotrione | 1:500-100:1 | 100:1-1:550 |
| 159 | sulfentrazone | fomesafen | mesotrione | 1:500-100:1 | 100:1-1:550 |
| 160 | sulfentrazone | dimethenamid | mesotrione | 1:500-100:1 | 100:1-1:550 |
| 161 | sulfentrazone | acetochlor | mesotrione | 1:500-100:1 | 100:1-1:550 |
| 162 | sulfentrazone | pendimethalin | mesotrione | 1:500-100:1 | 100:1-1:550 |
| 163 | sulfentrazone | clethodim | mesotrione | 1:500-100:1 | 100:1-1:550 |
| 164 | sulfentrazone | dicamba | mesotrione | 1:500-100:1 | 100:1-1:550 |
| 165 | sulfentrazone | imazamox | mesotrione | 1:500-100:1 | 100:1-1:550 |
| 166 | sulfentrazone | imazaquin | mesotrione | 1:500-100:1 | 100:1-1:550 |
| 167 | sulfentrazone | imazethapyr | mesotrione | 1:500-100:1 | 100:1-1:550 |
| 168 | sulfentrazone | atrazine | mesotrione | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 169 | sulfentrazone | diclosulam | mesotrione | 1:500-100:1 | 100:1-1:550 |
| 170 | sulfentrazone | isoxaflutole | mesotrione | 1:500-100:1 | 100:1-1:550 |
| 171 | sulfentrazone | topramezone | mesotrione | 1:500-100:1 | 100:1-1:550 |
| 172 | sulfentrazone | 2,4-D | mesotrione | 1:500-100:1 | 100:1-1:550 |
| 173 | flumioxazin | fomesafen | mesotrione | 1:500-100:1 | 100:1-1:550 |
| 174 | flumioxazin | clethodim | mesotrione | 1:500-100:1 | 100:1-1:550 |
| 175 | flumioxazin | imazaquin | mesotrione | 1:500-100:1 | 100:1-1:550 |
| 176 | flumioxazin | dimethenamid | mesotrione | 1:500-100:1 | 100:1-1:550 |
| 177 | flumioxazin | acetochlor | mesotrione | 1:500-100:1 | 100:1-1:550 |
| 178 | flumioxazin | pendimethalin | mesotrione | 1:500-100:1 | 100:1-1:550 |
| 179 | flumioxazin | dicamba | mesotrione | 1:500-100:1 | 100:1-1:550 |
| 180 | flumioxazin | imazamox | mesotrione | 1:500-100:1 | 100:1-1:550 |
| 181 | flumioxazin | imazethapyr | mesotrione | 1:500-100:1 | 100:1-1:550 |
| 182 | flumioxazin | atrazine | mesotrione | 1:500-100:1 | 100:1-1:550 |
| 183 | flumioxazin | diclosulam | mesotrione | 1:500-100:1 | 100:1-1:550 |
| 184 | flumioxazin | isoxaflutole | mesotrione | 1:500-100:1 | 100:1-1:550 |
| 185 | flumioxazin | topramezone | mesotrione | 1:500-100:1 | 100:1-1:550 |
| 186 | flumioxazin | 2,4-D-2-ethylhexyl | mesotrione | 1:500-100:1 | 100:1-1:550 |
| 187 | dicamba | fomesafen | mesotrione | 1:500-100:1 | 100:1-1:550 |
| 188 | dicamba | clethodim | mesotrione | 1:500-100:1 | 100:1-1:550 |
| 189 | dicamba | imazaquin | mesotrione | 1:500-100:1 | 100:1-1:550 |
| 190 | dicamba | dimethenamid | mesotrione | 1:500-100:1 | 100:1-1:550 |
| 191 | dicamba | acetochlor | mesotrione | 1:500-100:1 | 100:1-1:550 |
| 192 | dicamba | pendimethalin | mesotrione | 1:500-100:1 | 100:1-1:550 |
| 193 | dicamba | imazamox | mesotrione | 1:500-100:1 | 100:1-1:550 |
| 194 | dicamba | imazethapyr | mesotrione | 1:500-100:1 | 100:1-1:550 |
| 195 | dicamba | atrazine | mesotrione | 1:500-100:1 | 100:1-1:550 |
| 196 | dicamba | diclosulam | mesotrione | 1:500-100:1 | 100:1-1:550 |
| 197 | dicamba | isoxaflutole | mesotrione | 1:500-100:1 | 100:1-1:550 |
| 198 | dicamba | topramezone | mesotrione | 1:500-100:1 | 100:1-1:550 |
| 199 | sulfentrazone | flumioxazin | tembotrione | 1:500-100:1 | 100:1-1:550 |
| 200 | sulfentrazone | fomesafen | tembotrione | 1:500-100:1 | 100:1-1:550 |
| 201 | sulfentrazone | dimethenamid | tembotrione | 1:500-100:1 | 100:1-1:550 |
| 202 | sulfentrazone | acetochlor | tembotrione | 1:500-100:1 | 100:1-1:550 |
| 203 | sulfentrazone | pendimethalin | tembotrione | 1:500-100:1 | 100:1-1:550 |
| 204 | sulfentrazone | clethodim | tembotrione | 1:500-100:1 | 100:1-1:550 |
| 205 | sulfentrazone | dicamba | tembotrione | 1:500-100:1 | 100:1-1:550 |
| 206 | sulfentrazone | imazamox | tembotrione | 1:500-100:1 | 100:1-1:550 |
| 207 | sulfentrazone | imazaquin | tembotrione | 1:500-100:1 | 100:1-1:550 |
| 208 | sulfentrazone | imazethapyr | tembotrione | 1:500-100:1 | 100:1-1:550 |
| 209 | sulfentrazone | atrazine | tembotrione | 1:500-100:1 | 100:1-1:550 |
| 210 | sulfentrazone | diclosulam | tembotrione | 1:500-100:1 | 100:1-1:550 |
| 211 | sulfentrazone | mesotrione | tembotrione | 1:500-100:1 | 100:1-1:550 |
| 212 | sulfentrazone | isoxaflutole | tembotrione | 1:500-100:1 | 100:1-1:550 |
| 213 | sulfentrazone | topramezone | tembotrione | 1:500-100:1 | 100:1-1:550 |
| 214 | sulfentrazone | 2,4-D | tembotrione | 1:500-100:1 | 100:1-1:550 |
| 215 | flumioxazin | fomesafen | tembotrione | 1:500-100:1 | 100:1-1:550 |
| 216 | flumioxazin | clethodim | tembotrione | 1:500-100:1 | 100:1-1:550 |
| 217 | flumioxazin | imazaquin | tembotrione | 1:500-100:1 | 100:1-1:550 |
| 218 | flumioxazin | dimethenamid | tembotrione | 1:500-100:1 | 100:1-1:550 |
| 219 | flumioxazin | acetochlor | tembotrione | 1:500-100:1 | 100:1-1:550 |
| 220 | flumioxazin | pendimethalin | tembotrione | 1:500-100:1 | 100:1-1:550 |
| 221 | flumioxazin | dicamba | tembotrione | 1:500-100:1 | 100:1-1:550 |
| 222 | flumioxazin | imazamox | tembotrione | 1:500-100:1 | 100:1-1:550 |
| 223 | flumioxazin | imazethapyr | tembotrione | 1:500-100:1 | 100:1-1:550 |
| 224 | flumioxazin | atrazine | tembotrione | 1:500-100:1 | 100:1-1:550 |
| 225 | flumioxazin | diclosulam | tembotrione | 1:500-100:1 | 100:1-1:550 |
| 226 | flumioxazin | mesotrione | tembotrione | 1:500-100:1 | 100:1-1:550 |
| 227 | flumioxazin | isoxaflutole | tembotrione | 1:500-100:1 | 100:1-1:550 |
| 228 | flumioxazin | topramezone | tembotrione | 1:500-100:1 | 100:1-1:550 |
| 229 | flumioxazin | 2,4-D-2-ethylhexyl | tembotrione | 1:500-100:1 | 100:1-1:550 |
| 230 | dicamba | fomesafen | tembotrione | 1:500-100:1 | 100:1-1:550 |
| 231 | dicamba | clethodim | tembotrione | 1:500-100:1 | 100:1-1:550 |
| 232 | dicamba | imazaquin | tembotrione | 1:500-100:1 | 100:1-1:550 |
| 233 | dicamba | dimethenamid | tembotrione | 1:500-100:1 | 100:1-1:550 |
| 234 | dicamba | acetochlor | tembotrione | 1:500-100:1 | 100:1-1:550 |
| 235 | dicamba | pendimethalin | tembotrione | 1:500-100:1 | 100:1-1:550 |
| 236 | dicamba | imazamox | tembotrione | 1:500-100:1 | 100:1-1:550 |
| 237 | dicamba | imazethapyr | tembotrione | 1:500-100:1 | 100:1-1:550 |
| 238 | dicamba | atrazine | tembotrione | 1:500-100:1 | 100:1-1:550 |
| 239 | dicamba | diclosulam | tembotrione | 1:500-100:1 | 100:1-1:550 |
| 240 | dicamba | mesotrione | tembotrione | 1:500-100:1 | 100:1-1:550 |
| 241 | dicamba | isoxaflutole | tembotrione | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 242 | dicamba | topramezone | tembotrione | 1:500-100:1 | 100:1-1:550 |
| 243 | sulfentrazone | flumioxazin | dimethenamid | 1:500-100:1 | 100:1-1:550 |
| 244 | sulfentrazone | fomesafen | dimethenamid | 1:500-100:1 | 100:1-1:550 |
| 245 | sulfentrazone | dimethenamid | dimethenamid | 1:500-100:1 | 100:1-1:550 |
| 246 | sulfentrazone | acetochlor | dimethenamid | 1:500-100:1 | 100:1-1:550 |
| 247 | sulfentrazone | pendimethalin | dimethenamid | 1:500-100:1 | 100:1-1:550 |
| 248 | sulfentrazone | clethodim | dimethenamid | 1:500-100:1 | 100:1-1:550 |
| 249 | sulfentrazone | dicamba | dimethenamid | 1:500-100:1 | 100:1-1:550 |
| 250 | sulfentrazone | imazamox | dimethenamid | 1:500-100:1 | 100:1-1:550 |
| 251 | sulfentrazone | imazaquin | dimethenamid | 1:500-100:1 | 100:1-1:550 |
| 252 | sulfentrazone | imazethapyr | dimethenamid | 1:500-100:1 | 100:1-1:550 |
| 253 | sulfentrazone | atrazine | dimethenamid | 1:500-100:1 | 100:1-1:550 |
| 254 | sulfentrazone | diclosulam | dimethenamid | 1:500-100:1 | 100:1-1:550 |
| 255 | sulfentrazone | mesotrione | dimethenamid | 1:500-100:1 | 100:1-1:550 |
| 256 | sulfentrazone | isoxaflutole | dimethenamid | 1:500-100:1 | 100:1-1:550 |
| 257 | sulfentrazone | topramezone | dimethenamid | 1:500-100:1 | 100:1-1:550 |
| 258 | sulfentrazone | 2,4-D | dimethenamid | 1:500-100:1 | 100:1-1:550 |
| 259 | flumioxazin | fomesafen | dimethenamid | 1:500-100:1 | 100:1-1:550 |
| 260 | flumioxazin | clethodim | dimethenamid | 1:500-100:1 | 100:1-1:550 |
| 261 | flumioxazin | imazaquin | dimethenamid | 1:500-100:1 | 100:1-1:550 |
| 262 | flumioxazin | dimethenamid | dimethenamid | 1:500-100:1 | 100:1-1:550 |
| 263 | flumioxazin | acetochlor | dimethenamid | 1:500-100:1 | 100:1-1:550 |
| 264 | flumioxazin | pendimethalin | dimethenamid | 1:500-100:1 | 100:1-1:550 |
| 265 | flumioxazin | dicamba | dimethenamid | 1:500-100:1 | 100:1-1:550 |
| 266 | flumioxazin | imazamox | dimethenamid | 1:500-100:1 | 100:1-1:550 |
| 267 | flumioxazin | imazethapyr | dimethenamid | 1:500-100:1 | 100:1-1:550 |
| 268 | flumioxazin | atrazine | dimethenamid | 1:500-100:1 | 100:1-1:550 |
| 269 | flumioxazin | diclosulam | dimethenamid | 1:500-100:1 | 100:1-1:550 |
| 270 | flumioxazin | mesotrione | dimethenamid | 1:500-100:1 | 100:1-1:550 |
| 271 | flumioxazin | isoxaflutole | dimethenamid | 1:500-100:1 | 100:1-1:550 |
| 272 | flumioxazin | topramezone | dimethenamid | 1:500-100:1 | 100:1-1:550 |
| 273 | flumioxazin | 2,4-D-2-ethylhexyl | dimethenamid | 1:500-100:1 | 100:1-1:550 |
| 274 | dicamba | fomesafen | dimethenamid | 1:500-100:1 | 100:1-1:550 |
| 275 | dicamba | clethodim | dimethenamid | 1:500-100:1 | 100:1-1:550 |
| 276 | dicamba | imazaquin | dimethenamid | 1:500-100:1 | 100:1-1:550 |
| 277 | dicamba | dimethenamid | dimethenamid | 1:500-100:1 | 100:1-1:550 |
| 278 | dicamba | acetochlor | dimethenamid | 1:500-100:1 | 100:1-1:550 |
| 279 | dicamba | pendimethalin | dimethenamid | 1:500-100:1 | 100:1-1:550 |
| 280 | dicamba | imazamox | dimethenamid | 1:500-100:1 | 100:1-1:550 |
| 281 | dicamba | imazethapyr | dimethenamid | 1:500-100:1 | 100:1-1:550 |
| 282 | dicamba | atrazine | dimethenamid | 1:500-100:1 | 100:1-1:550 |
| 283 | dicamba | diclosulam | dimethenamid | 1:500-100:1 | 100:1-1:550 |
| 284 | dicamba | mesotrione | dimethenamid | 1:500-100:1 | 100:1-1:550 |
| 285 | dicamba | isoxaflutole | dimethenamid | 1:500-100:1 | 100:1-1:550 |
| 286 | dicamba | topramezone | dimethenamid | 1:500-100:1 | 100:1-1:550 |
| 287 | sulfentrazone | flumioxazin | acetochlor | 1:500-100:1 | 100:1-1:550 |
| 288 | sulfentrazone | fomesafen | acetochlor | 1:500-100:1 | 100:1-1:550 |
| 289 | sulfentrazone | dimethenamid | acetochlor | 1:500-100:1 | 100:1-1:550 |
| 290 | sulfentrazone | pendimethalin | acetochlor | 1:500-100:1 | 100:1-1:550 |
| 291 | sulfentrazone | clethodim | acetochlor | 1:500-100:1 | 100:1-1:550 |
| 292 | sulfentrazone | dicamba | acetochlor | 1:500-100:1 | 100:1-1:550 |
| 293 | sulfentrazone | imazamox | acetochlor | 1:500-100:1 | 100:1-1:550 |
| 294 | sulfentrazone | imazaquin | acetochlor | 1:500-100:1 | 100:1- 1:550 |
| 295 | sulfentrazone | imazethapyr | acetochlor | 1:500-100:1 | 100:1-1:550 |
| 296 | sulfentrazone | atrazine | acetochlor | 1:500-100:1 | 100:1-1:550 |
| 297 | sulfentrazone | diclosulam | acetochlor | 1:500-100:1 | 100:1-1:550 |
| 298 | sulfentrazone | mesotrione | acetochlor | 1:500-100:1 | 100:1-1:550 |
| 299 | sulfentrazone | isoxaflutole | acetochlor | 1:500-100:1 | 100:1-1:550 |
| 300 | sulfentrazone | topramezone | acetochlor | 1:500-100:1 | 100:1-1:550 |
| 301 | sulfentrazone | 2,4-D | acetochlor | 1:500-100:1 | 100:1-1:550 |
| 302 | flumioxazin | fomesafen | acetochlor | 1:500-100:1 | 100:1-1:550 |
| 303 | flumioxazin | clethodim | acetochlor | 1:500-100:1 | 100:1-1:550 |
| 304 | flumioxazin | imazaquin | acetochlor | 1:500-100:1 | 100:1-1:550 |
| 305 | flumioxazin | dimethenamid | acetochlor | 1:500-100:1 | 100:1-1:550 |
| 306 | flumioxazin | pendimethalin | acetochlor | 1:500-100:1 | 100:1-1:550 |
| 307 | flumioxazin | dicamba | acetochlor | 1:500-100:1 | 100:1-1:550 |
| 308 | flumioxazin | imazamox | acetochlor | 1:500-100:1 | 100:1-1:550 |
| 309 | flumioxazin | imazethapyr | acetochlor | 1:500-100:1 | 100:1-1:550 |
| 310 | flumioxazin | atrazine | acetochlor | 1:500-100:1 | 100:1-1:550 |
| 311 | flumioxazin | diclosulam | acetochlor | 1:500-100:1 | 100:1-1:550 |
| 312 | flumioxazin | mesotrione | acetochlor | 1:500-100:1 | 100:1-1:550 |
| 313 | flumioxazin | isoxaflutole | acetochlor | 1:500-100:1 | 100:1-1:550 |
| 314 | flumioxazin | topramezone | acetochlor | 1:500-100:1 | 100:1-1:550 |
| 315 | flumioxazin | 2,4-D-2- | acetochlor | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 316 | dicamba | fomesafen | acetochlor | 1:500-100:1 | 100:1-1:550 |
| 317 | dicamba | clethodim | acetochlor | 1:500-100:1 | 100:1-1:550 |
| 318 | dicamba | imazaquin | acetochlor | 1:500-100:1 | 100:1-1:550 |
| 319 | dicamba | dimethenamid | acetochlor | 1:500-100:1 | 100:1-1:550 |
| 320 | dicamba | pendimethalin | acetochlor | 1:500-100:1 | 100:1-1:550 |
| 321 | dicamba | imazamox | acetochlor | 1:500-100:1 | 100:1-1:550 |
| 322 | dicamba | imazethapyr | acetochlor | 1:500-100:1 | 100:1-1:550 |
| 323 | dicamba | atrazine | acetochlor | 1:500-100:1 | 100:1-1:550 |
| 324 | dicamba | diclosulam | acetochlor | 1:500-100:1 | 100:1-1:550 |
| 325 | dicamba | mesotrione | acetochlor | 1:500-100:1 | 100:1-1:550 |
| 326 | dicamba | isoxaflutole | acetochlor | 1:500-100:1 | 100:1-1:550 |
| 327 | dicamba | topramezone | acetochlor | 1:500-100:1 | 100:1-1:550 |
| 328 | sulfentrazone | flumioxazin | imazethapyr | 1:500-100:1 | 100:1-1:550 |
| 329 | sulfentrazone | fomesafen | imazethapyr | 1:500-100:1 | 100:1-1:550 |
| 330 | sulfentrazone | dimethenamid | imazethapyr | 1:500-100:1 | 100:1-1:550 |
| 331 | sulfentrazone | acetochlor | imazethapyr | 1:500-100:1 | 100:1-1:550 |
| 332 | sulfentrazone | pendimethalin | imazethapyr | 1:500-100:1 | 100:1-1:550 |
| 333 | sulfentrazone | clethodim | imazethapyr | 1:500-100:1 | 100:1-1:550 |
| 334 | sulfentrazone | dicamba | imazethapyr | 1:500-100:1 | 100:1-1:550 |
| 335 | sulfentrazone | imazamox | imazethapyr | 1:500-100:1 | 100:1-1:550 |
| 336 | sulfentrazone | imazaquin | imazethapyr | 1:500-100:1 | 100:1-1:550 |
| 337 | sulfentrazone | atrazine | imazethapyr | 1:500-100:1 | 100:1-1:550 |
| 338 | sulfentrazone | diclosulam | imazethapyr | 1:500-100:1 | 100:1-1:550 |
| 339 | sulfentrazone | mesotrione | imazethapyr | 1:500-100:1 | 100:1-1:550 |
| 340 | sulfentrazone | isoxaflutole | imazethapyr | 1:500-100:1 | 100:1-1:550 |
| 341 | sulfentrazone | topramezone | imazethapyr | 1:500-100:1 | 100:1-1:550 |
| 342 | sulfentrazone | 2,4-D | imazethapyr | 1:500-100:1 | 100:1-1:550 |
| 343 | flumioxazin | fomesafen | imazethapyr | 1:500-100:1 | 100:1-1:550 |
| 344 | flumioxazin | clethodim | imazethapyr | 1:500-100:1 | 100:1-1:550 |
| 345 | flumioxazin | imazaquin | imazethapyr | 1:500-100:1 | 100:1-1:550 |
| 346 | flumioxazin | dimethenamid | imazethapyr | 1:500-100:1 | 100:1-1:550 |
| 347 | flumioxazin | acetochlor | imazethapyr | 1:500-100:1 | 100:1-1:550 |
| 348 | flumioxazin | pendimethalin | imazethapyr | 1:500-100:1 | 100:1-1:550 |
| 349 | flumioxazin | dicamba | imazethapyr | 1:500-100:1 | 100:1-1:550 |
| 350 | flumioxazin | imazamox | imazethapyr | 1:500-100:1 | 100:1-1:550 |
| 351 | flumioxazin | atrazine | imazethapyr | 1:500-100:1 | 100:1-1:550 |
| 352 | flumioxazin | diclosulam | imazethapyr | 1:500-100:1 | 100:1-1:550 |
| 353 | flumioxazin | mesotrione | imazethapyr | 1:500-100:1 | 100:1-1:550 |
| 354 | flumioxazin | isoxaflutole | imazethapyr | 1:500-100:1 | 100:1-1:550 |
| 355 | flumioxazin | topramezone | imazethapyr | 1:500-100:1 | 100:1-1:550 |
| 356 | flumioxazin | 2,4-D-2-ethylhexyl | imazethapyr | 1:500-100:1 | 100:1-1:550 |
| 357 | dicamba | fomesafen | imazethapyr | 1:500-100:1 | 100:1-1:550 |
| 358 | dicamba | clethodim | imazethapyr | 1:500-100:1 | 100:1-1:550 |
| 359 | dicamba | imazaquin | imazethapyr | 1:500-100:1 | 100:1-1:550 |
| 360 | dicamba | dimethenamid | imazethapyr | 1:500-100:1 | 100:1-1:550 |
| 361 | dicamba | acetochlor | imazethapyr | 1:500-100:1 | 100:1-1:550 |
| 362 | dicamba | pendimethalin | imazethapyr | 1:500-100:1 | 100:1-1:550 |
| 363 | dicamba | imazamox | imazethapyr | 1:500-100:1 | 100:1-1:550 |
| 364 | dicamba | atrazine | imazethapyr | 1:500-100:1 | 100:1-1:550 |
| 365 | dicamba | diclosulam | imazethapyr | 1:500-100:1 | 100:1-1:550 |
| 366 | dicamba | mesotrione | imazethapyr | 1:500-100:1 | 100:1-1:550 |
| 367 | dicamba | isoxaflutole | imazethapyr | 1:500-100:1 | 100:1-1:550 |
| 368 | dicamba | topramezone | imazethapyr | 1:500-100:1 | 100:1-1:550 |
| 369 | sulfentrazone | flumioxazin | imazamox | 1:500-100:1 | 100:1-1:550 |
| 370 | sulfentrazone | fomesafen | imazamox | 1:500-100:1 | 100:1-1:550 |
| 371 | sulfentrazone | dimethenamid | imazamox | 1:500-100:1 | 100:1-1:550 |
| 372 | sulfentrazone | acetochlor | imazamox | 1:500-100:1 | 100:1-1:550 |
| 373 | sulfentrazone | pendimethalin | imazamox | 1:500-100:1 | 100:1-1:550 |
| 374 | sulfentrazone | clethodim | imazamox | 1:500-100:1 | 100:1-1:550 |
| 375 | sulfentrazone | dicamba | imazamox | 1:500-100:1 | 100:1-1:550 |
| 376 | sulfentrazone | imazaquin | imazamox | 1:500-100:1 | 100:1-1:550 |
| 377 | sulfentrazone | imazethapyr | imazamox | 1:500-100:1 | 100:1-1:550 |
| 378 | sulfentrazone | atrazine | imazamox | 1:500-100:1 | 100:1-1:550 |
| 379 | sulfentrazone | diclosulam | imazamox | 1:500-100:1 | 100:1-1:550 |
| 380 | sulfentrazone | mesotrione | imazamox | 1:500-100:1 | 100:1-1:550 |
| 381 | sulfentrazone | isoxaflutole | imazamox | 1:500-100:1 | 100:1-1:550 |
| 382 | sulfentrazone | topramezone | imazamox | 1:500-100:1 | 100:1-1:550 |
| 383 | sulfentrazone | 2,4-D | imazamox | 1:500-100:1 | 100:1-1:550 |
| 384 | flumioxazin | fomesafen | imazamox | 1:500-100:1 | 100:1-1:550 |
| 385 | flumioxazin | clethodim | imazamox | 1:500-100:1 | 100:1-1:550 |
| 386 | flumioxazin | imazaquin | imazamox | 1:500-100:1 | 100:1-1:550 |
| 387 | flumioxazin | dimethenamid | imazamox | 1:500-100:1 | 100:1-1:550 |
| 388 | flumioxazin | acetochlor | imazamox | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 389 | flumioxazin | pendimethalin | imazamox | 1:500-100:1 | 100:1-1:550 |
| 390 | flumioxazin | dicamba | imazamox | 1:500-100:1 | 100:1-1:550 |
| 391 | flumioxazin | imazethapyr | imazamox | 1:500-100:1 | 100:1-1:550 |
| 392 | flumioxazin | atrazine | imazamox | 1:500-100:1 | 100:1-1:550 |
| 393 | flumioxazin | diclosulam | imazamox | 1:500-100:1 | 100:1-1:550 |
| 394 | flumioxazin | mesotrione | imazamox | 1:500-100:1 | 100:1-1:550 |
| 395 | flumioxazin | isoxaflutole | imazamox | 1:500-100:1 | 100:1-1:550 |
| 396 | flumioxazin | topramezone | imazamox | 1:500-100:1 | 100:1-1:550 |
| 397 | flumioxazin | 2,4-D-2-ethylhexyl | imazamox | 1:500-100:1 | 100:1-1:550 |
| 398 | dicamba | fomesafen | imazamox | 1:500-100:1 | 100:1-1:550 |
| 399 | dicamba | clethodim | imazamox | 1:500-100:1 | 100:1-1:550 |
| 400 | dicamba | imazaquin | imazamox | 1:500-100:1 | 100:1-1:550 |
| 401 | dicamba | dimethenamid | imazamox | 1:500-100:1 | 100:1-1:550 |
| 402 | dicamba | acetochlor | imazamox | 1:500-100:1 | 100:1-1:550 |
| 403 | dicamba | pendimethalin | imazamox | 1:500-100:1 | 100:1-1:550 |
| 404 | dicamba | imazethapyr | imazamox | 1:500-100:1 | 100:1-1:550 |
| 405 | dicamba | atrazine | imazamox | 1:500-100:1 | 100:1-1:550 |
| 406 | dicamba | diclosulam | imazamox | 1:500-100:1 | 100:1-1:550 |
| 407 | dicamba | mesotrione | imazamox | 1:500-100:1 | 100:1-1:550 |
| 408 | dicamba | isoxaflutole | imazamox | 1:500-100:1 | 100:1-1:550 |
| 409 | dicamba | topramezone | imazamox | 1:500-100:1 | 100:1-1:550 |
| 410 | sulfentrazone | flumioxazin | imazapyr | 1:500-100:1 | 100:1-1:550 |
| 411 | sulfentrazone | fomesafen | imazapyr | 1:500-100:1 | 100:1-1:550 |
| 412 | sulfentrazone | dimethenamid | imazapyr | 1:500-100:1 | 100:1-1:550 |
| 413 | sulfentrazone | acetochlor | imazapyr | 1:500-100:1 | 100:1-1:550 |
| 414 | sulfentrazone | pendimethalin | imazapyr | 1:500-100:1 | 100:1-1:550 |
| 415 | sulfentrazone | clethodim | imazapyr | 1:500-100:1 | 100:1-1:550 |
| 416 | sulfentrazone | imazamox | imazapyr | 1:500-100:1 | 100:1-1:550 |
| 417 | sulfentrazone | imazaquin | imazapyr | 1:500-100:1 | 100:1-1:550 |
| 418 | sulfentrazone | imazethapyr | imazapyr | 1:500-100:1 | 100:1-1:550 |
| 419 | sulfentrazone | atrazine | imazapyr | 1:500-100:1 | 100:1-1:550 |
| 420 | sulfentrazone | diclosulam | imazapyr | 1:500-100:1 | 100:1-1:550 |
| 421 | sulfentrazone | mesotrione | imazapyr | 1:500-100:1 | 100:1-1:550 |
| 422 | sulfentrazone | isoxaflutole | imazapyr | 1:500-100:1 | 100:1-1:550 |
| 423 | sulfentrazone | topramezone | imazapyr | 1:500-100:1 | 100:1-1:550 |
| 424 | sulfentrazone | 2,4-D | imazapyr | 1:500-100:1 | 100:1-1:550 |
| 425 | flumioxazin | fomesafen | imazapyr | 1:500-100:1 | 100:1-1:550 |
| 426 | flumioxazin | clethodim | imazapyr | 1:500-100:1 | 100:1-1:550 |
| 427 | flumioxazin | imazaquin | imazapyr | 1:500-100:1 | 100:1-1:550 |
| 428 | flumioxazin | dimethenamid | imazapyr | 1:500-100:1 | 100:1-1:550 |
| 429 | flumioxazin | acetochlor | imazapyr | 1:500-100:1 | 100:1-1:550 |
| 430 | flumioxazin | pendimethalin | imazapyr | 1:500-100:1 | 100:1-1:550 |
| 431 | flumioxazin | imazamox | imazapyr | 1:500-100:1 | 100:1-1:550 |
| 432 | flumioxazin | imazethapyr | imazapyr | 1:500-100:1 | 100:1-1:550 |
| 433 | flumioxazin | atrazine | imazapyr | 1:500-100:1 | 100:1-1:550 |
| 434 | flumioxazin | diclosulam | imazapyr | 1:500-100:1 | 100:1-1:550 |
| 435 | flumioxazin | mesotrione | imazapyr | 1:500-100:1 | 100:1-1:550 |
| 436 | flumioxazin | isoxaflutole | imazapyr | 1:500-100:1 | 100:1-1:550 |
| 437 | flumioxazin | topramezone | imazapyr | 1:500-100:1 | 100:1-1:550 |
| 438 | flumioxazin | 2,4-D-2-ethylhexyl | imazapyr | 1:500-100:1 | 100:1-1:550 |
| 439 | sulfentrazone | flumioxazin | imazapic | 1:500-100:1 | 100:1-1:550 |
| 440 | sulfentrazone | fomesafen | imazapic | 1:500-100:1 | 100:1-1:550 |
| 441 | sulfentrazone | dimethenamid | imazapic | 1:500-100:1 | 100:1-1:550 |
| 442 | sulfentrazone | acetochlor | imazapic | 1:500-100:1 | 100:1-1:550 |
| 443 | sulfentrazone | pendimethalin | imazapic | 1:500-100:1 | 100:1-1:550 |
| 444 | sulfentrazone | clethodim | imazapic | 1:500-100:1 | 100:1-1:550 |
| 445 | sulfentrazone | dicamba | imazapic | 1:500-100:1 | 100:1-1:550 |
| 446 | sulfentrazone | imazamox | imazapic | 1:500-100:1 | 100:1-1:550 |
| 447 | sulfentrazone | imazaquin | imazapic | 1:500-100:1 | 100:1-1:550 |
| 448 | sulfentrazone | imazethapyr | imazapic | 1:500-100:1 | 100:1-1:550 |
| 449 | sulfentrazone | atrazine | imazapic | 1:500-100:1 | 100:1-1:550 |
| 450 | sulfentrazone | diclosulam | imazapic | 1:500-100:1 | 100:1-1:550 |
| 451 | sulfentrazone | mesotrione | imazapic | 1:500-100:1 | 100:1-1:550 |
| 452 | sulfentrazone | isoxaflutole | imazapic | 1:500-100:1 | 100:1-1:550 |
| 453 | sulfentrazone | topramezone | imazapic | 1:500-100:1 | 100:1-1:550 |
| 454 | sulfentrazone | 2,4-D | imazapic | 1:500-100:1 | 100:1-1:550 |
| 455 | flumioxazin | fomesafen | imazapic | 1:500-100:1 | 100:1-1:550 |
| 456 | flumioxazin | clethodim | imazapic | 1:500-100:1 | 100:1-1:550 |
| 457 | flumioxazin | imazaquin | imazapic | 1:500-100:1 | 100:1-1:550 |
| 458 | flumioxazin | dimethenamid | imazapic | 1:500-100:1 | 100:1-1:550 |
| 459 | flumioxazin | acetochlor | imazapic | 1:500-100:1 | 100:1-1:550 |
| 460 | flumioxazin | pendimethalin | imazapic | 1:500-100:1 | 100:1-1:550 |
| 461 | flumioxazin | dicamba | imazapic | 1:500-100:1 | 100:1-1:550 |

TABLE 2-continued

Each of the following herbicidal combinations of Nos. 1 to 523 includes, besides the listed herbicides B, C and D, saflufenacil as herbicide A.

| No. | Herbicide B* | Herbicide C* | Herbicide D* | A:C w/w | B:(A + C + D) w/w |
|---|---|---|---|---|---|
| 462 | flumioxazin | imazamox | imazapic | 1:500-100:1 | 100:1-1:550 |
| 463 | flumioxazin | imazethapyr | imazapic | 1:500-100:1 | 100:1-1:550 |
| 464 | flumioxazin | atrazine | imazapic | 1:500-100:1 | 100:1-1:550 |
| 465 | flumioxazin | diclosulam | imazapic | 1:500-100:1 | 100:1-1:550 |
| 466 | flumioxazin | mesotrione | imazapic | 1:500-100:1 | 100:1-1:550 |
| 467 | flumioxazin | isoxaflutole | imazapic | 1:500-100:1 | 100:1-1:550 |
| 468 | flumioxazin | topramezone | imazapic | 1:500-100:1 | 100:1-1:550 |
| 469 | flumioxazin | 2,4-D-2-ethylhexyl | imazapic | 1:500-100:1 | 100:1-1:550 |
| 470 | dicamba | fomesafen | imazapic | 1:500-100:1 | 100:1-1:550 |
| 471 | dicamba | clethodim | imazapic | 1:500-100:1 | 100:1-1:550 |
| 472 | dicamba | imazaquin | imazapic | 1:500-100:1 | 100:1-1:550 |
| 473 | dicamba | dimethenamid | imazapic | 1:500-100:1 | 100:1-1:550 |
| 474 | dicamba | acetochlor | imazapic | 1:500-100:1 | 100:1-1:550 |
| 475 | dicamba | pendimethalin | imazapic | 1:500-100:1 | 100:1-1:550 |
| 476 | dicamba | imazamox | imazapic | 1:500-100:1 | 100:1-1:550 |
| 477 | dicamba | imazethapyr | imazapic | 1:500-100:1 | 100:1-1:550 |
| 478 | dicamba | atrazine | imazapic | 1:500-100:1 | 100:1-1:550 |
| 479 | dicamba | diclosulam | imazapic | 1:500-100:1 | 100:1-1:550 |
| 480 | dicamba | mesotrione | imazapic | 1:500-100:1 | 100:1-1:550 |
| 481 | dicamba | isoxaflutole | imazapic | 1:500-100:1 | 100:1-1:550 |
| 482 | dicamba | topramezone | imazapic | 1:500-100:1 | 100:1-1:550 |
| 483 | sulfentrazone | flumioxazin | pendimethalin | 1:500-100:1 | 100:1-1:550 |
| 484 | sulfentrazone | fomesafen | pendimethalin | 1:500-100:1 | 100:1-1:550 |
| 485 | sulfentrazone | dimethenamid | pendimethalin | 1:500-100:1 | 100:1-1:550 |
| 486 | sulfentrazone | acetochlor | pendimethalin | 1:500-100:1 | 100:1-1:550 |
| 487 | sulfentrazone | clethodim | pendimethalin | 1:500-100:1 | 100:1-1:550 |
| 488 | sulfentrazone | dicamba | pendimethalin | 1:500-100:1 | 100:1-1:550 |
| 489 | sulfentrazone | imazamox | pendimethalin | 1:500-100:1 | 100:1-1:550 |
| 490 | sulfentrazone | imazaquin | pendimethalin | 1:500-100:1 | 100:1-1:550 |
| 491 | sulfentrazone | imazethapyr | pendimethalin | 1:500-100:1 | 100:1-1:550 |
| 492 | sulfentrazone | atrazine | pendimethalin | 1:500-100:1 | 100:1-1:550 |
| 493 | sulfentrazone | diclosulam | pendimethalin | 1:500-100:1 | 100:1-1:550 |
| 494 | sulfentrazone | mesotrione | pendimethalin | 1:500-100:1 | 100:1-1:550 |
| 495 | sulfentrazone | isoxaflutole | pendimethalin | 1:500-100:1 | 100:1-1:550 |
| 496 | sulfentrazone | topramezone | pendimethalin | 1:500-100:1 | 100:1-1:550 |
| 497 | sulfentrazone | 2,4-D | pendimethalin | 1:500-100:1 | 100:1-1:550 |
| 498 | flumioxazin | fomesafen | pendimethalin | 1:500-100:1 | 100:1-1:550 |
| 499 | flumioxazin | clethodim | pendimethalin | 1:500-100:1 | 100:1-1:550 |
| 500 | flumioxazin | imazaquin | pendimethalin | 1:500-100:1 | 100:1-1:550 |
| 501 | flumioxazin | dimethenamid | pendimethalin | 1:500-100:1 | 100:1-1:550 |
| 502 | flumioxazin | acetochlor | pendimethalin | 1:500-100:1 | 100:1-1:550 |
| 503 | flumioxazin | dicamba | pendimethalin | 1:500-100:1 | 100:1-1:550 |
| 504 | flumioxazin | imazamox | pendimethalin | 1:500-100:1 | 100:1-1:550 |
| 505 | flumioxazin | imazethapyr | pendimethalin | 1:500-100:1 | 100:1-1:550 |
| 506 | flumioxazin | atrazine | pendimethalin | 1:500-100:1 | 100:1-1:550 |
| 507 | flumioxazin | diclosulam | pendimethalin | 1:500-100:1 | 100:1-1:550 |
| 508 | flumioxazin | mesotrione | pendimethalin | 1:500-100:1 | 100:1-1:550 |
| 509 | flumioxazin | isoxaflutole | pendimethalin | 1:500-100:1 | 100:1-1:550 |
| 510 | flumioxazin | topramezone | pendimethalin | 1:500-100:1 | 100:1-1:550 |
| 511 | flumioxazin | 2,4-D-2-ethylhexyl | pendimethalin | 1:500-100:1 | 100:1-1:550 |
| 512 | dicamba | fomesafen | pendimethalin | 1:500-100:1 | 100:1-1:550 |
| 513 | dicamba | clethodim | pendimethalin | 1:500-100:1 | 100:1-1:550 |
| 514 | dicamba | imazaquin | pendimethalin | 1:500-100:1 | 100:1-1:550 |
| 515 | dicamba | dimethenamid | pendimethalin | 1:500-100:1 | 100:1-1:550 |
| 516 | dicamba | acetochlor | pendimethalin | 1:500-100:1 | 100:1-1:550 |
| 517 | dicamba | imazamox | pendimethalin | 1:500-100:1 | 100:1-1:550 |
| 518 | dicamba | imazethapyr | pendimethalin | 1:500-100:1 | 100:1-1:550 |
| 519 | dicamba | atrazine | pendimethalin | 1:500-100:1 | 100:1-1:550 |
| 520 | dicamba | diclosulam | pendimethalin | 1:500-100:1 | 100:1-1:550 |
| 521 | dicamba | mesotrione | pendimethalin | 1:500-100:1 | 100:1-1:550 |
| 522 | dicamba | isoxaflutole | pendimethalin | 1:500-100:1 | 100:1-1:550 |
| 523 | dicamba | topramezone | pendimethalin | 1:500-100:1 | 100:1-1:550 |

*may be applied in the form of its enantiomer, salt or ester, unless a specific enantiomer, salt or ester is mentioned.

The combinations of the invention may also comprise one or more safeners. Safeners, also termed as herbicide safeners are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. However, in the combinations of the present invention, safeners are generally not required. Therefore, a preferred embodiment of the invention relates to combinations which contain no safener or virtually no safener (i.e. less than 1% by weight, based on the total amount of herbicide A and herbicide B).

Suitable safeners, which can be used in the combinations according to the present invention are known in the art, e.g. from The Compendium of Pesticide Common Names (http://www.alanwood.net/pesticides/); Farm Chemicals Handbook 2000 Vol. 86, Meister Publishing Company, 2000;

B. Hock, C. Fedtke, R. R. Schmidt, Herbizide, Georg Thieme Verlag, Stuttgart 1995;

W. H. Ahrens, Herbicide Handbook, 7$^{th}$ Edition, Weed Science Society of America, 1994; and K. K. Hatzios, Herbicide Handbook, Supplement to 7th Edition, Weed Science Society of America, 1998.

Safeners include benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic acid anhydride, 2,2,5-trimethyl-3-(dichloracetyl)-1,3-oxazolidine, 4-(dichloroacetyl)-1-oxa-4-azaspiro[4.5]decane and oxabetrinil, as well as their agriculturally acceptable salts and, provided they have a carboxyl group, their agriculturally acceptable derivatives. 2,2,5-trimethyl-3-(dichloracetyl)-1,3-oxazolidine [CAS No. 52836-31-4] is also known under the name R-29148. 4-(Dichloroacetyl)-1-oxa-4-azaspiro[4.5]decane [CAS No. 71526-07-03] is also known under the names AD-67 and MON 4660.

As safener, the combinations according to the invention comprise at least one of the compounds which is preferably selected from the group of benoxacor, cloquintocet, cyprosulfamide, dichlormid, fenchlorazole, fenclorim, furilazole, isoxadifen, mefenpyr, naphthalic acid anhydride, 2,2,5-trimethyl-3-(dichloroacetyl)-1,3-oxazolidine and 4-(dichloroacetyl)-1-oxa-4-azaspiro[4.5]decane, and their agriculturally acceptable salts and, in the case of compounds having a COOH group, their agriculturally acceptable derivatives as defined above.

A preferred embodiment of the invention relates to combinations which contain no safener or virtually no safener, i.e. less than 1% by weight, based on the total amount of the herbicide B, saflufenacil, the at least one herbicide C and the optional herbicide D to be applied.

The combinations of the present invention are suitable for controlling a large number of harmful plants, including monocotyledonous weeds, in particular annual weeds such as gramineous weeds (grasses) including *Echinochloa* species such as barnyardgrass (*Echinochloa crusgalli* var. *crusgalli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus*, *Bromus* species, *Lolium* species, *Phalaris* species, *Eriochloa* species, *Panicum* species, *Brachiaria* species, annual bluegrass (*Poa annua*), blackgrass (*Alopecurus myosuroides*), *Aegilops cylindrica*, *Agropyron repens*, *Apera spica-venti*, *Eleusine indica*, *Cynodon dactylon* and the like.

The combinations of the present invention are also suitable for controlling a large number of dicotyledonous weeds, in particular broad leaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pilosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia brasiliensis*, and the like.

The combinations of the present invention are also suitable for controlling a large number of annual and perennial sedge weeds including cyperus species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

Therefore, the present invention also relates to a method for controlling undesirable vegetation, comprising applying a herbicidal combination according to the present invention, i.e. a herbicidal combination comprising:
  a) saflufenacil,
  b) a single herbicide B or one of its salts,
  c) at least one herbicide C as defined above, and
  d) optionally at least one further herbicide D as defined above, to a locus where undesirable vegetation is present or is expected to be present.

The combinations of the present invention are particularly useful in so-called burndown programs, in particular pre-plant burndown programs. i.e. the combinations of the invention are applied to a locus where crops will be planted before planting or emergence of the crop.

Therefore, the present invention also relates to a method for burndown treatment of undesirable vegetation in crops, comprising applying a herbicidal combination according to the present invention, i.e. a herbicidal combination comprising:
  a) saflufenacil,
  b) single herbicide B or one of its salts,
  c) at least one herbicide C as defined above, and
  d) optionally at least one further herbicide D as defined above,
to a locus where crops will be planted before planting or emergence of the crop.

In the burndown treatment of the present invention, additionally at least one further herbicide D as defined above can be applied together with the herbicides A, B and C. The term "to apply together" includes simultaneous and successive application. Likewise, applying the composition does not necessarily mean that the compounds A, B, C and optionally D must be applied as a single formulation or as a tank mix. Rather, the combination includes separate formulations of herbicides A, B and C and optionally D, which can be applied as a single tank-mix or via separate application means. In any case, the herbicide A, the herbicide B, the at least one herbicide C and the one or more optional herbicides D can be applied simultaneously or in succession.

However, it is also possible to apply the herbicides C and D in the burndown treatment after seeding or even after emergence of the crop.

Though possible, it is not necessary to formulate the herbicides A, B, C and optionally D in a single formulation. Usually the herbicides A, B, C and optionally D are combined as a tank-mix prior to application. It is however also possible to provide a premix of the herbicides A and C and the optional herbicide D and to combine this premix with the herbicide B.

The combinations of the present invention can be applied in conventional manner by using techniques as skilled person is familiar with. Suitable techniques include spraying, atomizing, dusting, spreading or watering. The type of application depends on the intended purpose in a well known manner; in any case, they should ensure the finest possible distribution of the active ingredients according to the invention.

The combinations are applied to locus mainly by spraying, in particular foliar spraying of an aqueous dilution of the active ingredients of the combination. Application can be carried out by customary spraying techniques using, for example, water as carrier and spray liquor rates of from about 10 to 2000 l/ha or 50 to 1000 l/ha (for example from 100 to 500 l/ha). Application of the herbicidal combinations by the low-volume and the ultra-low-volume method is possible, as is their application in the form of microgranules.

If the active ingredients are less well tolerated by certain crop plants, application techniques may be used in which the herbicidal combinations are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

The combinations can be applied pre- or post-emergence, i.e. before, during and/or after emergence of the undesirable plants.

When the combinations are used in burndown programs, they can be applied prior to seeding (planting) or after seeding (or planting) of the crop plants but before the emergence of the crop plants. The combinations are preferably applied prior to seeding of the crop plants. For burndown, the combinations will generally be applied at a date up to 9 month, frequently up to 6 month, preferably up to 4 month prior to planting the crop. The burndown application can be done at a date up to 1 day prior to emergence of the crop plant and is preferably done at a date prior to seeding/planting of the crop plant, preferably at a date of at least one day, preferably at least 2 days and in particular at least one 4 days prior to planting or from 6 month to 1 day prior emergence, in particular from 4 month to 2 days prior emergence and more preferably from 4 month to 4 days prior emergence. It is, of course, possible to repeat the burndown application once or more, e.g. once, twice, three times, four times or five times within that time frame.

In the burndown treatment according to the present invention, the herbicide A, the herbicide B and the at least one herbicide C are applied to the field of the crop plants prior to the emergence of the crop plants, in particular prior to seeding within the above time frame. In a specific embodiment of this burndown treatment, the one or more herbicides D are also applied within this time frame. In this specific embodiment it is also possible to additionally apply the one or more herbicides D and optionally additional amounts of saflufenacil and/or the at least one herbicide C after the planting or seeding or even after emergence of the crop, preferably at a date until 12 weeks after emergence of the crop. In another specific embodiment of this burndown treatment, the one or more herbicides D and the optional additional amounts of saflufenacil and the at least one herbicide C are only applied after the planting or seeding or even after emergence of the crop, preferably at a date until 12 weeks after emergence of the crop.

It is a particular benefit of the combinations according to the invention that they have a very good post-emergence herbicide activity, i.e. they show a good herbicidal activity against emerged undesirable plants. Thus, in a preferred embodiment of the invention, the combinations are applied post-emergence, i.e. during and/or after, the emergence of the undesirable plants. It is particularly advantageous to apply the mixtures according to the invention post-emergent when the undesirable plant starts with leaf development up to flowering. The combinations are particularly useful for controlling undesirable vegetation which has already developed to a state, which is difficult to control with conventional burndown combinations, i.e. when the individual weed is taller than 10 cm (4 inches) or even taller than 15 cm (6 inches) and/or for heavy weed populations.

In the case of a post-emergence treatment of the plants, the herbicidal mixtures or combinations according to the invention are preferably applied by foliar application.

Application may be effected, for example, by usual spraying techniques with water as the carrier, using amounts of spray mixture of usually from 10 to 2000 l/ha, in particular 50 to 1000 l/ha.

The required application rate of the combination of the pure active compounds, i.e. of saflufenacil, herbicide B, at least one herbicide C and optionally herbicide D depends on the density of the undesired vegetation, on the development stage of the plants, on the climatic conditions of the location where the combination is used and on the application method. In general, the application rate of the combination (total amount of herbicides A, B, C and optional further actives) is from 55 to 6000 g/ha, preferably from 100 to 5000 g/ha, from 200 to 4000 g/ha, and more preferably from 300 to 3000 g/ha of active ingredient (a.i.).

The rate of application of saflufenacil is usually from 1 g/ha to 500 g/ha and preferably in the range from 5 g/ha to 250 g/ha or from 10 g/ha to 100 g/ha of active substance (a.i.).

The rate of application of herbicide B is usually from 10 g/ha to 4000 g/ha and preferably in the range from 25 g/ha to 3000 g/ha or from 50 g/ha to 2000 g/ha of active substance (a.i.).

The application rates of the herbicide C (total amount of herbicide C) are generally in the range from 0.5 g/ha to 8000 g/ha and preferably in the range from 1 g/ha to 6000 g/ha or from 2 g/ha to 4000 g/ha of active substance.

The application rates of the herbicide C.1 (total amount of herbicide C.1) are generally in the range from 0.5 g/ha to 1000 g/ha and preferably in the range from 1 g/ha to 500 g/ha or from 2 g/ha to 250 g/ha of active substance.

The application rates of the herbicide C.2 (total amount of herbicide C.2) are generally in the range from 1 g/ha to 5000 g/ha and preferably in the range from 2 g/ha to 2000 g/ha or from 5 g/ha to 1500 g/ha of active substance.

The application rates of the herbicide C.3 (total amount of herbicide C.3) are generally in the range from 10 g/ha to 8000 g/ha and preferably in the range from 20 g/ha to 6000 g/ha or from 100 g/ha to 4000 g/ha of active substance.

The application rates of the herbicide C.4 (total amount of herbicide C.4) are generally in the range from 10 g/ha to 8000 g/ha and preferably in the range from 20 g/ha to 6000 g/ha or from 40 g/ha to 4000 g/ha of active substance.

The application rates of the herbicide C.5 (total amount of herbicide C.5) are generally in the range from 1 g/ha to 2000 g/ha and preferably in the range from 2 g/ha to 1000 g/ha or from 5 g/ha to 750 g/ha of active substance.

The required application rates of the herbicide C.6 (total amount of herbicide C.6) are generally in the range from 10 g/ha to 8000 g/ha and preferably in the range from 20 g/ha to 6000 g/ha or from 50 g/ha to 4000 g/ha of active substance.

The application rates of the herbicide C.7 (total amount of herbicide C.7) are generally in the range from 1 g/ha to 3000 g/ha and preferably in the range from 5 g/ha to 2000 g/ha or from 10 g/ha to 1000 g/ha of active substance.

The application rates of the herbicide C.8 (total amount of herbicide C.8) are generally in the range from 10 g/ha to 8000 g/ha and preferably in the range from 20 g/ha to 6000 g/ha or from 40 g/ha to 4000 g/ha of active substance.

The application rates of the safener, if applied, are generally in the range from 1 g/ha to 5000 g/ha and preferably in the range from 2 g/ha to 5000 g/ha or from 5 g/ha to 5000 g/ha of active substance. Preferably no safener or virtually no safener is applied and thus the application rates are below 5 g/ha, in particular below 2 g/ha or below 1 g/ha.

The combinations according to the present invention are suitable for combating/controlling common harmful plants in fields, where useful plants shall be planted (i.e. in crops). The combinations of the present invention are generally suitable for burndown of undesired vegetation in fields of the following crops:

Grain crops, including e.g.
cereals (small grain crops) such as wheat (*Triticum aestivum*) and wheat like crops such as durum (*T. durum*), einkorn (*T. monococcum*), emmer (*T. dicoccon*) and spelt (*T. spelta*), rye (*Secale cereale*), triticale (*Triticosecale*), barley (*Hordeum vulgare*);
maize (corn; *Zea mays*);
sorghum (e.g. *Sorghum bicolor*);
rice (*Oryza* spp. such as *Oryza sativa* and *Oryza glaberrima*); and
sugarcane;
Legumes (Fabaceae), including e.g. soybeans (*Glycine max*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (*lens culinaris* var);
Brassicaceae, including e.g. canola (*Brassica napus*), oilseed rape (OSR, *Brassica napus*), cabbage (*B. oleracea* var), mustard such as *B. juncea, B. campestris, B. narinosa, B. nigra* and *B. tournefortir*, and turnip (*Brassica raga* var);
other broadleaf crops including e.g. sunflower, cotton, flax, linseed, sugarbeet, potato and tomato;
TNV-crops (TNV: trees, nuts and vine) including e.g. grapes, citrus, pomefruit, e.g. apple and pear, coffee, pistachio and oilpalm, stonefruit, e.g. peach, almond, walnut, pecans, olive, cherry, plum and apricot;
turf, pasture and rangeland;
onion and garlic;
bulb ornamentals such as tulips and narcissus;
conifers and deciduous trees such as pinus, fir, oak, maple, dogwood, hawthorne, crabapple, and rhamnus (buckthorn); and
garden ornamentals such as roses, petunia, marigold and snapdragon.

The combinations of the present invention are in particular suitable for burndown of undesired vegetation in fields of the following crop plants: small grain crops such as wheat, barley, rye, triticale and durum, rice, maize (corn), sugarcane, *sorghum*, soybean, pulse crops such as pea, bean and lentils, peanut, sunflower, sugarbeet, potato, cotton, brassica crops, such as oilseed rape, canola, mustard, cabbage and turnip, turf, pasture, rangeland, grapes, coffee, oilpalm, pomefruit, such as apple and pear, stonefruit, such as peach, almond, walnut, pecans, olive, cherry, plum and apricot, citrus, coffee, pistachio, garden ornamentals, such as roses, petunia, marigold, snap dragon, bulb ornamentals such as tulips and narcissus, conifers and deciduous trees such as pinus, fir, oak, maple, dogwood, hawthorne, crabapple and rhamnus.

The combinations of the present invention are even more suitable for burndown of undesired vegetation in fields of the following crop plants: small grain crops such as wheat, barley, rye, triticale and durum, rice, maize, sugarcane, soybean, pulse crops such as pea, bean and lentils, peanut, sunflower, cotton, brassica crops, such as oilseed rape, canola, turf, pasture, rangeland, grapes, coffee, oilpalm, stonefruit, such as peach, almond, walnut, pecans, olive, cherry, plum and apricot, citrus and pistachio.

The combinations of the present invention are most suitable for burndown of undesired vegetation in fields of the following crop plants: small grain crops, rice, maize, sugarcane, soybean, pulse crops, peanut, sunflower, cotton, oilseed rape, canola, grapes, coffee, oilpalm and stonefruit.

If not stated otherwise, the combinations of the invention are suitable for application in fields of any variety of the aforementioned crop plants.

The combinations according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding. Suitable are for example crop plants, preferably corn, wheat, sunflower, rice, canola, oilseed rape, soybeans, cotton and sugarcane, which are resistant or tolerant to any one of herbicides B, crop plants which are resistant or tolerant to synthetic auxins such as dicamba, crop plants which are resistant or tolerant to HPPD inhibitors, crop plants which are resistant or tolerant to ALS inhibitors such as imidazolinone herbicides, crop plants which are resistant or tolerant to PPO inhibitors or crop plants which, owing to introduction of the gene for Bt toxin by genetic modification, are resistant to attack by certain insects.

In a particular a specific embodiment, the combinations of the present inventions are used for controlling undesirable vegetation to crop plants, which are tolerant to herbicides, in particular in crop plants that are resistant or tolerant to any one of herbicides B and which are stacked with further resistance or tolerance against at least one further herbicide, in particular at least one of the following herbicides: synthetic auxins such as dicamba, HPPD inhibitors, ALS inhibitors such as imidazolinone herbicides, PPO inhibitors.

In these herbicide resistant or tolerant crops, the combinations of the present invention can be used both for burndown and for control of undesired vegetation after emergence of the crops. Therefore, a particular embodiment of the invention relates to a method for controlling undesirable vegetation in herbicide resistant or tolerant crops, in particular in crop plants which are resistant or tolerant to any one of herbicides B and which are optionally stacked with further resistance or tolerance against at least one further herbicide, in particular at least one of the following herbicides: synthetic auxins such as dicamba, HPPD inhibitors, ALS inhibitors such as imidazolinone herbicides, PPO inhibitors. In this particular embodiment, the combinations can be used for burndown but also for the control of undesirable vegetation after emergence of the crop plants.

In this particular method of the invention, the combination of the invention can be applied at least once prior to planting or emergence of the herbicide resistant or tolerant crop plants to achieve effective burndown of the undesirable vegetation and the combination can also be applied after emergence of the herbicide resistant or tolerant crop plants.

If the combinations of the present invention are used in crop plants, i.e. if they are applied in fields of the crop plants after emergence of the crops, application methods and application rates as described for burndown can be applied. If the active ingredients are less well tolerated by certain crop plants, application techniques may be used in which the herbicidal combinations are sprayed, with the aid of the spray apparatus, in such a way that they come into as little contact, if any, with the leaves of the sensitive crop plants as possible while reaching the leaves of undesirable plants which grow underneath, or the bare soil (post-directed, lay-by). However, such methods are generally not necessary and the combinations can be simply applied over the top (OTT).

For example, a combination comprising sulfentrazone, saflufenacil and a synthetic auxin herbicide is particularly useful for burndown in fields both of conventional crops such as maize, canola, wheat, soybeans, sunflower and sugarcane and crops having sulfentrazone tolerance, optionally stacked with synthetic auxin tolerance. This combination can also be used for controlling undesirable vegetation in crops having sulfentrazone tolerance optionally stacked with synthetic auxin resistance after emergence of the crop.

For example, a combination comprising sulfentrazone, saflufenacil and an ALS inhibitor herbicide is particularly useful for burndown in fields both of conventional crops such as maize, wheat, soybeans, sunflower and sugarcane and crops having sulfentrazone tolerance, optionally stacked with further herbicide tolerance. This combination can also be used for controlling undesirable vegetation in such crops after emergence of the crop.

For example, a combination comprising sulfentrazone, saflufenacil and a PPO inhibitor herbicide is particularly useful for burndown in fields both of conventional crops such as maize, wheat, soybeans, sunflower and sugarcane and crops having sulfentrazone tolerance, optionally stacked with PPO inhibitor tolerance. This combination can also be used for controlling undesirable vegetation in such crops after emergence of the crop.

For example, a combination comprising sulfentrazone, saflufenacil and a microtubule inhibitor herbicide is particularly useful for burndown in fields both of conventional crops such as maize, wheat, soybeans, sunflower and sugarcane and crops having sulfentrazone tolerance, optionally stacked with further herbicide tolerance. This combination can also be used for controlling undesirable vegetation in such crops after emergence of the crop.

For example, a combination comprising sulfentrazone, saflufenacil and a HPPD inhibitor herbicide is particularly useful for burndown in fields both of conventional crops of small grain cereals and crops of small grain cereals having sulfentrazone tolerance, optionally stacked with further herbicide tolerance. This combination can also be used for controlling undesirable vegetation in such crops after emergence of the crop.

For example, a combination comprising sulfentrazone, saflufenacil and a PS II inhibitor herbicide of the group C.6.2 or C.6.3 is particularly useful for burndown in fields both of conventional crops of maize or sugarcane and crops of maize or sugarcane having sulfentrazone tolerance, optionally stacked with further herbicide tolerance. This combination can also be used for controlling undesirable vegetation in such crops after emergence of the crop.

For example, a combination comprising sulfentrazone, saflufenacil and an ACC inhibitor herbicide is particularly useful for burndown in fields both of conventional crops such as maize, wheat, soybeans, sunflower and sugarcane and crops having sulfentrazone tolerance, optionally stacked with further herbicide tolerance. This combination can also be used for controlling undesirable vegetation in such crops after emergence of the crop.

For example, a combination comprising sulfentrazone, saflufenacil and a VLCFA inhibitor herbicide is particularly useful for burndown in fields both of conventional crops of small grain cereals, maize, soybean, sunflower or sugarcane and crops of small grain cereals, maize, soybean, sunflower or sugarcane having sulfentrazone tolerance, optionally stacked with further herbicide tolerance. This combination can also be used for controlling undesirable vegetation in such crops after emergence of the crop.

The active ingredients used in the combinations of the present invention are usually available as pure substances and as formulations.

The formulations contain, besides the active ingredients of the combination, at least one organic or inorganic carrier material. The formulations may also contain, if desired, one or more surfactants and, if desired, one or more further auxiliaries customary for crop protection compositions.

The formulation may be in the form of a single package formulation containing the herbicide A, the herbicide B, the at least one herbicide C and optionally the one or more herbicides D together with liquid and/or solid carrier materials, and, if desired, one or more surfactants and, if desired, one or more further auxiliaries customary for crop protection compositions. The formulation may be in the form of a three or multi (e.g. four, five or six) package formulation, wherein one package contains a formulation of saflufenacil while a second package contains a formulation of the herbicide B, at least one further package at least one formulation of the at least one herbicide C and optionally one or more further packages contain the formulation(s) of one or more herbicides D, wherein all formulations contain at least one carrier material, if desired, one or more surfactants and, if desired, one or more further auxiliaries customary for crop protection compositions. In the case of three or multi package formulations the formulation containing saflufenacil and the formulation containing the herbicide B and the at least one formulation containing the at least one herbicide C and optionally the one or more formulations containing the one or more herbicides D are mixed prior to application. Preferably the mixing is performed as a tank mix, i.e. the formulations are mixed immediately prior or upon dilution with water.

In the formulations the active ingredients and optional further actives are present in suspended, emulsified or dissolved form. The formulation can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqeuos solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R. T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the herbicides A, B, optionally C and D with a solid carrier.

Granules, e.g. coated granules, impregnated granules and homogeneous granules, can be prepared by binding the active ingredients to solid carriers.

The formulations of the invention comprise a herbicidally effective amount of the combination of the present invention. The concentrations of the active the active ingredients in the formulations can be varied within wide ranges. In general, the formulations comprise from 1 to 98% by weight, preferably 10 to 60% by weight, of active ingredients (sum of saflufenacil, herbicide B, at least one herbicide C and optionally further actives). The active ingredients are employed in a purity of from 90% to 100%, preferably 95% to 100% (according to NMR spectrum).

The active compounds A, B, C and optionally D as well as the combinations according to the invention can, for example, be formulated as follows:

1. Products for Dilution with Water

A Water-Soluble Concentrates 10 parts by weight of active compound (or combination) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or combination) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or combination) are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or combination) are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or combination) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or combination) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or combination) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or combination), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or combination) are ground finely and mixed intimately with 95 parts by weight of finely divided kaolin. This gives a dusting powder with an active compound content of 5% by weight.

J Granules (GR, FG, GG, MG)

0.5 parts by weight of active compound (or combination) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or combination) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the combinations of the invention alone or together with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

USE EXAMPLES

The effect of the herbicidal combinations according to the invention of herbicides A, B and C and, if appropriate, safener on the growth of undesirable plants compared to the herbicidally active compounds alone or binary mixtures thereof was demonstrated by the following greenhouse experiments:

The test plants were first grown to a height of 3 to 20 cm, depending on the plant habit, and only then treated (post-emergence treatment). Here, the herbicidal combinations were suspended, emulsified or dissolved in water as distribution medium and afterwards applied by spraying, using finely distributing nozzles.

The herbicides A, B and C were used as commercially available formulations and introduced to the spray liquor with the amount of solvent system used for applying the active compound. In the examples, the solvent used was water.

Saflufenacil was used as a commercially available suspension concentrate having an active ingredient concentration of 340 g/l.

Sulfentrazone was used as a commercially available suspension concentrate having an active ingredient concentration of 480 g/l.

Flumioxazin was used as a commercially available WG-formulation having an active ingredient concentration of 50% by weight.

Dimethenamid-P was used as a commercially available emulsifiable concentrate having an active ingredient concentration of 720 g/l.

Acetochlor was used as a commercially available emulsifiable concentrate having an active ingredient concentration of 840 g/l.

Pendimethalin was used as a commercially available aqueous capsule suspension having an active ingredient concentration of 455 g/l.

Dicamba was used as a commercially available SL-formulation having an active ingredient concentration of 480 g/l.

Atrazine was used as a commercially available WG-formulation having an active ingredient concentration of 84% by weight.

Mesotrione was used as a commercially available suspension concentrate having an active ingredient concentration of 480 g/l.

Diclosulam was used as a commercially available WG-formulation having an active ingredient concentration of 84% by weight.

Isoxaflutole was used as a commercially available suspension concentrate having an active ingredient concentration of 240 g/l.

2,4-D was used as a commercially available emulsifiable concentrate containing 660 g/l of 2,4,D in the form of its 2-ethylhexyl ester (also named low volatile (LV) ester).

Imazamox was used as a commercially available SL-formulation having an active ingredient concentration of 120 g/l.

Imazethapyr was used as a commercially available SL-formulation having an active ingredient concentration of 240 g/l.

Topramezone was used as a commercially available suspension concentrate having an active ingredient concentration of 336 g/l.

Fomesafen was used as a commercially available microemulsion having an active ingredient concentration of 225 g/l.

Clethodim was used as a commercially available emulsifiable concentrate having an active ingredient concentration of 240 g/l.

The test period extended over 20 days. During this time, the plants were tended, and their response to the treatments with active compounds was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
|---|---|---|
| Abutilon theophrasti | ABUTH | velvetleaf |
| Amaranthus retroflexus | AMARE | pig weed |
| Avena fatua | AVEFA | wild oat |
| Brachiaria decumbens | BRADC | Surinam grass |
| Brachiaria platyphylla | BRAPP | broadleaf signalgrass |
| Digitaria sanguinalis | DIGSA | large crabgrass |
| Echinochloa crus-galli | ECHCG | barnyardgrass |
| Setaria viridis | SETVI | green foxtail |
| Solanum nigrum | SOLNI | black nightshade |

Colby's formula was applied to determine whether the composition showed synergistic action. The value E, which is to be expected if the activity of the individual compounds is just additive, was calculated using the method of S. R. Colby (1967) "Calculating synergistic and antagonistic responses of herbicide combinations", Weeds 15, p. 22 ff. For two component mixtures the value E was calculated by the following formula $$E = X + Y - (X \cdot Y / 100)$$

where X=effect in percent using a mixture of herbicides A and B at application rates a and b, respectively;

Y=effect in percent using herbicide C at an application rate c;

E=expected effect (in %) of A+B+C at application rates a+b+c.

If the value observed in this manner is higher than the value E calculated according to Colby, a synergistic effect is present.

Tables 1 to 41 relate to the herbicidal activities of the binary mixture of herbicides A and B, of herbicide C individually and of their combinations in post-emergence applications assessed 20 days after treatment (20 DAT).

TABLE 1

Application in Post-Emergence of Saflufenacil, Sulfentrazone and Flumioxazin

| | binary A + B and solo C applications | | | | | combination saflufenacil + sulfentrazone + flumioxazin | | | Synergism |
|---|---|---|---|---|---|---|---|---|---|
| | saflufenacil (A) + sulfentrazone (B) | | | flumioxazin (C) | | | | | |
| weed | A g ai/ha | B g ai/ha | % activity 20 DAT | g ai/ha | % activity 20 DAT | g ai/ha | observed % activity 20 DAT | expected % activity 20 DAT | Y/N 20 DAT |
| SETVI | 0.25 | 1.5 | 30 | 0.5 | 40 | 0.25 + 1.5 + 0.5 | 65 | 58 | Y |

TABLE 2

Application in Post-Emergence of Saflufenacil, Sulfentrazone and Dimethenamid-P

| | binary A + B and solo C applications | | | | | combination saflufenacil + sulfentrazone + dimethenamid-P | | | Synergism |
|---|---|---|---|---|---|---|---|---|---|
| | saflufenacil (A) + sulfentrazone (B) | | | dimethenamid-P (C) | | | | | |
| weed | A g ai/ha | B g ai/ha | % activity 20 DAT | g ai/ha | % activity 20 DAT | g ai/ha | observed % activity 20 DAT | expected % activity 20 DAT | Y/N 20 DAT |
| AMARE | 0.125 | 0.75 | 70 | 18.75 | 0 | 0.125 + 0.75 + 18.75 | 100 | 70 | Y |
| AVEFA | 0.5 | 1.5 | 40 | 75.0 | 20 | 0.5 + 1.5 + 75.0 | 60 | 52 | Y |

TABLE 3

Application in Post-Emergence of Saflufenacil, Sulfentrazone and Acetochlor

| | binary A + B and solo C applications | | | | | combination saflufenacil + | | |
| --- | --- | --- | --- | --- | --- | --- | --- | --- |
| | saflufenacil (A) + | | | | | sulfentrazone + acetochlor | | |
| | sulfentrazone (B) | | | acetochlor (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| AMARE | 0.125 | 0.75 | 70 | 12.5 | 0 | 0.125 + 0.75 + 12.5 | 100 | 70 | Y |
| SETVI | 0.25 | 1.5 | 30 | 50.0 | 10 | 0.25 + 1.5 + 50.0 | 50 | 37 | Y |

TABLE 4

Application in Post-Emergence of Saflufenacil, Sulfentrazone and Pendimethalin

| | binary A + B and solo C applications | | | | | combination saflufenacil + | | |
| --- | --- | --- | --- | --- | --- | --- | --- | --- |
| | saflufenacil (A) + | | | | | sulfentrazone + pendimethalin | | |
| | sulfentrazone (B) | | | pendimethalin (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.125 | 0.75 | 35 | 37.5 | 0 | 0.125 + 0.75 + 37.5 | 75 | 35 | Y |
| ECHCG | 0.25 | 1.5 | 30 | 150.0 | 0 | 0.25 + 1.5 + 150.0 | 50 | 30 | Y |

TABLE 5

Application in Post-Emergence of Saflufenacil, Sulfentrazone and Dicamba

| | binary A + B and solo C applications | | | | | combination saflufenacil + | | |
| --- | --- | --- | --- | --- | --- | --- | --- | --- |
| | saflufenacil (A) + | | | | | sulfentrazone + dicamba | | |
| | sulfentrazone (B) | | | dicamba (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.125 | 0.75 | 35 | 4.375 | 40 | 0.125 + 0.75 + 4.375 | 80 | 61 | Y |
| BRAPP | 0.25 | 1.5 | 10 | 17.5 | 40 | 0.25 + 1.5 + 17.5 | 60 | 46 | Y |

TABLE 6

Application in Post-Emergence of Saflufenacil, Sulfentrazone and Atrazine

| | binary A + B and solo C applications | | | | | combination saflufenacil + | | |
| --- | --- | --- | --- | --- | --- | --- | --- | --- |
| | saflufenacil (A) + | | | | | sulfentrazone + atrazine | | |
| | sulfentrazone (B) | | | atrazine (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.125 | 0.75 | 35 | 12.5 | 55 | 0.125 + 0.75 + 12.5 | 75 | 71 | Y |
| AVEFA | 0.25 | 1.5 | 20 | 12.5 | 0 | 0.25 + 1.5 + 12.5 | 35 | 20 | Y |

TABLE 7

Application in Post-Emergence of Saflufenacil, Sulfentrazone and Diclosulam

| | binary A + B and solo C applications | | | | | combination saflufenacil + sulfentrazone + diclosulam | | | |
|---|---|---|---|---|---|---|---|---|---|
| | saflufenacil (A) + sulfentrazone (B) | | | diclosulam (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| DIGSA | 0.5 | 1.5 | 20 | 0.5 | 25 | 0.5 + 1.5 + 0.5 | 45 | 40 | Y |
| SOLNI | 0.25 | 0.75 | 60 | 0.125 | 0 | 0.25 + 0.75 + 0.125 | 75 | 60 | Y |

TABLE 8

Application in Post-Emergence of Saflufenacil, Sulfentrazone and Mesotrione

| | binary A + B and solo C applications | | | | | combination saflufenacil + sulfentrazone + mesotrione | | | |
|---|---|---|---|---|---|---|---|---|---|
| | saflufenacil (A) + sulfentrazone (B) | | | mesotrione (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| DIGSA | 0.5 | 1.5 | 20 | 2.5 | 80 | 0.5 + 1.5 + 2.5 | 95 | 84 | Y |

TABLE 9

Application in Post-Emergence of Saflufenacil, Sulfentrazone and Isoxaflutole

| | binary A + B and solo C applications | | | | | combination saflufenacil + sulfentrazone + isoxaflutole | | | |
|---|---|---|---|---|---|---|---|---|---|
| | saflufenacil (A) + sulfentrazone (B) | | | isoxaflutole (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| DIGSA | 0.5 | 1.5 | 20 | 1.0 | 25 | 0.5 + 1.5 + 1.0 | 55 | 40 | Y |
| SOLNI | 0.25 | 0.75 | 60 | 0.5 | 70 | 0.25 + 0.75 + 0.5 | 98 | 88 | Y |

TABLE 10

Application in Post-Emergence of Saflufenacil, Sulfentrazone and 2-ethylhexyl ester of 2,4-D (here: 2,4-D LV ester)

| | binary A + B and solo C applications | | | | | combination saflufenacil + sulfentrazone + 2,4-D LV ester | | | |
|---|---|---|---|---|---|---|---|---|---|
| | saflufenacil (A) + sulfentrazone (B) | | | 2,4-D LV ester (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| DIGSA | 0.5 | 1.5 | 20 | 6.25 | 0 | 0.5 + 1.5 + 6.25 | 65 | 20 | Y |

TABLE 11

Application in Post-Emergence of Saflufenacil, Sulfentrazone and Imazamox

| | binary A + B and solo C applications | | | | combination saflufenacil + sulfentrazone + imazamox | | | |
|---|---|---|---|---|---|---|---|---|
| | saflufenacil (A) + | | | | | | | |
| | sulfentrazone (B) | | imazamox (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| SETVI | 0.5 | 1.5 | 60 | 0.5 | 15 | 0.5 + 1.5 + 0.5 | 80 | 66 | Y |
| DIGSA | 0.5 | 1.5 | 25 | 1.0 | 15 | 0.5 + 1.5 + 1.0 | 50 | 36 | Y |
| AMARE | 0.5 | 1.5 | 80 | 0.5 | 40 | 0.5 + 1.5 + 0.5 | 100 | 88 | Y |
| ABUTH | 0.5 | 1.5 | 60 | 0.5 | 0 | 0.5 + 1.5 + 0.5 | 70 | 60 | Y |

TABLE 12

Application in Post-Emergence of Saflufenacil, Sulfentrazone and Topramezone

| | binary A + B and solo C applications | | | | combination saflufenacil + sulfentrazone + topramezone | | | |
|---|---|---|---|---|---|---|---|---|
| | saflufenacil (A) + | | | | | | | |
| | sulfentrazone (B) | | topramezone (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| SETVI | 0.5 | 1.5 | 60 | 0.25 | 0 | 0.5 + 1.5 + 0.25 | 70 | 60 | Y |
| ECHCG | 0.25 | 1.5 | 45 | 0.25 | 25 | 0.25 + 1.5 + 0.25 | 65 | 59 | Y |
| BRADC | 0.25 | 1.5 | 0 | 0.5 | 0 | 0.25 + 1.5 + 0.5 | 25 | 0 | Y |
| AMARE | 0.5 | 1.5 | 80 | 0.25 | 40 | 0.5 + 1.5 + 0.25 | 100 | 88 | Y |
| ABUTH | 0.25 | 1.5 | 55 | 0.25 | 10 | 0.25 + 1.5 + 0.25 | 80 | 60 | Y |

TABLE 13

Application in Post-Emergence of Saflufenacil, Sulfentrazone and Imazethapyr

| | binary A + B and solo C applications | | | | combination saflufenacil + sulfentrazone + imazethapyr | | | |
|---|---|---|---|---|---|---|---|---|
| | saflufenacil (A) + | | | | | | | |
| | sulfentrazone (B) | | imazethapyr (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| DIGSA | 0.5 | 1.5 | 25 | 0.5 | 15 | 0.5 + 1.5 + 0.5 | 65 | 36 | Y |
| AVEFA | 0.5 | 1.5 | 10 | 0.5 | 0 | 0.5 + 1.5 + 0.5 | 20 | 10 | Y |
| AMARE | 0.5 | 1.5 | 80 | 1.0 | 55 | 0.5 + 1.5 + 1.0 | 100 | 91 | Y |

TABLE 14

Application in Post-Emergence of Saflufenacil, Sulfentrazone and Fomesafen

| | binary A + B and solo C applications | | | | combination saflufenacil + sulfentrazone + fomesafen | | | |
|---|---|---|---|---|---|---|---|---|
| | saflufenacil (A) + | | | | | | | |
| | sulfentrazone (B) | | fomesafen (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 3.0 | 80 | 1.5 | 5 | 0.5 + 3.0 + 1.5 | 100 | 81 | Y |

TABLE 15

Application in Post-Emergence of Saflufenacil, Sulfentrazone and Clethodim

| | binary A + B and solo C applications | | | | | combination saflufenacil + sulfentrazone + clethodim | | | |
|---|---|---|---|---|---|---|---|---|---|
| | saflufenacil (A) + | | | | | | | | |
| | sulfentrazone (B) | | | clethodim (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 3.0 | 80 | 0.75 | 5 | 0.5 + 3.0 + 0.75 | 100 | 81 | Y |
| AVEFA | 0.5 | 3.0 | 30 | 0.75 | 20 | 0.5 + 3.0 + 0.75 | 55 | 44 | Y |

TABLE 16

Application in Post-Emergence of Saflufenacil, Flumioxazin and Dimethenamid-P

| | binary A + B and solo C applications | | | | | combination saflufenacil + flumioxazin + dimethenamid-P | | | |
|---|---|---|---|---|---|---|---|---|---|
| | saflufenacil (A) + | | | | | | | | |
| | flumioxazin (B) | | | dimethenamid-P (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| BRAPP | 0.5 | 0.25 | 55 | 75.0 | 5 | 0.5 + 0.25 + 75.0 | 75 | 57 | Y |

TABLE 17

Application in Post-Emergence of Saflufenacil, Flumioxazin and Acetochlor

| | binary A + B and solo C applications | | | | | combination saflufenacil + flumioxazin + acetochlor | | | |
|---|---|---|---|---|---|---|---|---|---|
| | saflufenacil (A) + | | | | | | | | |
| | flumioxazin (B) | | | acetochlor (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| AVEFA | 1.0 | 0.25 | 20 | 50.0 | 10 | 1.0 + 0.25 + 50.0 | 30 | 28 | Y |

TABLE 18

Application in Post-Emergence of Saflufenacil, Flumioxazin and Pendimethalin

| | binary A + B and solo C applications | | | | | combination saflufenacil + flumioxazin + pendimethalin | | | |
|---|---|---|---|---|---|---|---|---|---|
| | saflufenacil (A) + | | | | | | | | |
| | flumioxazin (B) | | | pendimethalin (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| AVEFA | 1.0 | 0.25 | 20 | 150.0 | 0 | 1.0 + 0.25 + 150.0 | 30 | 20 | Y |

TABLE 19

Application in Post-Emergence of Saflufenacil, Flumioxazin and Dicamba

| | binary A + B and solo C applications | | | | | combination saflufenacil + flumioxazin + dicamba | | | |
|---|---|---|---|---|---|---|---|---|---|
| | saflufenacil (A) + | | | | | | observed % | expected % | Synergism |
| | flumioxazin (B) | | | dicamba (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| ABUTH | 0.5 | 0.13 | 85 | 4.375 | 40 | 0.5 + 0.13 + 4.375 | 100 | 91 | Y |

TABLE 20

Application in Post-Emergence of Saflufenacil, Flumioxazin and Imazamox

| | binary A + B and solo C applications | | | | | combination saflufenacil + flumioxazin + imazamox | | | |
|---|---|---|---|---|---|---|---|---|---|
| | saflufenacil (A) + | | | | | | observed % | expected % | Synergism |
| | flumioxazin (B) | | | imazamox (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| AMARE | 0.25 | 0.13 | 90 | 0.125 | 10 | 0.25 + 0.13 + 0.125 | 100 | 91 | Y |
| ECHCG | 0.25 | 0.25 | 0 | 0.5 | 0 | 0.25 + 0.25 + 0.5 | 30 | 0 | Y |

TABLE 21

Application in Post-Emergence of Saflufenacil, Flumioxazin and Imazethapyr

| | binary A + B and solo C applications | | | | | combination saflufenacil + flumioxazin + imazethapyr | | | |
|---|---|---|---|---|---|---|---|---|---|
| | saflufenacil (A) + | | | | | | observed % | expected % | Synergism |
| | flumioxazin (B) | | | imazethapyr (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| ABUTH | 0.5 | 0.13 | 85 | 0.5 | 25 | 0.5 + 0.13 + 0.5 | 100 | 89 | Y |
| DIGSA | 0.25 | 0.25 | 0 | 2.0 | 20 | 0.25 + 0.25 + 2.0 | 65 | 20 | Y |

TABLE 22

Application in Post-Emergence of Saflufenacil, Flumioxazin and Atrazine

| | binary A + B and solo C applications | | | | | combination saflufenacil + flumioxazin + atrazine | | | |
|---|---|---|---|---|---|---|---|---|---|
| | saflufenacil (A) + | | | | | | observed % | expected % | Synergism |
| | flumioxazin (B) | | | atrazine (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| ABUTH | 0.5 | 0.13 | 85 | 12.5 | 25 | 0.5 + 0.13 + 12.5 | 100 | 89 | Y |
| BRAPP | 0.25 | 0.25 | 0 | 12.5 | 0 | 0.25 + 0.25 + 12.5 | 45 | 0 | Y |

TABLE 23

Application in Post-Emergence of Saflufenacil, Flumioxazin and Diclosulam

| | binary A + B and solo C applications | | | | combination saflufenacil + flumioxazin + diclosulam | | | |
|---|---|---|---|---|---|---|---|---|
| | saflufenacil (A) + | | | | | observed % | expected % | Synergism |
| | flumioxazin (B) | | | diclosulam (C) | | | | |
| | A | B | % activity | | % activity | | activity | activity | Y/N |
| weed | g ai/ha | g ai/ha | 20 DAT | g ai/ha | 20 DAT | g ai/ha | 20 DAT | 20 DAT | 20 DAT |
| ECHCG | 0.25 | 0.25 | 0 | 1.0 | 20 | 0.25 + 0.25 + 1.0 | 70 | 20 | Y |

TABLE 24

Application in Post-Emergence of Saflufenacil, Flumioxazin and Mesotrione

| | binary A + B and solo C applications | | | | | combination saflufenacil + flumioxazin + mesotrione | | | |
|---|---|---|---|---|---|---|---|---|---|
| | saflufenacil (A) + | | | | | | observed % | expected % | Synergism |
| | flumioxazin (B) | | | mesotrione (C) | | | | | |
| | A | B | % activity | | % activity | | activity | activity | Y/N |
| weed | g ai/ha | g ai/ha | 20 DAT | g ai/ha | 20 DAT | g ai/ha | 20 DAT | 20 DAT | 20 DAT |
| AMARE | 0.25 | 0.13 | 90 | 0.625 | 0 | 0.25 + 0.13 + 0.625 | 100 | 90 | Y |
| BRAPP | 0.25 | 0.25 | 0 | 5.0 | 35 | 0.25 + 0.25 + 5.0 | 60 | 35 | Y |

TABLE 25

Application in Post-Emergence of Saflufenacil, Flumioxazin and Isoxaflutole

| | binary A + B and solo C applications | | | | | combination saflufenacil + flumioxazin + isoxaflutole | | | |
|---|---|---|---|---|---|---|---|---|---|
| | saflufenacil (A) + | | | | | | observed % | expected % | Synergism |
| | flumioxazin (B) | | | isoxaflutole (C) | | | | | |
| | A | B | % activity | | % activity | | activity | activity | Y/N |
| weed | g ai/ha | g ai/ha | 20 DAT | g ai/ha | 20 DAT | g ai/ha | 20 DAT | 20 DAT | 20 DAT |
| ABUTH | 0.5 | 0.13 | 85 | 1.0 | 85 | 0.5 + 0.13 + 1.0 | 100 | 98 | Y |
| BRAPP | 0.25 | 0.25 | 0 | 2.0 | 40 | 0.25 + 0.25 + 2.0 | 65 | 40 | Y |

TABLE 26

Application in Post-Emergence of Saflufenacil, Flumioxazin and 2,4-D 2-ethylhexyl ester (here: 2,4-D LV ester)

| | binary A + B and solo C applications | | | | | combination saflufenacil + flumioxazin + 2,4-D LV ester | | | |
|---|---|---|---|---|---|---|---|---|---|
| | saflufenacil (A) + | | | | | | observed % | expected % | Synergism |
| | flumioxazin (B) | | | 2,4-D LV ester (C) | | | | | |
| | A | B | % activity | | % activity | | activity | activity | Y/N |
| weed | g ai/ha | g ai/ha | 20 DAT | g ai/ha | 20 DAT | g ai/ha | 20 DAT | 20 DAT | 20 DAT |
| ABUTH | 0.5 | 0.13 | 85 | 6.25 | 20 | 0.5 + 0.13 + 6.25 | 100 | 88 | Y |
| BRAPP | 0.25 | 0.25 | 0 | 6.25 | 20 | 0.25 + 0.25 + 6.25 | 40 | 20 | Y |

TABLE 27

Application in Post-Emergence of Saflufenacil, Flumioxazin and Topramezone

| | binary A + B and solo C applications | | | | combination saflufenacil + flumioxazin topramezone | | | |
|---|---|---|---|---|---|---|---|---|
| | saflufenacil (A) + | | | | | | | |
| | flumioxazin (B) | | topramezone (C) | | | observed % | expected % | Synergism |
| Weed | A g ai/ha | B g ai/ha | % activity 20 DAT | g ai/ha | % activity 20 DAT | g ai/ha | activity 20 DAT | activity 20 DAT | Y/N 20 DAT |
| SETVI | 0.5 | 0.25 | 25 | 0.5 | 0 | 0.5 + 0.25 + 0.5 | 70 | 25 | Y |
| ECHCG | 0.5 | 0.25 | 25 | 0.25 | 20 | 0.5 + 0.25 + 0.25 | 55 | 40 | Y |
| BRADC | 0.25 | 0.25 | 10 | 0.25 | 0 | 0.25 + 0.25 + 0.25 | 30 | 10 | Y |
| ABUTH | 0.25 | 0.25 | 85 | 0.25 | 0 | 0.25 + 0.25 + 0.25 | 95 | 85 | Y |

TABLE 28

Application in Post-Emergence of Saflufenacil, Flumioxazin and Fomesafen

| | binary A + B and solo C applications | | | | combination saflufenacil + flumioxazin + fomesafen | | | |
|---|---|---|---|---|---|---|---|---|
| | saflufenacil (A) + | | | | | | | |
| | flumioxazin (B) | | fomesafen (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 0.5 | 95 | 1.5 | 5 | 0.5 + 0.5 + 1.5 | 100 | 95 | Y |
| AVEFA | 0.25 | 0.5 | 60 | 1.5 | 20 | 0.25 + 0.5 + 1.5 | 75 | 68 | Y |
| BRADC | 0.25 | 0.5 | 75 | 3.0 | 30 | 0.25 + 0.5 + 3.0 | 90 | 83 | Y |

TABLE 29

Application in Post-Emergence of Saflufenacil, Flumioxazin and Clethodim

| | binary A + B and solo C applications | | | | combination saflufenacil + flumioxazin + clethodim | | | |
|---|---|---|---|---|---|---|---|---|
| | saflufenacil (A) + | | | | | | | |
| | flumioxazin (B) | | clethodim (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 0.5 | 95 | 0.75 | 5 | 0.5 + 0.5 + 0.75 | 100 | 95 | Y |

TABLE 30

Application in Post-Emergence of Saflufenacil, Dicamba and Acetochlor

| | binary A + B and solo C applications | | | | combination saflufenacil + dicamba + acetochlor | | | |
|---|---|---|---|---|---|---|---|---|
| | saflufenacil (A) + | | | | | | | |
| | dicamba (B) | | acetochlor (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.25 | 4.375 | 20 | 25.0 | 25 | 0.25 + 4.375 + 25.0 | 60 | 40 | Y |
| BRAPP | 0.5 | 8.75 | 25 | 50.0 | 5 | 0.5 + 8.75 + 50.0 | 50 | 29 | Y |

TABLE 31

Application in Post-Emergence of Saflufenacil, Dicamba and Pendimethalin

| | binary A + B and solo C applications | | | | | | | |
|---|---|---|---|---|---|---|---|---|
| | saflufenacil (A) + | | | | combination saflufenacil + dicamba + pendimethalin | | | |
| | dicamba (B) | | pendimethalin (C) | | | observed % | expected % | Synergism |
| Weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 4.375 | 30 | 37.5 | 0 | 0.5 + 4.375 + 37.5 | 60 | 30 | Y |
| ECHCG | 0.5 | 8.75 | 30 | 75.0 | 0 | 0.5 + 8.75 + 75.0 | 40 | 30 | Y |

TABLE 32

Application in Post-Emergence of Saflufenacil, Dicamba and Imazethapyr

| | binary A + B and solo C applications | | | | | | | |
|---|---|---|---|---|---|---|---|---|
| | saflufenacil (A) + | | | | combination saflufenacil + dicamba + imazethapyr | | | |
| | dicamba (B) | | imazethapyr (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 4.375 | 30 | 0.5 | 0 | 0.5 + 4.375 + 0.5 | 75 | 30 | Y |

TABLE 33

Application in Post-Emergence of Saflufenacil, Dicamba and Atrazine

| | binary A + B and solo C applications | | | | | | | |
|---|---|---|---|---|---|---|---|---|
| | saflufenacil (A) + | | | | combination saflufenacil + dicamba + atrazine | | | |
| | dicamba (B) | | atrazine (C) | | | observed % | expected % | Synergism |
| Weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 4.375 | 30 | 12.5 | 25 | 0.5 + 4.375 + 12.5 | 80 | 48 | Y |
| SETVI | 0.5 | 8.75 | 25 | 25.0 | 25 | 0.5 + 8.75 + 25.0 | 65 | 44 | Y |

TABLE 34

Application in Post-Emergence of Saflufenacil, Dicamba and Diclosulam

| | binary A + B and solo C applications | | | | | | | |
|---|---|---|---|---|---|---|---|---|
| | saflufenacil (A) + | | | | combination saflufenacil + dicamba + diclosulam | | | |
| | dicamba (B) | | diclosulam (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 4.375 | 30 | 0.125 | 10 | 0.5 + 4.375 + 0.125 | 75 | 37 | Y |
| BRAPP | 0.5 | 8.75 | 25 | 1.0 | 45 | 0.5 + 8.75 + 1.0 | 60 | 59 | Y |

TABLE 35

Application in Post-Emergence of Saflufenacil, Dicamba and Mesotrione

| | binary A + B and solo C applications | | | | combination saflufenacil + dicamba + mesotrione | | | |
|---|---|---|---|---|---|---|---|---|
| | saflufenacil (A) + | | | | | observed % | expected % | Synergism |
| | dicamba (B) | | mesotrione (C) | | | activity | activity | Y/N |
| Weed | A g ai/ha | B g ai/ha | % activity 20 DAT | g ai/ha | % activity 20 DAT | g ai/ha | 20 DAT | 20 DAT | 20 DAT |
| ABUTH | 0.5 | 4.375 | 30 | 0.625 | 75 | 0.5 + 4.375 + 0.625 | 90 | 83 | Y |
| BRAPP | 0.5 | 8.75 | 25 | 5.0 | 40 | 0.5 + 8.75 + 5.0 | 65 | 55 | Y |

TABLE 36

Application in Post-Emergence of Saflufenacil, Dicamba and Isoxaflutole

| | binary A + B and solo C applications | | | | combination saflufenacil + dicamba + isoxaflutole | | | |
|---|---|---|---|---|---|---|---|---|
| | saflufenacil (A) + | | | | | observed % | expected % | Synergism |
| | dicamba (B) | | isoxaflutole (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| ABUTH | 0.25 | 4.375 | 20 | 0.5 | 50 | 0.25 + 4.375 + 0.5 | 80 | 60 | Y |

TABLE 37

Application in Post-Emergence of Saflufenacil, Dicamba and Topramezone

| | binary A + B and solo C applications | | | | combination saflufenacil + dicamba + topramezone | | | |
|---|---|---|---|---|---|---|---|---|
| | saflufenacil (A) + | | | | | observed % | expected % | Synergism |
| | dicamba (B) | | topramezone (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| SETVI | 0.5 | 8.5 | 15 | 0.25 | 0 | 0.5 + 8.5 + 0.25 | 50 | 15 | Y |
| ECHCG | 0.5 | 8.5 | 35 | 0.25 | 25 | 0.5 + 8.5 + 0.25 | 55 | 51 | Y |
| AVEFA | 0.5 | 8.5 | 10 | 0.25 | 0 | 0.5 + 8.5 + 0.25 | 20 | 10 | Y |
| AMARE | 0.25 | 8.5 | 95 | 0.25 | 40 | 0.25 + 8.5 + 0.25 | 100 | 97 | Y |
| ABUTH | 0.25 | 8.5 | 15 | 0.25 | 10 | 0.25 + 8.5 + 0.25 | 50 | 24 | Y |

TABLE 38

Application in Post-Emergence of Saflufenacil, Dicamba and Imazamox

| | binary A + B and solo C applications | | | | combination saflufenacil + dicamba imazamox | | | |
|---|---|---|---|---|---|---|---|---|
| | saflufenacil (A) + | | | | | observed % | expected % | Synergism |
| | dicamba (B) | | imazamox (C) | | | activity | activity | Y/N |
| weed | A g ai/ha | B g ai/ha | % activity 20 DAT | g ai/ha | % activity 20 DAT | g ai/ha | 20 DAT | 20 DAT | 20 DAT |
| SETVI | 0.25 | 8.5 | 0 | 0.5 | 15 | 0.25 + 8.5 + 0.5 | 70 | 15 | Y |
| DIGSA | 0.25 | 8.5 | 10 | 0.5 | 10 | 0.25 + 8.5 + 0.5 | 40 | 19 | Y |
| AMARE | 0.25 | 8.5 | 95 | 0.5 | 40 | 0.25 + 8.5 + 0.5 | 100 | 97 | Y |
| ABUTH | 0.25 | 8.5 | 15 | 0.5 | 0 | 0.25 + 8.5 + 0.5 | 45 | 15 | Y |

TABLE 39

Application in Post-Emergence of Saflufenacil, Dicamba and Dimethenamid-P

| | binary A + B and solo C applications | | | | | combination saflufenacil + dicamba + dimethenamid-P | | | |
|---|---|---|---|---|---|---|---|---|---|
| | saflufenacil (A) + | | | | | | | | |
| | dicamba (B) | | | dimethenamid-P (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ECHCG | 0.25 | 8.5 | 10 | 75 | 80 | 0.25 + 8.5 + 75 | 90 | 82 | Y |
| AMARE | 0.25 | 8.5 | 95 | 37.5 | 0 | 0.25 + 8.5 + 37.5 | 100 | 95 | Y |
| ABUTH | 0.5 | 8.5 | 60 | 37.5 | 0 | 0.5 + 8.5 + 37.5 | 80 | 60 | Y |

TABLE 40

Application in Post-Emergence of Saflufenacil, Dicamba and Fomesafen

| | binary A + B and solo C applications | | | | | combination saflufenacil + dicamba + fomesafen | | | |
|---|---|---|---|---|---|---|---|---|---|
| | saflufenacil (A) + | | | | | | | | |
| | dicamba (B) | | | fomesafen (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 6.0 | 45 | 3.0 | 20 | 0.5 + 6.0 + 3.0 | 60 | 56 | Y |
| AMARE | 0.5 | 6.0 | 95 | 3.0 | 65 | 0.5 + 6.0 + 3.0 | 100 | 98 | Y |
| DIGSA | 0.25 | 6.0 | 30 | 1.5 | 20 | 0.25 + 6.0 + 1.5 | 50 | 44 | Y |
| ECHCG | 0.5 | 6.0 | 25 | 1.5 | 20 | 0.5 + 6.0 + 1.5 | 55 | 40 | Y |

TABLE 41

Application in Post-Emergence of Saflufenacil, Dicamba and Clethodim

| | binary A + B and solo C applications | | | | | combination saflufenacil + dicamba + clethodim | | | |
|---|---|---|---|---|---|---|---|---|---|
| | saflufenacil (A) + | | | | | | | | |
| | dicamba (B) | | | clethodim (C) | | | observed % | expected % | Synergism |
| weed | A g ai/ha | B g ai/ha | % activity 20 DAT | g ai/ha | % activity 20 DAT | g ai/ha | activity 20 DAT | activity 20 DAT | Y/N 20 DAT |
| ABUTH | 0.5 | 6.0 | 45 | 0.75 | 5 | 0.5 + 6.0 + 0.75 | 55 | 48 | Y |
| AMARE | 0.5 | 6.0 | 95 | 0.75 | 20 | 0.5 + 6.0 + 0.75 | 100 | 96 | Y |
| DIGSA | 0.25 | 6.0 | 30 | 0.75 | 0 | 0.25 + 6.0 + 0.75 | 40 | 30 | Y |

The invention claimed is:

1. A herbicidal composition comprising
    a) a herbicide A which is 2-chloro-5-[3,6-dihydro-3-methyl-2,6-dioxo-4-(trifluoromethyl)-1-(2H)-pyrimidinyl]-4-fluoro-N-[[methyl-(1-methylethyl)-amino]sulfonyl]benzamide,
    b) a single herbicide B selected from the group consisting of sulfentrazone, flumioxazin, dicamba and their salts and esters, and
    c) at least one herbicide C different from herbicides A and B which is selected from the group consisting of fomesafen, dimethenamid, acetochlor, pendimethalin, dicamba, imazamox, imazethapyr, atrazine, diclosulam, mesotrione, isoxaflutole, topramezone, clethodim, 2,4-D, and their agriculturally acceptable enantiomers, salts and esters,
    wherein the weight ratio of B to A is 35:1 to 1:5; the weight ratio of A to C is 1:75 to 10:1 and the weight ratio of B to the sum of A and C is 30:1 to 1:60;
    provided that the herbicidal composition does not include pyroxasulfone, metolachlor, or s-metolachlor;
    provided that in case the components b) or c) comprise dicamba or one of its salts or esters the herbicidal composition does not include imazapyr or one of its salts; and
    provided that if component b) is flumioxazin, component c) is not 2,4-D or its salt or ester.

2. The herbicidal composition of claim 1, wherein the at least one herbicide C is diclosulam, imazamox or imazethapyr, or their agriculturally acceptable salts or esters.

3. The herbicidal composition of claim 1, wherein the at least one herbicide C is fomesafen or its agriculturally acceptable salt or ester.

4. The herbicidal composition of claim 1, wherein the at least one herbicide C is dicamba or 2,4-D, or their agriculturally acceptable salts or esters.

5. The herbicidal composition claim 1, wherein the at least one herbicide C is pendimethalin.

6. The herbicidal composition of claim 1, wherein the at least one herbicide C is atrazine or its agriculturally acceptable salt.

7. The herbicidal composition of claim 1, wherein the at least one herbicide C is mesotrione or topramezone or their agriculturally acceptable salts.

8. The herbicidal composition of claim 1, wherein the at least one herbicide C is dimethenamid or acetochlor or their agriculturally acceptable enantiomers.

9. The herbicidal composition of claim 1, wherein the herbicide B is sulfentrazone.

10. The herbicidal composition of claim 1, wherein the herbicide B is flumioxazin.

11. The herbicidal composition of claim 1, wherein the herbicide B is selected from the group consisting of dicamba and its agriculturally acceptable salts and esters.

12. A method for controlling undesirable vegetation, which method comprises applying the herbicidal composition of claim 1 to a locus where undesirable vegetation is present or is expected to be present.

13. A method for burn-down treatment of undesirable vegetation in crops, comprising applying the herbicidal composition of claim 1 to a locus where crops will be planted before planting or emergence of the crop.

14. A herbicidal composition comprising
a) a herbicide A which is 2-chloro-5-[3,6-dihydro-3-methyl-2,6-dioxo-4-(trifluoromethyl)-1-(2H)-pyrimidinyl]-4-fluoro-N-[[methyl-(1-methylethyl)-amino]sulfonyl]benzamide,
b) a single herbicide B selected from the group consisting of sulfentrazone, flumioxazin, dicamba and their salts and esters, and
c) at least one herbicide C different from herbicides A and B which is selected from the group consisting of fomesafen, dimethenamid, acetochlor, pendimethalin, dicamba, imazamox, imazethapyr, atrazine, diclosulam, mesotrione, isoxaflutole, topramezone, clethodim, 2,4-D, and their agriculturally acceptable enantiomers, salts and esters,
wherein:
the weight ratio of B to A is 35:1 to 1:5;
the weight ratio of A to C is 1:75 to 10:1 and
the weight ratio of B to the sum of A and C is 30:1 to 1:60;
provided that the herbicidal composition does not include pyroxasulfone;
provided that in case the components b) or c) is dicamba or one of its salts or esters the herbicidal composition does not include imazapyr or one of its salts;
provided that if the component b) is flumioxazin, component c) is not 2,4-D or its salt or ester; and
provided that in case the component b) is flumioxazin, component c) is not fomesafen or its salt.

15. The herbicidal composition of claim 14, wherein the herbicide B is sulfentrazone.

16. The herbicidal composition of claim 14, wherein the herbicide B is flumioxazin.

17. The herbicidal composition of claim 14, wherein the herbicide B is selected from the group consisting of dicamba and its agriculturally acceptable salts and esters.

* * * * *